(12) United States Patent
Wentorf et al.

(10) Patent No.: US 10,265,181 B2
(45) Date of Patent: *Apr. 23, 2019

(54) TIBIAL BASEPLATE WITH ASYMMETRIC PLACEMENT OF FIXATION STRUCTURES

(71) Applicant: Zimmer, Inc., Warsaw, IN (US)

(72) Inventors: Mary S. S. Wentorf, Warsaw, IN (US);
Calie B. Grey, Warsaw, IN (US);
Shaun R. Cronin, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/616,561

(22) Filed: Jun. 7, 2017

(65) Prior Publication Data

US 2017/0266011 A1  Sep. 21, 2017

Related U.S. Application Data

(63) Continuation of application No. 15/045,799, filed on Feb. 17, 2016, now Pat. No. 9,707,089, which is a continuation of application No. 14/278,805, filed on May 15, 2014, now Pat. No. 9,308,096, which is a continuation of application No. 13/593,339, filed on Aug. 23, 2012, now Pat. No. 8,758,444.

(Continued)

(51) Int. Cl.
*A61F 2/38* (2006.01)
*A61F 2/30* (2006.01)
*A61F 2/28* (2006.01)

(52) U.S. Cl.
CPC .......... *A61F 2/389* (2013.01); *A61F 2/3886* (2013.01); *A61F 2002/2892* (2013.01); *A61F 2002/30326* (2013.01); *A61F 2002/30616* (2013.01); *A61F 2002/30878* (2013.01); *A61F 2002/30884* (2013.01); *A61F 2002/30891* (2013.01); *A61F 2002/30892* (2013.01)

(58) Field of Classification Search
CPC . A61F 2/389; A61F 2/3868; A61F 2002/2892
See application file for complete search history.

(56) References Cited

U.S. PATENT DOCUMENTS

| 3,774,244 A | 11/1973 | Walker |
| 4,016,606 A | 4/1977 | Murray et al. |

(Continued)

FOREIGN PATENT DOCUMENTS

| AU | 2011343440 B2 | 4/2014 |
| AU | 2011286306 B2 | 10/2014 |

(Continued)

OTHER PUBLICATIONS

"U.S. Appl. No. 13/087,610, Non Final Office Action dated Feb. 26, 2013", 7 pgs.

(Continued)

*Primary Examiner* — Jason-Dennis N Stewart
(74) *Attorney, Agent, or Firm* — Schwegman Lundberg & Woessner, P.A.

(57) ABSTRACT

An orthopedic knee prosthesis is provided including a tibial baseplate component having a distal, bone-contacting surface with one or more fixation structures extending distally therefrom, in which the fixation structures are asymmetrically arranged within the baseplate periphery.

17 Claims, 13 Drawing Sheets

Related U.S. Application Data

(60) Provisional application No. 61/621,369, filed on Apr. 6, 2012, provisional application No. 61/621,374, filed on Apr. 6, 2012, provisional application No. 61/594,030, filed on Feb. 2, 2012, provisional application No. 61/592,571, filed on Jan. 30, 2012, provisional application No. 61/592,574, filed on Jan. 30, 2012, provisional application No. 61/562,133, filed on Nov. 21, 2011.

(56) References Cited

U.S. PATENT DOCUMENTS

| | | | |
|---|---|---|---|
| 4,257,129 | A | 3/1981 | Volz |
| 4,340,978 | A | 7/1982 | Buechel et al. |
| 4,501,266 | A | 2/1985 | McDaniel |
| 4,568,348 | A | 2/1986 | Johnson et al. |
| 4,714,474 | A | 12/1987 | Brooks, Jr. et al. |
| 4,759,767 | A | 7/1988 | Lacey |
| 4,769,040 | A | 9/1988 | Wevers |
| 4,770,661 | A | 9/1988 | Oh |
| 4,795,468 | A | 1/1989 | Hodorek et al. |
| 4,822,365 | A | 4/1989 | Walker et al. |
| 4,936,853 | A | 6/1990 | Fabian et al. |
| 4,944,757 | A | 7/1990 | Martinez et al. |
| 4,950,298 | A | 8/1990 | Gustilo et al. |
| 4,959,071 | A | 9/1990 | Brown et al. |
| 4,963,152 | A | 10/1990 | Hofmann et al. |
| 5,047,057 | A | 9/1991 | Lawes |
| 5,047,058 | A | 9/1991 | Roberts et al. |
| 5,059,216 | A | 10/1991 | Winters |
| 5,061,271 | A | 10/1991 | Van Zile |
| 5,071,438 | A | 12/1991 | Jones et al. |
| 5,116,375 | A | 5/1992 | Hofmann |
| 5,133,758 | A | 7/1992 | Hollister |
| 5,137,536 | A | 8/1992 | Koshino |
| 5,147,405 | A | 9/1992 | Van Zile |
| 5,171,283 | A | 12/1992 | Pappas et al. |
| 5,192,328 | A | 3/1993 | Winters |
| 5,197,488 | A | 3/1993 | Kovacevic |
| 5,219,362 | A | 6/1993 | Tuke et al. |
| 5,236,461 | A | 8/1993 | Forte |
| 5,246,459 | A | 9/1993 | Elias |
| 5,271,737 | A * | 12/1993 | Baldwin ............... A61F 2/389 623/20.34 |
| 5,275,603 | A | 1/1994 | Ferrante et al. |
| 5,282,861 | A | 2/1994 | Kaplan |
| 5,282,868 | A | 2/1994 | Bahler |
| 5,282,870 | A | 2/1994 | Moser et al. |
| 5,290,313 | A | 3/1994 | Heldreth |
| 5,310,480 | A | 5/1994 | Vidueira |
| 5,326,361 | A | 7/1994 | Hollister |
| 5,344,460 | A | 9/1994 | Turanyi et al. |
| 5,344,461 | A | 9/1994 | Phlipot |
| 5,360,016 | A | 11/1994 | Kovacevic |
| 5,364,402 | A | 11/1994 | Mumme et al. |
| 5,370,699 | A | 12/1994 | Hood et al. |
| 5,387,239 | A | 2/1995 | Bianco et al. |
| 5,387,240 | A | 2/1995 | Pottenger et al. |
| 5,395,401 | A | 3/1995 | Bahler |
| 5,405,396 | A | 4/1995 | Heldreth et al. |
| 5,413,604 | A | 5/1995 | Hodge |
| 5,413,605 | A | 5/1995 | Ashby et al. |
| 5,425,775 | A | 6/1995 | Kovacevic et al. |
| 5,458,637 | A | 10/1995 | Hayes |
| 5,470,354 | A | 11/1995 | Hershberger et al. |
| 5,489,311 | A | 2/1996 | Cipolletti |
| 5,507,820 | A | 4/1996 | Pappas |
| 5,549,688 | A | 8/1996 | Ries et al. |
| 5,556,433 | A | 9/1996 | Gabriel et al. |
| 5,571,194 | A | 11/1996 | Gabriel |
| 5,609,639 | A | 3/1997 | Walker |
| 5,609,641 | A | 3/1997 | Johnson et al. |
| 5,609,643 | A | 3/1997 | Colleran et al. |
| 5,609,645 | A | 3/1997 | Vinciuerra |
| 5,613,970 | A | 3/1997 | Houston et al. |
| 5,656,785 | A | 8/1997 | Trainor et al. |
| 5,658,341 | A | 8/1997 | Delfosse |
| 5,658,342 | A | 8/1997 | Draganich et al. |
| 5,658,344 | A | 8/1997 | Hurlburt |
| 5,683,470 | A | 11/1997 | Johnson et al. |
| 5,702,463 | A | 12/1997 | Pothier et al. |
| 5,702,464 | A | 12/1997 | Lackey et al. |
| 5,733,292 | A | 3/1998 | Gustilo et al. |
| 5,755,801 | A | 5/1998 | Walker et al. |
| 5,755,802 | A | 5/1998 | Gerber |
| 5,776,200 | A | 7/1998 | Johnson et al. |
| 5,782,925 | A | 7/1998 | Collazo et al. |
| 5,824,100 | A | 10/1998 | Kester et al. |
| 5,824,102 | A | 10/1998 | Buscayret |
| 5,824,103 | A | 10/1998 | Williams et al. |
| 5,871,539 | A | 2/1999 | Pappas |
| 5,871,541 | A | 2/1999 | Gerber |
| 5,871,543 | A | 2/1999 | Hofmann |
| 5,871,545 | A | 2/1999 | Goodfellow et al. |
| 5,879,394 | A | 3/1999 | Ashby et al. |
| 5,906,643 | A | 5/1999 | Walker |
| 5,911,723 | A | 6/1999 | Ashby et al. |
| 5,928,286 | A | 7/1999 | Ashby et al. |
| 5,964,808 | A | 10/1999 | Blaha et al. |
| 5,968,099 | A | 10/1999 | Badorf et al. |
| 5,976,147 | A | 11/1999 | LaSalle et al. |
| 6,004,351 | A | 12/1999 | Tomita et al. |
| 6,004,352 | A | 12/1999 | Buni |
| 6,010,534 | A | 1/2000 | O'neil et al. |
| 6,013,103 | A | 1/2000 | Kaufman et al. |
| 6,039,764 | A | 3/2000 | Pottenger et al. |
| 6,068,658 | A | 5/2000 | Insall et al. |
| 6,074,425 | A | 6/2000 | Pappas |
| 6,080,195 | A | 6/2000 | Colleran et al. |
| 6,090,144 | A | 7/2000 | Letot et al. |
| 6,102,954 | A | 8/2000 | Albrektsson et al. |
| 6,102,955 | A | 8/2000 | Mendes et al. |
| 6,123,729 | A | 9/2000 | Insall et al. |
| 6,126,692 | A | 10/2000 | Robie et al. |
| 6,143,034 | A | 11/2000 | Burrows |
| 6,197,064 | B1 | 3/2001 | Haines et al. |
| 6,203,576 | B1 | 3/2001 | Afriat et al. |
| 6,206,927 | B1 | 3/2001 | Fell et al. |
| 6,210,443 | B1 | 4/2001 | Marceaux et al. |
| RE37,277 | E | 7/2001 | Baldwin et al. |
| 6,258,127 | B1 | 7/2001 | Schmotzer |
| 6,306,172 | B1 | 10/2001 | O'Neil et al. |
| 6,325,828 | B1 | 12/2001 | Dennis et al. |
| 6,379,388 | B1 | 4/2002 | Ensign et al. |
| 6,406,497 | B2 | 6/2002 | Takei et al. |
| 6,413,279 | B1 | 7/2002 | Metzger et al. |
| 6,428,577 | B1 | 8/2002 | Evans |
| 6,436,145 | B1 | 8/2002 | Miller |
| 6,491,726 | B2 | 12/2002 | Pappas |
| 6,506,215 | B1 | 1/2003 | Letot et al. |
| 6,506,216 | B1 | 1/2003 | McCue et al. |
| 6,558,426 | B1 | 5/2003 | Masini |
| 6,607,559 | B2 | 8/2003 | Ralph et al. |
| 6,623,526 | B1 | 9/2003 | Lloyd |
| 6,632,225 | B2 | 10/2003 | Sanford et al. |
| 6,660,039 | B1 | 12/2003 | Evans et al. |
| 6,702,821 | B2 | 3/2004 | Bonutti |
| 6,709,461 | B2 | 3/2004 | O'neil et al. |
| 6,743,258 | B1 | 6/2004 | Keller |
| 6,755,864 | B1 | 6/2004 | Brack et al. |
| 6,770,078 | B2 | 8/2004 | Bonutti |
| 6,869,448 | B2 | 3/2005 | Tuke |
| 6,923,832 | B1 | 8/2005 | Sharkey et al. |
| 6,942,670 | B2 | 9/2005 | Heldreth et al. |
| 6,953,479 | B2 | 10/2005 | Carson et al. |
| 6,974,481 | B1 | 12/2005 | Carson |
| 6,986,791 | B1 | 1/2006 | Metzger |
| 7,025,788 | B2 | 4/2006 | Metzger et al. |
| 7,060,074 | B2 | 6/2006 | Rosa et al. |
| 7,081,137 | B1 | 7/2006 | Servidio |
| 7,083,652 | B2 | 8/2006 | McCue et al. |
| 7,153,326 | B1 | 12/2006 | Metzger |
| 7,160,330 | B2 | 1/2007 | Axelson, Jr. et al. |

(56) References Cited

U.S. PATENT DOCUMENTS

| | | |
|---|---|---|
| 7,189,262 B2 | 3/2007 | Hayes, Jr. et al. |
| 7,261,740 B2 | 8/2007 | Tuttle |
| 7,264,635 B2 | 9/2007 | Suguro |
| 7,294,149 B2 | 11/2007 | Hozack et al. |
| 7,309,362 B2 | 12/2007 | Yasuda et al. |
| 7,309,363 B2 | 12/2007 | Dietz |
| 7,326,252 B2 | 2/2008 | Otto et al. |
| 7,351,263 B2 | 4/2008 | Afriat |
| 7,364,581 B2 | 4/2008 | Michalowicz |
| 7,412,897 B2 | 8/2008 | Crottet et al. |
| 7,413,577 B1 | 8/2008 | Servidio |
| 7,442,196 B2 | 10/2008 | Fisher et al. |
| 7,445,639 B2 | 11/2008 | Metzger et al. |
| 7,488,330 B2 | 2/2009 | Stad |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,547,327 B2 | 6/2009 | Collazo |
| 7,575,602 B2 | 8/2009 | Amirouche et al. |
| 7,578,821 B2 | 8/2009 | Fisher et al. |
| 7,585,328 B2 | 9/2009 | Haas |
| 7,587,945 B2 | 9/2009 | Crottet et al. |
| 7,591,854 B2 | 9/2009 | Wasielewski |
| 7,625,407 B2 | 12/2009 | Akizuki |
| 7,628,818 B2 | 12/2009 | Hazebrouck et al. |
| 7,632,283 B2 | 12/2009 | Heldreth |
| 7,632,314 B2 | 12/2009 | Dietz |
| 7,635,390 B1 | 12/2009 | Bonutti |
| 7,678,152 B2 | 3/2010 | Suguro et al. |
| 7,695,519 B2 | 4/2010 | Collazo |
| 7,695,520 B2 | 4/2010 | Metzger et al. |
| 7,776,085 B2 | 8/2010 | Bernero et al. |
| 7,837,691 B2 | 11/2010 | Cordes et al. |
| 7,850,698 B2 | 12/2010 | Straszheim-Morley et al. |
| 8,012,216 B2 | 9/2011 | Metzger |
| 8,065,927 B2 | 11/2011 | Crottet et al. |
| 8,141,437 B2 | 3/2012 | Amirouche et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,491,589 B2 | 7/2013 | Fisher et al. |
| 8,506,571 B2 | 8/2013 | Chana et al. |
| 8,568,486 B2 | 10/2013 | Wentorf et al. |
| 8,574,304 B2 | 11/2013 | Wentorf et al. |
| 8,591,594 B2 | 11/2013 | Parisi et al. |
| 8,603,101 B2 | 12/2013 | Claypool et al. |
| 8,613,775 B2 | 12/2013 | Wentorf et al. |
| 8,628,580 B2 | 1/2014 | Sanford et al. |
| 8,690,954 B2 | 4/2014 | Parisi et al. |
| 8,758,444 B2 | 6/2014 | Wentorf et al. |
| 8,764,838 B2 | 7/2014 | Parisi et al. |
| 8,764,840 B2 | 7/2014 | Sanford et al. |
| 8,858,643 B2 | 10/2014 | Parisi et al. |
| 8,932,298 B2 | 1/2015 | Colquhoun et al. |
| 8,932,365 B2 | 1/2015 | Parisi et al. |
| 8,979,847 B2 | 3/2015 | Belcher et al. |
| 9,011,459 B2 | 4/2015 | Claypool et al. |
| 9,072,607 B2 | 7/2015 | Parisi et al. |
| 9,149,206 B2 | 10/2015 | Claypool et al. |
| 9,186,255 B2 | 11/2015 | Parisi |
| 9,192,480 B2 | 11/2015 | Wentorf et al. |
| 9,204,970 B2 | 12/2015 | Parisi et al. |
| 9,283,082 B2 | 3/2016 | Sanford et al. |
| 9,295,557 B2 | 3/2016 | Wentorf et al. |
| 9,295,558 B2 | 3/2016 | Parisi et al. |
| 9,308,096 B2 | 4/2016 | Wentorf et al. |
| 9,314,343 B2 | 4/2016 | Parisi et al. |
| 9,381,090 B2 | 7/2016 | Wentorf et al. |
| 9,427,337 B2 | 8/2016 | Claypool et al. |
| 9,492,290 B2 | 11/2016 | Claypool et al. |
| 9,539,116 B2 | 1/2017 | Claypool |
| 9,592,133 B2 | 3/2017 | Toler et al. |
| 9,597,090 B2 | 3/2017 | Claypool et al. |
| 9,655,728 B2 | 5/2017 | Parisi et al. |
| 9,655,729 B2 | 5/2017 | Parisi et al. |
| 9,707,089 B2 | 7/2017 | Grey et al. |
| 9,763,794 B2 | 9/2017 | Sanford et al. |
| 9,763,795 B2 | 9/2017 | Parisi et al. |
| 9,763,796 B2 | 9/2017 | Wentorf et al. |
| 9,763,807 B2 | 9/2017 | Claypool et al. |
| 9,788,954 B2 | 10/2017 | Parisi et al. |
| 9,861,490 B2 | 1/2018 | Wentorf et al. |
| 9,901,331 B2 | 2/2018 | Toler et al. |
| 9,918,844 B2 | 3/2018 | Sanford et al. |
| 2001/0047210 A1 | 11/2001 | Wolf |
| 2002/0058997 A1 | 5/2002 | O'Connor et al. |
| 2002/0072802 A1 | 6/2002 | O'Neil et al. |
| 2002/0120340 A1 | 8/2002 | Metzger et al. |
| 2002/0161448 A1 | 10/2002 | Hayes, Jr. et al. |
| 2003/0055509 A1* | 3/2003 | McCue ............... A61F 2/389 623/20.32 |
| 2004/0019382 A1 | 1/2004 | Amirouche et al. |
| 2004/0034432 A1 | 2/2004 | Hughes et al. |
| 2004/0059340 A1 | 3/2004 | Serra et al. |
| 2004/0064191 A1 | 4/2004 | Wasielewski |
| 2004/0122441 A1 | 6/2004 | Muratsu |
| 2004/0153066 A1 | 8/2004 | Coon et al. |
| 2004/0162620 A1 | 8/2004 | Wyss |
| 2004/0167537 A1 | 8/2004 | Errico et al. |
| 2004/0186582 A1 | 9/2004 | Yasuda et al. |
| 2004/0204765 A1 | 10/2004 | Fenning et al. |
| 2004/0225368 A1 | 11/2004 | Plumet et al. |
| 2004/0236429 A1 | 11/2004 | Ensign et al. |
| 2004/0243244 A1 | 12/2004 | Otto et al. |
| 2004/0267371 A1 | 12/2004 | Hayes, Jr. et al. |
| 2005/0055102 A1 | 3/2005 | Tornier et al. |
| 2005/0096747 A1 | 5/2005 | Tuttle et al. |
| 2005/0143831 A1 | 6/2005 | Justin et al. |
| 2005/0143832 A1 | 6/2005 | Carson |
| 2005/0177170 A1 | 8/2005 | Fisher et al. |
| 2005/0197710 A1 | 9/2005 | Naegerl |
| 2005/0209701 A1 | 9/2005 | Suguro et al. |
| 2005/0209702 A1 | 9/2005 | Todd et al. |
| 2005/0246030 A1 | 11/2005 | Yao |
| 2005/0267485 A1 | 12/2005 | Cordes et al. |
| 2005/0267584 A1 | 12/2005 | Burdulis, Jr. et al. |
| 2005/0278035 A1 | 12/2005 | Wyss et al. |
| 2006/0004460 A1 | 1/2006 | Engh et al. |
| 2006/0020343 A1 | 1/2006 | Ek |
| 2006/0030945 A1 | 2/2006 | Wright |
| 2006/0052782 A1 | 3/2006 | Morgan et al. |
| 2006/0069436 A1 | 3/2006 | Sutton et al. |
| 2006/0089653 A1 | 4/2006 | Auger et al. |
| 2006/0142869 A1 | 6/2006 | Gross |
| 2006/0161259 A1 | 7/2006 | Cheng et al. |
| 2006/0184176 A1 | 8/2006 | Straszheim-Morley et al. |
| 2006/0189864 A1 | 8/2006 | Paradis et al. |
| 2006/0190087 A1 | 8/2006 | O'Connor et al. |
| 2006/0195195 A1 | 8/2006 | Burstein et al. |
| 2006/0111726 A1 | 10/2006 | Felt et al. |
| 2006/0224244 A1 | 10/2006 | Thomas et al. |
| 2006/0265080 A1 | 11/2006 | Mcminn |
| 2007/0010890 A1 | 1/2007 | Collazo |
| 2007/0123992 A1 | 5/2007 | Sanford |
| 2007/0129808 A1 | 6/2007 | Justin et al. |
| 2007/0135926 A1 | 6/2007 | Walker |
| 2007/0185581 A1 | 8/2007 | Akizuki et al. |
| 2007/0198022 A1 | 8/2007 | Lang et al. |
| 2007/0233269 A1 | 10/2007 | Steines et al. |
| 2007/0234819 A1 | 10/2007 | Amirouche et al. |
| 2007/0239165 A1 | 10/2007 | Amirouche |
| 2008/0021566 A1 | 1/2008 | Peters et al. |
| 2008/0051908 A1 | 2/2008 | Angibaud et al. |
| 2008/0091271 A1 | 4/2008 | Bonitati et al. |
| 2008/0091272 A1 | 4/2008 | Aram et al. |
| 2008/0091273 A1 | 4/2008 | Hazebrouck |
| 2008/0103603 A1 | 5/2008 | Hintermann |
| 2008/0114462 A1 | 5/2008 | Guidera et al. |
| 2008/0119938 A1 | 5/2008 | Oh |
| 2008/0119940 A1 | 5/2008 | Otto et al. |
| 2008/0161918 A1 | 7/2008 | Fankhauser et al. |
| 2008/0167722 A1 | 7/2008 | Metzger et al. |
| 2008/0215156 A1 | 9/2008 | Duggal et al. |
| 2008/0243258 A1 | 10/2008 | Sancheti |

(56) References Cited

U.S. PATENT DOCUMENTS

| | | |
|---|---|---|
| 2008/0281426 A1 | 11/2008 | Fitz et al. |
| 2008/0288080 A1 | 11/2008 | Sancheti |
| 2008/0300689 A1 | 12/2008 | Mc Kinnon et al. |
| 2008/0300690 A1 | 12/2008 | Burstein et al. |
| 2009/0005708 A1 | 1/2009 | Johanson et al. |
| 2009/0036992 A1 | 2/2009 | Tsakonas |
| 2009/0043395 A1 | 2/2009 | Hotokebuchi et al. |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |
| 2009/0149964 A1 | 6/2009 | May et al. |
| 2009/0204221 A1 | 8/2009 | Walker |
| 2009/0204222 A1 | 8/2009 | Burstein et al. |
| 2009/0210066 A1 | 8/2009 | Jasty |
| 2009/0222103 A1 | 9/2009 | Fitz et al. |
| 2009/0259314 A1 | 10/2009 | Linder-ganz et al. |
| 2009/0264894 A1 | 10/2009 | Wasielewski |
| 2009/0265011 A1 | 10/2009 | Mandell |
| 2009/0265013 A1 | 10/2009 | Mandell |
| 2009/0287310 A1 | 11/2009 | Fisher et al. |
| 2009/0306786 A1 | 12/2009 | Samuelson |
| 2009/0306787 A1 | 12/2009 | Crabtree et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0010494 A1 | 1/2010 | Quirno |
| 2010/0016976 A1 | 1/2010 | Siebel |
| 2010/0016977 A1 | 1/2010 | Masini |
| 2010/0016978 A1 | 1/2010 | Williams et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0063594 A1 | 3/2010 | Hazebrouck et al. |
| 2010/0063595 A1 | 3/2010 | Dietz |
| 2010/0076563 A1 | 3/2010 | Otto et al. |
| 2010/0082111 A1 | 4/2010 | Thomas |
| 2010/0100011 A1 | 4/2010 | Roche |
| 2010/0100189 A1 | 4/2010 | Metzger |
| 2010/0100191 A1 | 4/2010 | May et al. |
| 2010/0125339 A1 | 5/2010 | Earl et al. |
| 2010/0152858 A1 | 6/2010 | Lu et al. |
| 2010/0191341 A1 | 7/2010 | Byrd |
| 2010/0198275 A1 | 8/2010 | Chana et al. |
| 2010/0222890 A1 | 9/2010 | Barnett et al. |
| 2010/0249660 A1 | 9/2010 | Sherman et al. |
| 2010/0249789 A1 | 9/2010 | Rock et al. |
| 2010/0262253 A1 | 10/2010 | Cipolletti et al. |
| 2010/0286788 A1 | 11/2010 | Komistek |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0040387 A1 | 2/2011 | Ries et al. |
| 2011/0082558 A1 | 4/2011 | Kim et al. |
| 2011/0082559 A1 | 4/2011 | Hartdegen et al. |
| 2011/0087332 A1 | 4/2011 | Bojarski et al. |
| 2011/0100011 A1 | 5/2011 | Staffend |
| 2011/0125278 A1 | 5/2011 | Bercovy et al. |
| 2011/0144760 A1 | 6/2011 | Wong et al. |
| 2011/0251695 A1 | 10/2011 | Lenz et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford et al. |
| 2012/0095563 A1 | 4/2012 | Sanford et al. |
| 2012/0101585 A1 | 4/2012 | Parisi et al. |
| 2012/0158152 A1 | 6/2012 | Claypool et al. |
| 2012/0179069 A1 | 7/2012 | Amirouche |
| 2012/0185054 A1 | 7/2012 | Maloney et al. |
| 2012/0232429 A1 | 9/2012 | Fischer et al. |
| 2012/0290088 A1 | 11/2012 | Amirouche et al. |
| 2012/0310246 A1 | 12/2012 | Belcher et al. |
| 2012/0323336 A1 | 12/2012 | Parisi et al. |
| 2013/0013076 A1 | 1/2013 | Fisher et al. |
| 2013/0024001 A1 | 1/2013 | Wentorf et al. |
| 2013/0079671 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0131816 A1 | 5/2013 | Parisi et al. |
| 2013/0131817 A1 | 5/2013 | Parisi et al. |
| 2013/0131818 A1 | 5/2013 | Parisi et al. |
| 2013/0131819 A1 | 5/2013 | Parisi et al. |
| 2013/0131820 A1 | 5/2013 | Wentorf et al. |
| 2013/0173010 A1 | 7/2013 | Irwin et al. |
| 2013/0253378 A1 | 9/2013 | Claypool et al. |
| 2013/0261504 A1 | 10/2013 | Claypool et al. |
| 2013/0261757 A1 | 10/2013 | Claypool et al. |
| 2013/0261758 A1 | 10/2013 | Claypool et al. |
| 2014/0025175 A1 | 1/2014 | Wentorf et al. |
| 2014/0025176 A1 | 1/2014 | Wentorf |
| 2014/0025177 A1 | 1/2014 | Wentorf et al. |
| 2014/0052268 A1 | 2/2014 | Sanford et al. |
| 2014/0052269 A1 | 2/2014 | Claypool et al. |
| 2014/0156015 A1 | 6/2014 | Parisi et al. |
| 2014/0163687 A1 | 6/2014 | Parisi et al. |
| 2014/0249641 A1 | 9/2014 | Wentorf et al. |
| 2014/0257505 A1 | 9/2014 | Parisi et al. |
| 2014/0257506 A1 | 9/2014 | Sanford et al. |
| 2014/0296859 A1 | 10/2014 | Claypool et al. |
| 2015/0005890 A1 | 1/2015 | Parisi et al. |
| 2015/0088140 A1 | 3/2015 | Toler et al. |
| 2015/0190243 A1 | 7/2015 | Claypool et al. |
| 2015/0282936 A1 | 10/2015 | Parisi et al. |
| 2015/0320564 A1 | 11/2015 | Parisi et al. |
| 2015/0359642 A1 | 12/2015 | Claypool et al. |
| 2016/0038294 A1 | 2/2016 | Parisi et al. |
| 2016/0045322 A1 | 2/2016 | Parisi et al. |
| 2016/0135959 A1 | 5/2016 | Sanford et al. |
| 2016/0158019 A1 | 6/2016 | Grey et al. |
| 2016/0184107 A1 | 6/2016 | Parisi et al. |
| 2016/0287397 A1 | 10/2016 | Wentorf et al. |
| 2016/0324647 A1 | 11/2016 | Claypool et al. |
| 2017/0079801 A1 | 3/2017 | Drury et al. |
| 2017/0143324 A1 | 5/2017 | Toler et al. |
| 2017/0156736 A1 | 6/2017 | Claypool et al. |
| 2018/0000601 A1 | 1/2018 | Sanford et al. |
| 2018/0000602 A1 | 1/2018 | Wentorf et al. |
| 2018/0000612 A1 | 1/2018 | Claypool et al. |
| 2018/0021143 A1 | 1/2018 | Parisi et al. |
| 2018/0021144 A1 | 1/2018 | Parisi et al. |
| 2018/0085225 A1 | 3/2018 | Wentorf et al. |
| 2018/0256346 A1 | 9/2018 | Byrd et al. |

FOREIGN PATENT DOCUMENTS

| | | |
|---|---|---|
| CA | 2190029 A1 | 11/1995 |
| CA | 2856070 C | 7/2016 |
| CH | 687584 A5 | 1/1997 |
| CN | 1087506 A | 6/1994 |
| CN | 1174498 A | 2/1998 |
| CN | 1179709 A | 4/1998 |
| CN | 1440262 A | 9/2003 |
| CN | 1549695 A | 11/2004 |
| CN | 2768715 Y | 4/2006 |
| CN | 1780594 A | 5/2006 |
| CN | 1874738 A | 12/2006 |
| CN | 101214175 A | 7/2008 |
| CN | 101222886 A | 7/2008 |
| CN | 101288597 A | 10/2008 |
| CN | 101347359 A | 1/2009 |
| CN | 201175391 Y | 1/2009 |
| CN | 101361684 A | 2/2009 |
| CN | 101401750 A | 4/2009 |
| CN | 101426453 A | 5/2009 |
| CN | 101522136 A | 9/2009 |
| CN | 101646392 A | 2/2010 |
| CN | 101658446 A | 3/2010 |

(56) References Cited

FOREIGN PATENT DOCUMENTS

| | | |
|---|---|---|
| CN | 101683289 A | 3/2010 |
| CN | 101711701 A | 5/2010 |
| CN | 101795643 A | 8/2010 |
| CN | 101835441 A | 9/2010 |
| CN | 102018584 A | 4/2011 |
| CN | 102048594 A | 5/2011 |
| CN | 102058448 A | 5/2011 |
| CN | 103118634 A | 5/2013 |
| CN | 103118635 A | 5/2013 |
| CN | 103118636 A | 5/2013 |
| CN | 103370025 A | 10/2013 |
| CN | 103379880 A | 10/2013 |
| CN | 104066402 A | 9/2014 |
| CN | 104093380 A | 10/2014 |
| CN | 104203160 A | 12/2014 |
| CN | 104379094 A | 2/2015 |
| CN | 104736105 A | 6/2015 |
| CN | 105055052 A | 11/2015 |
| CN | 105167889 A | 12/2015 |
| CN | 103118634 B | 8/2016 |
| CN | 103118636 B | 8/2016 |
| CN | 104093380 B | 8/2016 |
| CN | 103370025 B | 11/2016 |
| CN | 106073949 A | 11/2016 |
| CN | 106214292 A | 12/2016 |
| CN | 108135701 A | 6/2018 |
| EP | 0021421 A1 | 1/1981 |
| EP | 0327495 A2 | 8/1989 |
| EP | 0340919 A1 | 11/1989 |
| EP | 340919 A1 | 11/1989 |
| EP | 0372811 A1 | 6/1990 |
| EP | 0306744 B1 | 4/1992 |
| EP | 0495340 A1 | 7/1992 |
| EP | 0636353 A1 | 2/1995 |
| EP | 0672397 A1 | 9/1995 |
| EP | 0552950 B1 | 9/1996 |
| EP | 0536457 B1 | 1/1997 |
| EP | 0642328 B1 | 12/1998 |
| EP | 0592750 B1 | 1/1999 |
| EP | 0903125 A1 | 3/1999 |
| EP | 0956836 A1 | 11/1999 |
| EP | 0956836 B1 | 11/1999 |
| EP | 1025818 A2 | 8/2000 |
| EP | 1097679 A1 | 5/2001 |
| EP | 0709074 B1 | 12/2002 |
| EP | 1327424 A1 | 7/2003 |
| EP | 1378216 A2 | 1/2004 |
| EP | 1477143 A1 | 11/2004 |
| EP | 1568336 A1 | 8/2005 |
| EP | 1719478 A2 | 11/2006 |
| EP | 1722721 A1 | 11/2006 |
| EP | 1354571 B1 | 6/2007 |
| EP | 1396240 B1 | 4/2008 |
| EP | 1604623 B1 | 6/2008 |
| EP | 1996122 A1 | 12/2008 |
| EP | 0927009 B1 | 1/2009 |
| EP | 2011455 A1 | 1/2009 |
| EP | 1696835 B1 | 2/2009 |
| EP | 1132063 A2 | 9/2009 |
| EP | 1591082 B1 | 9/2009 |
| EP | 2140838 A2 | 1/2010 |
| EP | 2143403 A1 | 1/2010 |
| EP | 2237177 A1 | 10/2010 |
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| EP | 2595573 A1 | 5/2013 |
| EP | 2782525 A1 | 10/2014 |
| EP | 2830543 A1 | 2/2015 |
| EP | 2830544 A1 | 2/2015 |
| EP | 2830544 B1 | 9/2016 |
| EP | 2918235 B1 | 1/2017 |
| EP | 2595574 B1 | 5/2017 |
| FR | 2736819 A1 | 1/1997 |
| FR | 2747914 A1 | 10/1997 |
| FR | 2778332 A1 | 11/1999 |
| FR | 2788964 A1 | 8/2000 |
| FR | 2824260 A1 | 11/2002 |
| FR | 2852819 A1 | 10/2004 |
| FR | 2926719 A1 | 7/2009 |
| GB | 225347 A | 12/1924 |
| GB | 2253147 A | 9/1992 |
| GB | 2345446 A | 7/2000 |
| IN | 7145DELNP2014 A | 4/2015 |
| JP | 61247449 A | 11/1986 |
| JP | 62270153 A | 11/1987 |
| JP | 06203576 A | 7/1994 |
| JP | 09289998 A | 11/1997 |
| JP | 09511668 A | 11/1997 |
| JP | 2000000255 A | 1/2000 |
| JP | 2000245758 A | 9/2000 |
| JP | 2003516183 A | 5/2003 |
| JP | 2004166802 A | 6/2004 |
| JP | 2004254811 A | 9/2004 |
| JP | 3734270 B2 | 1/2006 |
| JP | 2007054488 A | 3/2007 |
| JP | 2007509709 A | 4/2007 |
| JP | 2007222616 A | 9/2007 |
| JP | 2009082713 A | 4/2009 |
| JP | 2009245619 A | 10/2009 |
| JP | 2010188051 A | 9/2010 |
| JP | 2010240406 A | 10/2010 |
| JP | 2011092738 A | 5/2011 |
| JP | 2012500667 A | 1/2012 |
| JP | 2012531265 A | 12/2012 |
| JP | 2015512307 A | 4/2013 |
| JP | 2013535276 A | 9/2013 |
| JP | 2013536005 A | 9/2013 |
| JP | 2013536006 A | 9/2013 |
| JP | 2013536007 A | 9/2013 |
| JP | 2014505517 A | 3/2014 |
| JP | 2014508554 A | 4/2014 |
| JP | 2014239900 A | 12/2014 |
| JP | 2015502203 A | 1/2015 |
| JP | 2015504333 A | 2/2015 |
| JP | 2015504759 A | 2/2015 |
| JP | 2015513966 A | 5/2015 |
| JP | 2015231566 A | 12/2015 |
| JP | 2016028729 A | 3/2016 |
| JP | 5980341 B2 | 8/2016 |
| JP | 2016195841 A | 11/2016 |
| JP | 2017221732 A | 12/2017 |
| WO | WO-9305729 A2 | 4/1993 |
| WO | WO-9409725 A1 | 5/1994 |
| WO | WO-9514444 A1 | 6/1995 |
| WO | WO-9514446 A1 | 6/1995 |
| WO | WO-9530389 A1 | 11/1995 |
| WO | WO-9535074 A1 | 12/1995 |
| WO | WO-9934755 A1 | 7/1999 |
| WO | WO-0141680 A1 | 6/2001 |
| WO | WO-200141680 A1 | 6/2001 |
| WO | WO-03099106 A2 | 12/2003 |
| WO | WO-2004058108 A1 | 7/2004 |
| WO | WO-2005037147 A1 | 4/2005 |
| WO | WO-2005051240 A1 | 6/2005 |
| WO | WO-2005122967 A1 | 12/2005 |
| WO | WO-2006058057 A2 | 6/2006 |
| WO | WO-2006092167 A1 | 9/2006 |
| WO | WO-2007108804 A1 | 9/2007 |
| WO | WO-2007109641 A2 | 9/2007 |
| WO | WO-2007119173 A2 | 10/2007 |
| WO | WO-2009029631 A1 | 3/2009 |
| WO | WO-2009088235 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO-2010001010 A1 | 1/2010 |
| WO | WO-2010008803 A2 | 1/2010 |
| WO | WO-2010011590 A1 | 1/2010 |
| WO | WO-2010022272 A1 | 2/2010 |
| WO | WO-2010023062 A2 | 3/2010 |

(56) References Cited

FOREIGN PATENT DOCUMENTS

| | | |
|---|---|---|
| WO | WO-2010045537 A1 | 4/2010 |
| WO | WO-2011043955 A1 | 4/2011 |
| WO | WO-2011063123 A2 | 5/2011 |
| WO | WO-2011071979 A2 | 6/2011 |
| WO | WO-2011072235 A2 | 6/2011 |
| WO | WO-2011110865 A2 | 9/2011 |
| WO | WO-2012004580 A1 | 1/2012 |
| WO | WO-2012018563 A1 | 2/2012 |
| WO | WO-2012018564 A1 | 2/2012 |
| WO | WO-2012018565 A1 | 2/2012 |
| WO | WO-2012018566 A1 | 2/2012 |
| WO | WO-2012018567 A1 | 2/2012 |
| WO | WO-2012020460 A1 | 2/2012 |
| WO | WO-2012082628 A1 | 6/2012 |
| WO | WO-2012083280 A1 | 6/2012 |
| WO | WO-2012112698 A2 | 8/2012 |
| WO | WO-2013013094 A1 | 1/2013 |
| WO | WO-2013074142 A1 | 5/2013 |
| WO | WO-2013074143 A1 | 5/2013 |
| WO | WO-2013074144 A1 | 5/2013 |
| WO | WO-2013074145 A1 | 5/2013 |
| WO | WO-2013077919 A1 | 5/2013 |
| WO | WO-2013115849 A1 | 8/2013 |
| WO | WO-2013148954 A1 | 10/2013 |
| WO | WO-2013148960 A1 | 10/2013 |
| WO | WO-2017053196 A1 | 3/2017 |
| WO | WO-2018165442 A1 | 9/2018 |

OTHER PUBLICATIONS

"U.S. Appl. No. 13/087,610, Notice of Allowance dated Jun. 28, 2013", 6 pgs.
"U.S. Appl. No. 13/087,610, Notice of Allowance dated Oct. 8, 2013", 7 pgs.
"U.S. Appl. No. 13/087,610, Response filed May 24, 2013 to Non Final Office Action dated Feb. 26, 2013", 15 pgs.
"U.S. Appl. No. 13/459,037, Final Office Action dated Sep. 23, 2013", 9 pgs.
"U.S. Appl. No. 13/459,037, Non Final Office Action dated Apr. 23, 2013", 10 pgs.
"U.S. Appl. No. 13/459,037, Notice of Allowance dated Jun. 13, 2014", 9 pgs.
"U.S. Appl. No. 13/459,037, Preliminary Amendment filed Apr. 27, 2012", 3 pgs.
"U.S. Appl. No. 13/459,037, Response filed Mar. 21, 2014 to Final Office Action dated Sep. 23, 2013", 15 pgs.
"U.S. Appl. No. 13/459,037, Response filed Mar. 28, 2013 to Restriction Requirement dated Feb. 26, 2013", 9 pgs.
"U.S. Appl. No. 13/459,037, Response filed Jul. 23, 2013 to Non Final Office Action dated Apr. 23, 2013", 19 pgs.
"U.S. Appl. No. 13/459,037, Restriction Requirement dated Feb. 26, 2013", 6 pgs.
"U.S. Appl. No. 13/459,041, Non Final Office Action dated Jan. 15, 2014", 16 pgs.
"U.S. Appl. No. 13/459,041, Non Final Office Action dated Sep. 9, 2014", 14 pgs.
"U.S. Appl. No. 13/459,041, Notice of Allowance dated Apr. 2, 2015", 10 pgs.
"U.S. Appl. No. 13/459,041, Preliminary Amendment dated Apr. 27, 2012", 7 pgs.
"U.S. Appl. No. 13/459,041, PTO Response to Rule 312 Communication dated Jun. 9, 2015", 2 pgs.
"U.S. Appl. No. 13/459,041, Response filed May 15, 2014 to Non-Final Office Action dated Jan. 15, 2014", 24 pgs.
"U.S. Appl. No. 13/459,041, Response filed Sep. 23, 2013 to Restriction Requirement dated Jul. 25, 2013", 18 pgs.
"U.S. Appl. No. 13/459,041, Response filed Dec. 9, 2014 to Non-Final Office Action dated Sep. 9, 2014", 23 pgs.
"U.S. Appl. No. 13/459,041, Restriction Requirement dated Jul. 25, 2013", 9 pgs.

"U.S. Appl. No. 13/459,048, Non Final Office Action dated Jul. 11, 2013", 6 pgs.
"U.S. Appl. No. 13/459,048, Notice of Allowance dated Nov. 26, 2013", 10 pgs.
"U.S. Appl. No. 13/459,048, Preliminary Amendment filed Apr. 27, 2012", 7 pgs.
"U.S. Appl. No. 13/459,048, Response filed Nov. 11, 2013 to Non-Final Office Action dated Jul. 11, 2013", 16 pgs.
"U.S. Appl. No. 13/459,056, Examiner Interview Summary dated Dec. 26, 2013", 3 pgs.
"U.S. Appl. No. 13/459,056, Non Final Office Action dated Jul. 25, 2013", 11 pgs.
"U.S. Appl. No. 13/459,056, Notice of Allowance dated Feb. 20, 2014", 5 pgs.
"U.S. Appl. No. 13/459,056, Preliminary Amendment filed Apr. 27, 2012", 7 pgs.
"U.S. Appl. No. 13/459,056, PTO Response to Rule 312 Communication dated May 22, 2014", 2 pgs.
"U.S. Appl. No. 13/459,056, Response filed Jan. 24, 2014 to Non-Final Office Action dated Jul. 25, 2013", 27 pgs.
"U.S. Appl. No. 13/459,056, Response filed Apr. 8, 2013 to Restriction Requirement dated Mar. 6, 2013", 15 pgs.
"U.S. Appl. No. 13/459,056, Restriction Requirement dated Mar. 6, 2013", 6 pgs.
"U.S. Appl. No. 13/819,116, Advisory Action dated Jan. 5, 2016", 3 pgs.
"U.S. Appl. No. 13/819,116, Corrected Notice of Allowance dated Oct. 21, 2016", 2 pgs.
"U.S. Appl. No. 13/819,116, Examiner Interview Summary dated Apr. 18, 2016", 11 pgs.
"U.S. Appl. No. 13/819,116, Final Office Action dated Jul. 26, 2016", 6 pgs.
"U.S. Appl. No. 13/819,116, Final Office Action dated Oct. 21, 2015", 15 pgs.
"U.S. Appl. No. 13/819,116, Non Final Office Action dated Feb. 17, 2016", 15 pgs.
"U.S. Appl. No. 13/819,116, Non Final Office Action dated Jun. 2, 2015", 14 pgs.
"U.S. Appl. No. 13/819,116, Notice of Allowance dated Sep. 29, 2016", 5 pgs.
"U.S. Appl. No. 13/819,116, Preliminary Amendment filed Feb. 26, 2013", 8 pgs.
"U.S. Appl. No. 13/819,116, Response filed Mar. 27, 2015 to Restriction Requirement dated Feb. 12, 2015", 11 pgs.
"U.S. Appl. No. 13/819,116, Response filed Apr. 29, 2016 to Non Final Office Action dated Feb. 17, 2016", 17 pgs.
"U.S. Appl. No. 13/819,116, Response filed Jul. 16, 2015 to Non Final Office Action dated Jun. 2, 2015", 22 pgs.
"U.S. Appl. No. 13/819,116, Response filed Sep. 14, 2016 Final Office Action dated Jul. 26, 2016", 10 pgs.
"U.S. Appl. No. 13/819,116, Response filed Dec. 15, 2015 to Final Office Action dated Oct. 21, 2015", 16 pgs.
"U.S. Appl. No. 13/819,116, Restriction Requirement dated Feb. 12, 2015", 7 pgs.
"U.S. Appl. No. 13/836,586, Express Abandonment filed May 30, 2014", 1 pg.
"U.S. Appl. No. 13/836,665, Examiner Interview Summary dated Jul. 7, 2014", 4 pgs.
"U.S. Appl. No. 13/836,665, Final Office Action dated Jul. 25, 2014", 25 pgs.
"U.S. Appl. No. 13/836,665, Non Final Office Action dated Jan. 30, 2014", 21 pgs.
"U.S. Appl. No. 13/836,665, Notice of Allowance dated Jun. 9, 2015", 10 pgs.
"U.S. Appl. No. 13/836,665, Response filed Jan. 23, 2015 to Final Office Action dated Jul. 25, 2014", 25 pgs.
"U.S. Appl. No. 13/836,665, Response filed May 30, 2014 to Non-Final Office Action dated Jan. 30, 2014", 21 pgs.
"U.S. Appl. No. 13/837,294, Final Office Action dated Apr. 25, 2016", 7 pgs.
"U.S. Appl. No. 13/837,294, Final Office Action dated Jun. 2, 2016", 7 pgs.

(56) References Cited

OTHER PUBLICATIONS

"U.S. Appl. No. 13/837,294, Non Final Office Action dated Dec. 10, 2015", 8 pgs.
"U.S. Appl. No. 13/837,294, Notice of Allowance dated Aug. 25, 2016", 5 pgs.
"U.S. Appl. No. 13/837,294, Response filed Mar. 4, 2016 to Non Final Office Action dated Dec. 10, 2015", 16 pgs.
"U.S. Appl. No. 13/837,294, Response filed Aug. 3, 2016 to Final Office Action dated Jun. 2, 2016", 7 pgs.
"U.S. Appl. No. 13/837,294, Response filed Oct. 12, 2015 to Restriction Requirement dated Aug. 24, 2015", 9 pgs.
"U.S. Appl. No. 13/837,294, Restriction Requirement dated Aug. 24, 2015", 6 pgs.
"U.S. Appl. No. 13/837,774, Examiner Interview Summary dated Jul. 22, 2014", 4 pgs.
"U.S. Appl. No. 13/837,774, Final Office Action dated Mar. 17, 2016", 14 pgs.
"U.S. Appl. No. 13/837,774, Final Office Action dated Jul. 28, 2014", 17 pgs.
"U.S. Appl. No. 13/837,774, Non Final Office Action dated Feb. 10, 2014", 33 pgs.
"U.S. Appl. No. 13/837,774, Non Final Office Action dated Sep. 18, 2015", 16 pgs.
"U.S. Appl. No. 13/837,774, Response filed Jan. 28, 2015 to Final Office Action dated Sep. 28, 2014", 16 pgs.
"U.S. Appl. No. 13/837,774, Response filed Jun. 10, 2014 to Non-Final Office Action dated Feb. 20, 2014", 29 pgs.
"U.S. Appl. No. 13/837,774, Response filed Jul. 7, 2015 to Restriction Requirement dated May 20, 2015", 10 pgs.
"U.S. Appl. No. 13/837,774, Response filed Dec. 16, 2015 to Non Final Office Action dated Sep. 18, 2015", 17 pgs.
"U.S. Appl. No. 13/837,774, Restriction Requirement dated May 20, 2015", 6 pgs.
"U.S. Appl. No. 14/034,076, Appeal Brief filed Apr. 18, 2016", 21 pgs.
"U.S. Appl. No. 14/034,076, Final Office Action dated Dec. 21, 2015", 11 pgs.
"U.S. Appl. No. 14/034,076, Non Final Office Action dated Jun. 24, 2015", 11 pgs.
"U.S. Appl. No. 14/034,076, Notice of Allowance dated Oct. 28, 2016", 7 pgs.
"U.S. Appl. No. 14/034,076, Response filed Nov. 16, 2015 to Non Final Office Action dated Jun. 24, 2015", 13 pgs.
"U.S. Appl. No. 14/034,937, PTO Response to Rule 312 Communication dated Oct. 10, 2017", 2 pgs.
"U.S. Appl. No. 14/063,032, Non Final Office Action dated Jun. 20, 2014", 6 pgs.
"U.S. Appl. No. 14/063,032, Notice of Allowance dated Dec. 19, 2014", 6 pgs.
"U.S. Appl. No. 14/063,032, Preliminary Amendment filed Oct. 25, 2013", 3 pgs.
"U.S. Appl. No. 14/063,032, Response filed Oct. 20, 2014 to Non-Final Office Action dated Jun. 20, 2014", 9 pgs.
"U.S. Appl. No. 14/181,033, Non Final Office Action dated May 1, 2015", 5 pgs.
"U.S. Appl. No. 14/181,033, Notice of Allowance dated Jul. 17, 2015", 10 pgs.
"U.S. Appl. No. 14/181,033, Response filed Jun. 22, 2015 to Non-Final Office Action dated May 1, 2015", 11 pgs.
"U.S. Appl. No. 14/284,028, Non Final Office Action dated Jul. 7, 2015", 17 pgs.
"U.S. Appl. No. 14/284,028, Notice of Allowance dated Nov. 6, 2015", 5 pgs.
"U.S. Appl. No. 14/284,028, Response filed Oct. 6, 2015 to Non Final Office Action dated Jul. 7, 2015", 15 pgs.
"U.S. Appl. No. 14/284,028, Supplemental Notice of Allowability dated Feb. 26, 2016", 5 pgs.
"U.S. Appl. No. 14/284,028, Supplemental Preliminary Amendment filed Jul. 8, 2014", 13 pgs.
"U.S. Appl. No. 14/304,009, Notice of Allowance dated Nov. 16, 2016", 7 pgs.
"U.S. Appl. No. 14/304,009, Preliminary Amendment filed Jul. 31, 2014", 7 pgs.
"U.S. Appl. No. 14/490,153, Final Office Action dated Apr. 15, 2015", 18 pgs.
"U.S. Appl. No. 14/490,153, Non Final Office Action dated Nov. 12, 2014", 9 pgs.
"U.S. Appl. No. 14/490,153, Notice of Allowance dated Aug. 14, 2015", 10 pgs.
"U.S. Appl. No. 14/490,153, Preliminary Amendment filed Sep. 18, 2014", 3 pgs.
"U.S. Appl. No. 14/490,153, Response filed Feb. 18, 2015 to Non-Final Office Action dated Nov. 12, 2014", 14 pgs.
"U.S. Appl. No. 14/490,153, Response filed Jul. 7, 2015 to Final Office Action dated Apr. 15, 2015", 14 pgs.
"U.S. Appl. No. 14/660,217, Corrected Notice of Allowance dated May 26, 2016", 3 pgs.
"U.S. Appl. No. 14/660,217, Non Final Office Action dated Dec. 17, 2015", 8 pgs.
"U.S. Appl. No. 14/660,217, Notice of Allowance dated Apr. 26, 2016", 5 pgs.
"U.S. Appl. No. 14/660,217, Preliminary Amendment filed Mar. 18, 2015", 9 pgs.
"U.S. Appl. No. 14/660,217, Response filed Mar. 23, 2016 to Non Final Office Action dated Dec. 17, 2015", 14 pgs.
"U.S. Appl. No. 14/740,690, Non Final Office Action dated Dec. 7, 2016", 19 pgs.
"U.S. Appl. No. 14/740,690, Notice of Allowability dated Aug. 29, 2017", 2 pgs.
"U.S. Appl. No. 14/740,690, Notice of Allowance dated Jun. 13, 2017", 9 pgs.
"U.S. Appl. No. 14/740,690, Response filed Mar. 3, 2017 to Non Final Office Action dated Dec. 7, 2016", 14 pgs.
"U.S. Appl. No. 14/833,385, Examiner Interview Summary dated Dec. 27, 2017", 3 pgs.
"U.S. Appl. No. 14/833,385, Final Office Action dated Nov. 13, 2017", 9 pgs.
"U.S. Appl. No. 14/833,385, Non Final Office Action dated Jun. 19, 2017", 10 pgs.
"U.S. Appl. No. 14/833,385, Preliminary Amendment filed Aug. 25, 2015", 6 pgs.
"U.S. Appl. No. 14/833,385, Response filed May 12, 2017 to Restriction Requirement dated Mar. 17, 2017", 8 pgs.
"U.S. Appl. No. 14/833,385, Response filed Sep. 18, 2017 to Non Final Office Action dated Jun. 19, 2017", 14 pgs.
"U.S. Appl. No. 14/833,385, Restriction Requirement dated Mar. 17, 2017", 6 pgs.
"U.S. Appl. No. 14/918,721, Final Office Action dated Oct. 20, 2016", 5 pgs.
"U.S. Appl. No. 14/918,721, Non Final Office Action dated Jun. 16, 2016", 6 pgs.
"U.S. Appl. No. 14/918,721, Notice of Allowance dated Feb. 1, 2017", 9 pgs.
"U.S. Appl. No. 14/918,721, Preliminary Amendment filed Oct. 23, 2015", 8 pgs.
"U.S. Appl. No. 14/918,721, PTO Response to Rule 312 Communication dated Mar. 17, 2017", 2 pgs.
"U.S. Appl. No. 14/918,721, Response filed Sep. 12, 2016 to Non Final Office Action dated Jun. 16, 2016", 12 pgs.
"U.S. Appl. No. 14/918,721, Response filed Dec. 13, 2016 to Final Office Action dated Oct. 20, 2016", 9 pgs.
"U.S. Appl. No. 14/926,281, Non Final Office Action dated Jun. 21, 2017", 17 pgs.
"U.S. Appl. No. 14/926,281, Notice of Allowance dated Nov. 16, 2017", 9 pgs.
"U.S. Appl. No. 14/926,281, Preliminary Amendment filed Oct. 30, 2015", 8 pgs.
"U.S. Appl. No. 14/926,281, Response filed Sep. 18, 2017 to Non Final Office Action dated Jun. 21, 2017", 11 pgs.
"U.S. Appl. No. 15/003,091, Notice of Allowance dated Nov. 6, 2017", 8 pgs.

(56) References Cited

OTHER PUBLICATIONS

"U.S. Appl. No. 15/003,091, PTO Response to Rule 312 Communication dated Jan. 23, 2018", 2 pgs.
"U.S. Appl. No. 15/062,252, Preliminary Amendment filed Mar. 9, 2016", 8 pgs.
"U.S. Appl. No. 15/062,262, Non Final Office Action dated Jul. 22, 2016", 12 pgs.
"U.S. Appl. No. 15/062,262, Notice of Allowance dated Jan. 31, 2017", 5 pgs.
"U.S. Appl. No. 15/062,262, PTO Response to Rule 312 Communication dated Mar. 7, 2017", 2 pgs.
"U.S. Appl. No. 15/062,262, Response filed Oct. 24, 2016 to Non Final Office Action dated Jul. 22, 2016", 13 pgs.
"U.S. Appl. No. 15/211,812, Non Final Office Action dated Jan. 27, 2017", 5 pgs.
"U.S. Appl. No. 15/211,812, Notice of Allowance dated May 31, 2017", 5 pgs.
"U.S. Appl. No. 15/211,812, Preliminary Amendment filed Sep. 8, 2016", 8 pgs.
"U.S. Appl. No. 15/211,812, Response filed Apr. 19, 2017 to Non Final Office Action dated Jan. 27, 2017", 9 pgs.
"U.S. Appl. No. 15/267,793, Restriction Requirement dated Feb. 16, 2018", 7 pgs.
"U.S. Appl. No. 15/424,328, Non Final Office Action dated Jun. 23, 2017", 5 pgs.
"U.S. Appl. No. 15/424,328, Notice of Allowance dated Oct. 16, 2017", 6 pgs.
"U.S. Appl. No. 15/424,328, Preliminary Amendment filed Feb. 28, 2017", 10 pgs.
"U.S. Appl. No. 15/424,328, Response filed Sep. 20, 2017 to Non Final Office Action dated Jun. 23, 2017", 9 pgs.
"U.S. Appl. No. 15/435,620, Final Office Action dated Dec. 15, 2017", 9 pgs.
"U.S. Appl. No. 15/435,620, Non Final Office Action dated Jul. 26, 2017", 10 pgs.
"U.S. Appl. No. 15/435,620, Preliminary Amendment filed Mar. 20, 2017", 7 pgs.
"U.S. Appl. No. 15/435,620, Response filed Feb. 12, 2018 to Final Office Action dated Dec. 15, 2017", 9 pgs.
"U.S. Appl. No. 15/435,620, Response filed Oct. 25, 2017 to Non Final Office Action dated Jul. 26, 2017", 13 pgs.
"U.S. Appl. No. 15/703,698, Preliminary Amendment filed Sep. 28, 2017", 8 pgs.
"U.S. Appl. No. 15/703,713, Non Final Office Action dated Mar. 27, 2018", 29 pgs.
"U.S. Appl. No. 15/720,866, Response filed Nov. 13, 2017 to Non Final Office Action dated Sep. 14, 2017", 10 pgs.
"U.S. Appl. No. 15/720,866, Preliminary Amendment filed Nov. 13, 2017", 9 pgs.
"U.S. Appl. No. 15/827,654, Preliminary Amendment filed Dec. 22, 2017", 11 pgs.
"Australian Application Serial No. 2011343440, First Examiner Report dated Feb. 17, 2014", 3 pgs.
"Australian Application Serial No. 2011343440, Response filed Mar. 21, 2014 to Office Action dated Feb. 17, 2014", 1 pg.
"Australian Application Serial No. 2013238046, First Examiner Report dated Nov. 26, 2015", 2 pgs.
"Australian Application Serial No. 2013238046, Response filed Feb. 2, 2016 to First Examiner Report dated Nov. 26, 2015", 1 pg.
"Australian Application Serial No. 2013238054, First Examiner Report dated Oct. 17, 2016", 4 pgs.
"Australian Application Serial No. 2013238054, Response filed Jan. 18, 2017 to First Examiner Report dated Oct. 17, 2016", 9 pgs.
"Australian Application Serial No. 2015238820, First Examination Report dated May 30, 2017", 3 pgs.
"Australian Application Serial No. 2015238820, Response filed Jul. 12, 2017 to First Examination Report dated May 30, 2017", 12 pgs.
"Australian Application Serial No. 2017251736, First Examiners Report dated Oct. 31, 2017", 2 pgs.
"Canadian Application Serial No. 2,806,326, Office Action dated Feb. 8, 2018", 4 pgs.
"Canadian Application Serial No. 2,821,927, Voluntary Amendment dated Jun. 14, 2013", 7 pgs.
"Canadian Application Serial No. 2,824,527, Office Action dated Mar. 17, 2014", 2 pgs.
"Canadian Application Serial No. 2,824,527, Response filed Sep. 17, 2014 to Office Action dated Mar. 17, 2017-14", 14 pgs.
"Canadian Application Serial No. 2,856,070, Preliminary Amendment filed May 25, 2015", 27 pgs.
"Canadian Application Serial No. 2,956,119, Office Action dated Jan. 22, 2018", 3 pgs.
"Chinese Application Serial No. 201180067430.X, Office Action dated Aug. 28, 2014", (W/English Translation), 8 pgs.
"Chinese Application Serial No. 201180067430.X, Response filed Jan. 4, 2015 to Office Action dated Sep. 26, 2014", (W/ English Translation), 14 pgs.
"Chinese Application Serial No. 201180067757.7, Office Action dated Mar. 2, 2015", (W/English Translation), 18 pgs.
"Chinese Application Serial No. 201180067757.7, Office Action dated Jun. 1, 2016", (W/English Translation), 10 pgs.
"Chinese Application Serial No. 201180067757.7, Office Action dated Nov. 16, 2015", (W/English Translation), 17 pgs.
"Chinese Application Serial No. 201180067757.7, Response filed Jan. 27, 2016 to Office Action dated Nov. 16, 2015", (W/ English Translation of Claims), 12 pgs.
"Chinese Application Serial No. 201180067757.7, Response filed Jul. 10, 2015 to Office Action dated Mar. 2, 2015", (W/ English Translation), 13 pgs.
"Chinese Application Serial No. 201180067757.7, Response filed Aug. 11, 2016 to Office Action dated Jun. 1, 2016", (W/ English Translation of Claims), 9 pgs.
"Chinese Application Serial No. 201180067757.7, Voluntary Amendment dated Feb. 14, 2014", (W/ English Translation of Claims), 8 pgs.
"Chinese Application Serial No. 201280067481.7, Office Action dated Sep. 30, 2015", (W/English Translation), 7 pgs.
"Chinese Application Serial No. 201380028572.4, Office Action dated Aug. 13, 2015", (W/English Translation), 16 pgs.
"Chinese Application Serial No. 201380028683.5, Office Action dated Jun. 27, 2016", (W/English Translation), 8 pgs.
"Chinese Application Serial No. 201380028683.5, Office Action dated Nov. 4, 2015", (W/English Translation), 16 pgs.
"Chinese Application Serial No. 201380028683.5, Office Action dated Dec. 30, 2016", (W/English Translation), 4 pgs.
"Chinese Application Serial No. 201380028683.5, Response filed Feb. 8, 2017 to Office Action dated Dec. 30, 2016", (W/ English Translation), 13 pgs.
"Chinese Application Serial No. 201380028683.5, Response filed Mar. 18, 2016 to Office Action dated Nov. 4, 2015", (W/ English Translation of Claims), 11 pgs.
"Chinese Application Serial No. 201380028683.5, Response filed Sep. 6, 2016 to Office Action dated Jun. 27, 2016", (W/ English Translation of Claims), 11 pgs.
"Chinese Application Serial No. 201510394094.X, Office Action dated May 24, 2017", (W/English Translation), 11 pgs.
"Chinese Application Serial No. 201510394094.X, Office Action dated Aug. 30, 2016", (W/English Translation), 14 pgs.
"Chinese Application Serial No. 201510394094.X, Office Action dated Nov. 3, 2017", (W/English Translation), 10 pgs.
"Chinese Application SerialNo. 201510394094.X, Response filed Jan. 16, 2017 to Office Action dated Aug. 30, 2016", (W/ English Translation of Claims), 11 pgs.
"Chinese Application Serial No. 201510394094.X, Response filed Jan. 18, 2018 to Office Action dated Nov. 3, 2017", (W/ English Claims), 10 pgs.
"Chinese Application Serial No. 201510394094.X, Response filed Jul. 10, 2017 to Office Action dated May 24, 2017", (W/ English Translation), 10 pgs.
"Chinese Application Serial No. 201610634595.5, Response filed Nov. 3, 2017 to Office Action dated Jun. 21, 2017", w/English Claims, 8 pgs.

(56) References Cited

OTHER PUBLICATIONS

"Chinese Application Serial No. 201610685172.6, Office Action dated Sep. 28, 2017", (W/English Translation), 9 pgs.
"Chinese Application Serial No. 201610685172.6, Response filed Dec. 13, 2017 to Office Action dated Sep. 28, 2017", (W/ English Claims), 13 pgs.
"Complete Knee Solution Surgical Technique for the CR-Flex Fixed Bearing Knee", Zimmer Nexgen, (2003), 22 pgs.
"European Application Serial No. 11802835.6, Communication Pursuant to Article 94(3) EPC dated Dec. 11, 2017", 4 pgs.
"European Application Serial No. 11808493.8, Communication Pursuant to Article 94(3) EPC dated Dec. 7, 2015", 4 pgs.
"European Application Serial No. 11808493.8, Examination Notification Art. 94(3) dated Feb. 20, 2015", 6 pgs.
"European Application Serial No. 11808493.8, Response filed Feb. 26, 2014 to Communication pursuant to Rules 161(1) and 162 EPC dated Aug. 16, 2013", 14 pgs.
"European Application Serial No. 11808493.8, Response filed Apr. 18, 2016 to Communication Pursuant to Article 94(3) EPC dated Dec. 7, 2015", 15 pgs.
"European Application Serial No. 11808493.8, Response filed Jul. 2, 2015 to Examination Notification Art. 94(3) dated Feb. 20, 2015", 13 pgs.
"European Application Serial No. 12718882.9, Communication Pursuant to Article 94(3) EPC dated Dec. 1, 2015", 11 pgs.
"European Application Serial No. 12718882.9, Response filed Feb. 10, 2015 to Communication Pursuant to Rules 161(1) and 162 EPC dated Jul. 31, 2014", 11 pgs.
"European Application Serial No. 12718882.9, Response filed Apr. 11, 2016 to Communication Pursuant to Article 94(3) EPC dated Dec. 1, 2015", 12 pgs.
"European Application Serial No. 12718883.7, Communication Pursuant to Article 94(3) EPC dated Dec. 2, 2015", 4 pgs.
"European Application Serial No. 12718883.7, Communication Pursuant to Rules 161(1) and 162 EPC dated Jul. 31, 2014", 2 pgs.
"European Application Serial No. 12718883.7, Intention to Grant dated May 20, 2016", 5 pgs.
"European Application Serial No. 12718883.7, Response filed Feb. 10, 2015 to Communication Pursuant to Rules 161(1) and 162 ECP dated Jul. 31, 2014", 16 pgs.
"European Application Serial No. 12718883.7, Response filed Apr. 12, 2016 to Communication Pursuant to Article 94(3) EPC dated Dec. 2, 2015", 30 pgs.
"European Application Serial No. 12719236.7 Response filed Feb. 9, 2015 to Communication Pursuant to Rules 161(1) and 162 EPC dated Jul. 30, 2014", 10 pgs.
"European Application Serial No. 12719236.7, Decision to Grant dated Feb. 18, 2016", 3 pgs.
"European Application Serial No. 12719236.7, Office Action dated Aug. 27, 2015", 7 pgs.
"European Application Serial No. 12720352.9 Response filed Feb. 9, 2015 to Communication Pursuant to Rules 161(1) and 162 EPC dated Jul. 30, 2014", 10 pgs.
"European Application Serial No. 13716636.9, Communication Pursuant to Article 94(3) EPC dated Nov. 16, 2015", 4 pgs.
"European Application Serial No. 13716636.9, Communication Pursuant to Article 94(3) EPC dated Nov. 17, 2016", 4 pgs.
"European Application Serial No. 13716636.9, Communication Pursuant to Article 94(3) EPC dated Jun. 6, 2016", 5 pgs.
"European Application Serial No. 13716636.9, Communication pursuant to Rules 161(1) and 162 EPC dated Dec. 12, 2014", 2 pgs.
"European Application Serial No. 13716636.9, Response filed Mar. 24, 2016 to Communication Pursuant to Article 94(3) EPC dated Nov. 16, 2015", 18 pgs.
"European Application Serial No. 13716636.9, Response filed Mar. 27, 2017 to Communication Pursuant to Article 94(3) EPC dated Nov. 17, 2016", 15 pgs.
"European Application Serial No. 13716636.9, Response filed Jun. 22, 2015 to Communication pursuant to Rules 161(1) and 162 EPC dated Dec. 12, 2014", 10 pgs.
"European Application Serial No. 13716636.9, Response filed Oct. 17, 2016 to Communication Pursuant to Article 94(3) EPC dated Jun. 6, 2016", 5 pgs.
"European Application Serial No. 14190180.1, Extended European Search Report dated Sep. 24, 2015", 8 pgs.
"European Application Serial No. 15191781.2, Communication Pursuant to Article 94(3) EPC dated Jan. 8, 2018", 4 pgs.
"European Application Serial No. 16156228.5, Extended European Search Report dated May 11, 2017", 5 pgs.
"European Application Serial No. 16183635.8, Extended European Search Report dated Jun. 30, 2017", 9 pgs.
"European Application Serial No. 16189084.3, Extended European Search Report dated Oct. 9, 2017", 9 pgs.
"Gender Solutions Natural Knee Flex System: Because Men and Women are Different", Zimmer, Inc., (2007, 2009), 6 pg.
"Gender Solutions Natural Knee Flex System: Surgical Technique", Zimmer, Inc., (2007, 2008, 2009), 36 pgs.
"International Application Serial No. PCT/US2011/064435, International Preliminary Report on Patentability dated Jun. 27, 2013", 9 pgs.
"International Application Serial No. PCT/US2011/064435, Search Report dated Jun. 21, 2012", 5 pgs.
"International Application Serial No. PCT/US2011/064435, Written Opinion dated Jun. 21, 2012", 7 pgs.
"International Application Serial No. PCT/US2011/065683, International Preliminary Report on Patentability dated Jun. 27, 2013", 11 pgs.
"International Application Serial No. PCT/US2011/065683, International Search Report dated Apr. 24, 2012", 12 pgs.
"International Application Serial No. PCT/US2011/065683, Written Opinion dated Apr. 24, 2012", 10 pgs.
"International Application Serial No. PCT/US2012/035679, International Preliminary Report on Patentability dated May 30, 2014", 8 pgs.
"International Application Serial No. PCT/US2012/035679, International Search Report dated Jun. 8, 2012", 4 pgs.
"International Application Serial No. PCT/US2012/035679, Written Opinion dated Jun. 8, 2012", 7 pgs.
"International Application Serial No. PCT/US2012/035680, International Preliminary Report on Patentability dated May 30, 2014", 13 pgs.
"International Application Serial No. PCT/US2012/035680, Search Report dated Oct. 9, 2012", 7 pgs.
"International Application Serial No. PCT/US2012/035680, Written Opinion dated Oct. 9, 2012", 11 pgs.
"International Application Serial No. PCT/US2012/035683, International Preliminary Report on Patentability dated May 30, 2014", 9 pgs.
"International Application Serial No. PCT/US2012/035683, International Search Report and Written Opinion dated Jun. 5, 2012", 12 pgs.
"International Application Serial No. PCT/US2012/035684, International Preliminary Report on Patentability dated May 30, 2014", 14 pgs.
"International Application Serial No. PCT/US2012/035684, International Search Report dated Aug. 8, 2012", 9 pgs.
"International Application Serial No. PCT/US2012/035684, Written Opinion dated Jun. 8, 2012", 12 pgs.
"International Application Serial No. PCT/US2013/034286, International Preliminary Report on Patentability dated Oct. 9, 2014", 8 pgs.
"International Application Serial No. PCT/US2013/034286, International Search Report dated Jun. 25, 2013", 6 pgs.
"International Application Serial No. PCT/US2013/034286, Written Opinion dated Jun. 25, 2013", 6 pgs.
"International Application Serial No. PCT/US2013/034293, International Preliminary Report on Patentability dated Oct. 9, 2014", 9 pgs.
"International Application Serial No. PCT/US2013/034293, International Search Report dated Jun. 25, 2013", 6 pgs.
"International Application Serial No. PCT/US2013/034293, Written Opinion dated Jun. 25, 2013", 7 pgs.

(56) References Cited

OTHER PUBLICATIONS

"International Application Serial No. PCT/US2016/052163, International Search Report dated Jan. 20, 2017", 7 pgs.
"International Application Serial No. PCT/US2016/052163, Invitation to Pay Add'l Fees and Partial Search Report dated Nov. 7, 2016", 7 pgs.
"International Application Serial No. PCT/US2016/052163, Written Opinion dated Jan. 20, 2017", 8 pgs.
"Intramedullary Instrumentation Surgical Technique for the NexGen Cruciate Retaining & Legacy Posterior Stabilized Knee", Zimmer, Inc. Nexgen Complete Knee Solution, 97-5973-102, Rev. 1, (1995,1997,1998), 36 pgs.
"Japanese Application Serial No. 2013-544655, Office Action dated Mar. 8, 2016", (W/ English Translation), 8 pgs.
"Japanese Application Serial No. 2013-544655, Office Action dated Sep. 29, 2015", (W/ English Translation), 7 pgs.
"Japanese Application Serial No. 2013-544655, Response filed Jan. 4, 2016 to Office Action dated Sep. 29, 2015", (English Translation of Claims), 14 pgs.
"Japanese Application Serial No. 2013-544655, Response filed Jul. 14, 2016 to Office Action dated Mar. 8, 2016", (w/ English Translation of Claims), 13 pgs.
"Japanese Application Serial No. 2013-544858, Request for Examination filed Feb. 4, 2014", (With English Translation), 14 pgs.
"Japanese Application Serial No. 2014-121515, Notice of Reasons for Rejection dated Jan. 5, 2016", (W/ English Translation), 9 pgs.
"Japanese Application Serial No. 2014-121515, Office Action dated Jun. 2, 2015", (W/ English Translation), 10 pgs.
"Japanese Application Serial No. 2014-121515, Response filed May 11, 2016 to Notice of Reasons for Rejection dated Jan. 5, 2016", (W/ English Translation of Claims), 11 pgs.
"Japanese Application Serial No. 2014-121515, Response filed Aug. 20, 2015 to Office Action dated Jun. 2, 2015", (W/ English Translation of Claims), 6 pgs.
"Japanese Application Serial No. 2014-542297, Office Action dated May 31, 2016", (W/ English Translation of Claims), 6 pgs.
"Japanese Application Serial No. 2014-542297, Office Action dated Jun. 30, 2015", (W/ English Translation), 10 pgs.
"Japanese Application Serial No. 2014-542297, Office Action dated Nov. 24, 2015", (W/ English Translation), 10 pgs.
"Japanese Application Serial No. 2014-542297, Response filed Feb. 23, 2016 to Office Action dated Nov. 24, 2015", (W/ English Translation of Claims), 15 pgs.
"Japanese Application Serial No. 2014-542297, Response filed Jun. 8, 2016 to Office Action dated May 31, 2016", (W/ English Translation of Claims), 14 pgs.
"Japanese Application Serial No. 2014-542297, Response filed Sep. 28, 2015 to Office Action dated Jun. 30, 2015", (W/ English Translation of Claims), 16 pgs.
"Japanese Application Serial No. 2015-503563, Office Action dated Dec. 20, 2016", (W/ English Translation), 10 pgs.
"Japanese Application Serial No. 2015-503563, Response Filed Mar. 13, 2017 to Office Action dated Dec. 20, 2016", (W/ English Translation), 9 pgs.
"Japanese Application Serial No. 2016-145390, Office Action dated Apr. 25, 2017", (W/ English Translation), 5 pgs.
"Japanese Application Serial No. 2016-145390, Response filed Jul. 3, 2017 to Office Action dated Apr. 25, 2017", (W/ English Translation of Claims), 16 pgs.
"Legacy Implant Options", Nexgen Complete Knee Solution, (2002), 8 pgs.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Multi-Reference 4-in-1 Femoral Instrumentation Surgical Technique for NexGen Cruciate Retaining & NexGen Legacy Posterior Stabilized Knees", Zimmer, Inc. Nexgen Complete Knee Solution, 97-5973-402 Rev. 1, (1998, 2000), 18 pgs.
"Natural-Knee II Primary System Surgical Technique", Zimmer, Inc., (2005), 48 pgs.

"Nexgen Complete Knee Solution for the Legacy Knee LPS-Flex Fixed Bearing Knee", Zimmer Surgical Technique, 97-5964-102-00, (2004, 2007), 12 pgs.
"NexGen Complete Knee Solution, Intramedullary Instrumentation Surgical Technique for the NexGen Cruciate Retaining & Legacy Posterior Stabilized Knee", Zimmer, Inc., (1995, 1997, 1998), 1-33.
"NexGen Implant Options Surgeon-Specific", Zimmer Inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"Persona "Medial Congruent Articular Surface" System Overview", Zimmer, Inc., (2015), 6 pgs.
"Persona "The Personalized Knee System"", Medial Congruent Sales Training, Zimmer, Inc., (Jul. 2015), 53 pgs.
"Persona "The Personalized Knee System" Medial Congruent Advanced Bearings", Zimmer, Inc., (2015), 2 pgs.
"Persona "The Personalized Knee System" Medial Congruent Articular Surface Design Rationale", Zimmer, Inc., (2015), 20 pgs.
"Persona "The Personalized Knee System" Persona Medial Congruent", Mar. 24-28, 2015 at the American Academy of Orthopaedic Surgeons (AAOS) Annual Meeting., (Mar. 2015), 1 pg.
"Persona "The Personalized Knee System" Surgical Technique", Zimmer, Inc., (2015), 72 pgs.
"Persona Medial Congruent Articular Surface", Sales Training, Zimmer Biomet, (Jan. 2016), 71 pgs.
"Primary/Revision Surgical Technique for NexGen Rotating Hinge Knee (RHK)", Zimmer, Inc. Nexgen Complete Knee Solution, 97-5880-02, (2002), 116 pgs.
"Revision Instrumentation Surgical Technique for Legacy Knee Constrained Condylar Knee", Zimmer, Inc. Nexgen Complete Knee Solution, 97-5994-202, (2001), 61 pgs.
"Surgical Technique for Cruciate Retaining Knees and Revision Instrumentation Surgical Technique for Cruciate Retaining Augmentable Knees", Zimmer, Inc. Nexgen Complete Knee Solution, 97-5970-202, (2002), 130 pgs.
"Surgical Technique for the Legacy Knee LPS-Flex Fixed Bearing Knee", Zimmer, Inc. Nexgen Complete Knee Solution, 97-5964-02, Rev. 1, (2000, 2002), 15 pgs.
"Surgical Technique for the Legacy Posterior Stabilized Knees", Zimmer, Inc. Nexgen Complete Knee Solution, 97-5996-02, (2002), 43 pgs.
"Surgical Technique—Nexgen Complete Knee Solution for the Legacy Knee LPS-Flex Fixed Bearing Knee", Zimmer, Inc., (2004, 2007), 12 pgs.
"The Zimmer Institute Surgical Technique MIS Quad-Sparing Surgical Technique for Total Knee Arthroplasty", NExGen Complete Knee Solution, (2004), 55 pgs.
"Zimmer MIS Intramedullary Instrumentation Surgical Technique for NexGen Cruciate Retaining & NexGen Legacy Posterior Stabilized Knees", printed 2005, 2009, Zimmer, Inc., (2009), 45 pgs.
"Zimmer Nexgen Cruciate Retaining (CR) and Legacy Knee Posterior Stabilized (LPS) Trabecular Metal Monoblock Tibias", Zimmer, Inc Surgical Technique Addendum, 97-7253-34, Rev. 3, (2004), 11 pgs.
"Zimmer NexGen CR-Flex and LPS-Flex Knees Surgical Technique with posterior Referencing Instrumentation.", Zimmer Inc., (2010, 2011), 48 pgs.
"Zimmer NexGen LCCK Surgical Technique for use with LCCK 4-in-1 Instrumentation", Zimmer, Inc.; copyright 2009, 2010, 2011, (May 2011), 52 pgs.
"Zimmer NexGen MIS Modular Tibial Plate and Keel Cemented Surgical Technique", Zimmer Inc., (2006, 2011), 26 pgs.
"Zimmer NexGen MIS Tibial Component", Brochure—97-5950-001-00 7.5mm, (2005, 2006), 8 pgs.
"Zimmer NexGen MIS Tibial Component Cemented Surgical Technique", Zimmer, Inc, #97-5950-002-00 Rev.1 1.5ML, (2005), 14 pgs.
"Zimmer NexGen MIS Tibial Component Cemented Surgical Technique", Zimmer Inc., (2005, 2006, 2008, 2009, 2010), 16 pgs.
"Zimmer NexGen Trabecular Metal Augments—Abbreviated Surgical Technique", Zimmer, Inc., (2004, 2006), 6 pgs.

(56) References Cited

OTHER PUBLICATIONS

"Zimmer NexGen Trabecular Metal Augments Surgical Technique for LCCK & Rotating Hing Knee Trabecular Metal Augments", Zimmer, Inc. 97-5448-02, Rev. 1, (2004), 6 pgs.
"Zimmer NexGen Trabecular Metal Primary Patella Surgical Technique", Zimmer. Inc., 97-7255-112-00, (2005), 10 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
Freeman, M.A.R., et al., "The Movement of the Knee Studied by Magnetic Resonance Imaging", Advanced Bearings—Clinical Orthopedics & Related Research 2003, (2003), 1 pg.
Hofmann, Aaron A, et al., "Posterior Stabilization in Total Knee Arthroplasty with Use of an Ultracongruent Polyethylene", The Journal of Arthroplasty vol. 15, No. 5, (2000), 576-583.
Partovi, Hamid, "Flow-Through Latch and Edge-Triggered Flip-Flop Hybrid Elements", Proceedings of the IEEE International Solid-State Circuits Conference, Digest of Technical Papers and Slide Supplement, NexGen Inc., Milpitas, CA, (1996), 40 pgs.
Siggelkow, Eik, et al., "Impact of Tibia Bearing Surface and Femoral Component Design on Flexion Kinematics During Lunge", Mar. 28-31, 2015 at the Orthopaedic Research Society (ORS) Annual Meeting (Poster #1645), (Mar. 2015), 1 pg.
Siggelkow, Eik, et al., "Impact of Tibia Bearing Surface Design on Deep Knee Bend Kinematics", Mar. 24-28, 2015 at the AAOS Conference (Poster #P142), (Mar. 2015), 1 pg.
"U.S. Appl. No. 14/034,937, Notice of Allowance dated Aug. 30, 2017", 14 pgs.
"U.S. Appl. No. 14/791,952, Corrected Notice of Allowance dated Jul. 21, 2017", 2 pgs.
"U.S. Appl. No. 15/003,091, Response filed Sep. 20, 2017 to Non Final Office Action dated Jun. 20, 2017", 17 pgs.
"U.S. Appl. No. 15/703,678, Preliminary Amendment filed Sep. 28, 2017", 9 pgs.
"U.S. Appl. No. 15/703,692, Preliminary Amendment filed Sep. 28, 2017", 9 pgs.
"U.S. Appl. No. 15/703,713, Preliminary Amendment filed Sep. 28, 2017", 7 pgs.
"Australian Application Serial No. 2016225911, Response filed Aug. 22, 2017 to First Examiners Report dated Jun. 2, 2017", 18pgs.
"Canadian Application Serial No. 2,806,321, Office Action dated Jun. 15, 2017", 3 pgs.
"Chinese Application Serial No. 201610634595.5, Office Action dated Jun. 21, 2017", w/English Translation, 9 pgs.
"European Application Serial No. 15191781.2, Response filed Sep. 28, 2017 to Extended European Search Report dated Mar. 1, 2017", 14pgs.
"U.S. Appl. No. 14/034,937, Appeal Decision dated May 30, 2017", 34 pgs.
"U.S. Appl. No. 14/063,593, Notice of Allowance dated May 2, 2017", 5 pgs.
"U.S. Appl. No. 14/063,593, Notice of Allowance dated May 25, 2017", 5 pgs.
"U.S. Appl. No. 14/063,593, Response filed Feb. 24, 2017 to Non Final Office Action dated Nov. 30, 2016", 17 pgs.
"U.S. Appl. No. 14/791,952, Final Office Action dated Mar. 31, 2017", 8 pgs.
"U.S. Appl. No. 14/791,952, Notice of Allowance dated May 30, 2017", 7 pgs.
"U.S. Appl. No. 14/791,952, Response filed Mar. 20, 2017 to Non Final Office Action dated Dec. 19, 2016", 12 pgs.
"U.S. Appl. No. 14/791,952, Response filed May 17, 2017—to Final Office Action dated Mar. 31, 2017", 10 pgs.
"U.S. Appl. No. 15/003,091, Non Final Office Action dated Jun. 20, 2017", 14 pgs.
"U.S. Appl. No. 15/177,734, Non Final Office Action dated Feb. 10, 2017", 21 pgs.
"U.S. Appl. No. 15/177,734, Notice of Allowance dated May 17, 2017", 7 pgs.
"U.S. Appl. No. 15/177,734, Preliminary Amendment filed Jun. 22, 2016", 8 pgs.
"U.S. Appl. No. 15/177,734, Response filed Apr. 19, 2017 to Non Final Office Action dated Feb. 10, 2017", 22 pgs.
"Australian Application Serial No. 2012368262, Response filed Jan. 17, 2017 to Office Action dated Nov. 2, 2016", 21 pgs.
"Australian Application Serial No. 2012368262, Response filed May 15, 2017 to Subsequent Examiners Report dated Mar. 16, 2017", 2 pgs.
"Australian Application Serial No. 2012368262, Subsequent Examiners Report dated Mar. 16, 2017", 3 pgs.
"Australian Application Serial No. 2016225911, First Examiners Report dated Jun. 2, 2017", 3 pgs.
"Canadian Application Serial No. 2,806,326, Office Action dated Jun. 19, 2017", 3 pgs.
"Chinese Application Serial No. 201280067473.2, Preliminary Amendment filed Jan. 29, 2015", No English Translation or Claims, 10 pgs.
"Chinese Application Serial No. 201280067473.2, Response filed Dec. 4, 2015 to Office Action dated Nov. 20, 2015", No English Translation, 7 pgs.
"Chinese Application Serial No. 201510640436.1, Response filed Feb. 16, 2017 to Office Action dated Sep. 28, 2016", (W/ English Translation), 18 pgs.
"Chinese Application Serial No. 201610685172.6, Office Action dated Apr. 10, 2017", (W/ English Translation), 11 pgs.
"European Application Serial No. 11815029.1, Response filed Apr. 10, 2017 to Communication Pursuant to Article 94(3) EPC dated Sep. 29, 2016", 22 pgs.
"European Application Serial No. 12756058.9, Response filed May 26, 2017 to Office Action dated Jan. 17, 2017", 16 pgs.
"European Application Serial No. 15191781.2, Extended European Search Report dated Mar. 1, 2017", 8 pgs.
"Japanese Application Serial No. 2015-162707, Response filed Jan. 26, 2017 to Office Action dated Nov. 27, 2016", (W/ English Translation), 16 pgs.
"U.S. Appl. No. 13/189,324, Examiner Interview Summary dated Jan. 3, 2014", 4 pgs.
"U.S. Appl. No. 13/189,324, Final Office Action dated Jul. 16, 2013", 19 pgs.
"U.S. Appl. No. 13/189,324, Non Final Office Action dated Dec. 11, 2012", 19 pgs.
"U.S. Appl. No. 13/189,324, Notice of Allowance dated Feb. 20, 2014", 8 pgs.
"U.S. Appl. No. 13/189,324, PTO Response to 312 Amendment dated May 29, 2014", 2 pgs.
"U.S. Appl. No. 13/189,324, Response filed Jan. 14, 2014 to Final Office Action dated Jul. 16, 2013", 23 pgs.
"U.S. Appl. No. 13/189,324, Response filed Jun. 10, 2013 to Non Final Office Action dated Dec. 11, 2012", 24 pgs.
"U.S. Appl. No. 13/189,328, Non Final Office Action dated Mar. 19, 2013", 10 pgs.
"U.S. Appl. No. 13/189,328, Notice of Allowance dated Oct. 8, 2013", 12 pgs.
"U.S. Appl. No. 13/189,328, PTO Response to 312 Amendment dated Dec. 13, 2013", 2 pgs.
"U.S. Appl. No. 13/189,328, Response filed Jan. 10, 2013 to Restriction Requirement dated Dec. 10, 2012", 9 pgs.
"U.S. Appl. No. 13/189,328, Response filed Jul. 18, 2013 to Non Final Office Action dated Mar. 19, 2013", 16 pgs.
"U.S. Appl. No. 13/189,328, Restriction Requirement dated Dec. 10, 2012", 6 pgs.
"U.S. Appl. No. 13/189,336, Notice of Allowance dated Sep. 13, 2013", 30 pgs.
"U.S. Appl. No. 13/189,336, PTO Response to 312 Amendment dated Nov. 25, 2013", 2 pgs.
"U.S. Appl. No. 13/189,336, Response filed Apr. 15, 2013 to Restriction Requirement dated Jan. 30, 2013", 21 pgs.
"U.S. Appl. No. 13/189,336, Response filed Jul. 17, 2013 to Restriction Requirement dated Jun. 17, 2013", 20 pgs.
"U.S. Appl. No. 13/189,336, Restriction Requirement dated Jan. 30, 2013", 5 pgs.
"U.S. Appl. No. 13/189,336, Restriction Requirement dated Jun. 17, 2013", 6 pgs.

(56) References Cited

OTHER PUBLICATIONS

"U.S. Appl. No. 13/189,338, Notice of Allowance dated Sep. 23, 2013", 23 pgs.
"U.S. Appl. No. 13/189,338, Response filed Apr. 15, 2013 to Restriction Requirement dated Feb. 14, 2013", 18 pgs.
"U.S. Appl. No. 13/189,338, Response filed Jul. 17, 2013 to Restriction Requirement dated Jun. 17, 2013", 16 pgs.
"U.S. Appl. No. 13/189,338, Restriction Requirement dated Feb. 14, 2013", 5 pgs.
"U.S. Appl. No. 13/189,338, Restriction Requirement dated Jun. 17, 2013", 6 pgs.
"U.S. Appl. No. 13/189,339, Notice of Allowance dated Sep. 20, 2013", 16 pgs.
"U.S. Appl. No. 13/189,339, Response filed Apr. 15, 2013 to Restriction Requirement dated Mar. 6, 2013", 11 pgs.
"U.S. Appl. No. 13/189,339, Response filed Jul. 17, 2013 to Restriction Requirement dated Jun. 17, 2013", 10 pgs.
"U.S. Appl. No. 13/189,339, Restriction Requirement dated Mar. 6, 2013", 6 pgs.
"U.S. Appl. No. 13/189,339, Restriction Requirement dated Jun. 17, 2013", 7 pgs.
"U.S. Appl. No. 13/229,103, Applicant Interview Summary dated Sep. 23, 2013", 2 pgs.
"U.S. Appl. No. 13/229,103, Examiner Interview Summary dated Sep. 13, 2013", 3 pgs.
"U.S. Appl. No. 13/229,103, Non Final Office Action dated Apr. 1, 2013", 18 pgs.
"U.S. Appl. No. 13/229,103, Notice of Allowance dated Sep. 18, 2013", 9 pgs.
"U.S. Appl. No. 13/229,103, Response filed Jul. 1, 2013 to Non Final Office Action dated Apr. 1, 2013", 19 pgs.
"U.S. Appl. No. 13/229,103, Supplemental Notice of Allowability dated Oct. 18, 2013", 2 pgs.
"U.S. Appl. No. 13/593,339, Non Final Office Action dated Oct. 4, 2013", 7 pgs.
"U.S. Appl. No. 13/593,339, Notice of Allowance dated Feb. 14, 2014", 9 pgs.
"U.S. Appl. No. 13/593,339, Preliminary Amendment filed Aug. 23, 2012", 6 pgs.
"U.S. Appl. No. 13/593,339, Response filed Jan. 31, 2014 to Non-Final Office Action dated Oct. 4, 2013", 19 pgs.
"U.S. Appl. No. 13/593,339, Response filed Aug. 30, 2013 to Restriction Requirement dated Aug. 1, 2013", 14 pgs.
"U.S. Appl. No. 13/593,339, Restriction Requirement dated Aug. 1, 2013", 5 pgs.
"U.S. Appl. No. 13/593,339, Supplemental Notice of Allowability dated Mar. 31, 2014", 2 pgs.
"U.S. Appl. No. 13/594,543, Corrected Notice of Allowance dated Mar. 16, 2016", 2 pgs.
"U.S. Appl. No. 13/594,543, Examiner Interview Summary dated Jan. 22, 2016", 3 pgs.
"U.S. Appl. No. 13/594,543, Final Office Action dated Jul. 17, 2014", 12 pgs.
"U.S. Appl. No. 13/594,543, Final Office Action dated Nov. 20, 2015", 28 pgs.
"U.S. Appl. No. 13/594,543, Non Final Office Action dated Jun. 19, 2015", 30 pgs.
"U.S. Appl. No. 13/594,543, Non Final Office Action dated Dec. 26, 2013", 15 pgs.
"U.S. Appl. No. 13/594,543, Non-Final Office Action dated Jan. 9, 2015", 23 pgs.
"U.S. Appl. No. 13/594,543, Notice of Allowance dated Mar. 1, 2016", 9 pgs.
"U.S. Appl. No. 13/594,543, Preliminary Amendment filed Aug. 24, 2012", 4 pgs.
"U.S. Appl. No. 13/594,543, Response filed Feb. 8, 2016 to Final Office Action dated Nov. 20, 2015", 17 pgs.
"U.S. Appl. No. 13/594,543, Response filed Apr. 7, 2015 to Non-Final Office Action dated Jan. 9, 2015", 27 pgs.
"U.S. Appl. No. 13/594,543, Response filed May 7, 2014 to Non-Final office Action dated Dec. 26, 2013", 17 pgs.
"U.S. Appl. No. 13/594,543, Response filed Sep. 21, 2015 to Non-Final Office Action dated Jun. 19, 2015", 25 pgs.
"U.S. Appl. No. 13/594,543, Response filed Oct. 11, 2013 to Restriction Requirement dated Sep. 12, 2013", 8 pgs.
"U.S. Appl. No. 13/594,543, Response filed Dec. 17, 2014 to Final Office Action dated Jul. 17, 2014", 15 pgs.
"U.S. Appl. No. 13/594,543, Restriction Requirement dated Sep. 12, 2013", 5 pgs.
"U.S. Appl. No. 14/034,937, Appeal Brief filed Sep. 9, 2015", 41 pgs.
"U.S. Appl. No. 14/034,937, Final Office Action dated Jun. 5, 2015", 22 pgs.
"U.S. Appl. No. 14/034,937, Non Final Office Action dated Jan. 2, 2015", 21 pgs.
"U.S. Appl. No. 14/034,937, Preliminary Amendment filed Sep. 24, 2013", 3 pgs.
"U.S. Appl. No. 14/034,937, Response filed Mar. 30, 2015 to Non-Final Office Action", 24 pgs.
"U.S. Appl. No. 14/034,937, Response filed Oct. 27, 2014 to Restriction Requirement dated Sep. 11, 2014", 12 pgs.
"U.S. Appl. No. 14/034,937, Restriction Requirement dated Sep. 11, 2014", 6 pgs.
"U.S. Appl. No. 14/034,937, Supplemental Preliminary Amendment filed Oct. 24, 2013", 11 pgs.
"U.S. Appl. No. 14/034,944, Non Final Office Action dated Mar. 3, 2015", 16 pgs.
"U.S. Appl. No. 14/034,944, Notice of Allowance dated Aug. 28, 2015", 7 pgs.
"U.S. Appl. No. 14/034,944, Preliminary Amendment filed Sep. 24, 2013", 3 pgs.
"U.S. Appl. No. 14/034,944, Response filed Jun. 23, 2015 to Non Final Office Action dated Mar. 3, 2015", 15 pgs.
"U.S. Appl. No. 14/034,944, Response filed Dec. 15, 2014 to Restriction Requirement dated Oct. 14, 2014", 12 pgs.
"U.S. Appl. No. 14/034,944, Restriction Requirement dated Oct. 14, 2014", 6 pgs.
"U.S. Appl. No. 14/034,944, Supplemental Preliminary Amendment filed Oct. 24, 2013", 11 pgs.
"U.S. Appl. No. 14/034,954, Advisory Action dated Aug. 25, 2015", 3 pgs.
"U.S. Appl. No. 14/034,954, Final Office Action dated Jun. 1, 2015", 26 pgs.
"U.S. Appl. No. 14/034,954, Non Final Office Action dated Dec. 19, 2014", 25 pgs.
"U.S. Appl. No. 14/034,954, Notice of Allowance dated Nov. 20, 2015", 11 pgs.
"U.S. Appl. No. 14/034,954, Preliminary Amendment filed Sep. 24, 2013", 3 pgs.
"U.S. Appl. No. 14/034,954, Response filed Mar. 17, 2015 to Non Final Office Action dated Dec. 19, 2014", 21 pgs.
"U.S. Appl. No. 14/034,954, Response filed Aug. 3, 2015 to Final Office Action dated Jun. 1, 2015", 19 pgs.
"U.S. Appl. No. 14/034,954, Response filed Aug. 31, 2015 to Advisory Action dated Aug. 25, 2015", 21 pgs.
"U.S. Appl. No. 14/034,954, Response filed Oct. 27, 2014 to Restriction Requirement dated Aug. 25, 2014", 11 pgs.
"U.S. Appl. No. 14/034,954, Restriction Requirement dated Aug. 25, 2014", 7 pgs.
"U.S. Appl. No. 14/034,954, Supplemental Preliminary Amendment filed Oct. 25, 2013", 8 pgs.
"U.S. Appl. No. 14/034,963, Final Office Action dated Apr. 13, 2015", 22 pgs.
"U.S. Appl. No. 14/034,963, Final Office Action dated Oct. 13, 2015", 11 pgs.
"U.S. Appl. No. 14/034,963, Non Final Office Action dated Jul. 1, 2015", 15 pgs.
"U.S. Appl. No. 14/034,963, Non Final Office Action dated Nov. 21, 2014", 19 pgs.
"U.S. Appl. No. 14/034,963, Notice of Allowance dated Dec. 18, 2015", 5 pgs.

(56) References Cited

OTHER PUBLICATIONS

"U.S. Appl. No. 14/034,963, Preliminary Amendment filed Sep. 24, 2013", 3 pgs.
"U.S. Appl. No. 14/034,963, Response filed Mar. 20, 2015 to Non-Final Office Action dated Nov. 21, 2014", 20 pgs.
"U.S. Appl. No. 14/034,963, Response filed Jun. 19, 2015 to Final Office Action dated Apr. 13, 2015", 17 pgs.
"U.S. Appl. No. 14/034,963, Response filed Sep. 30, 2015 to Non Final Office Action dated Jul. 1, 2015", 14 pgs.
"U.S. Appl. No. 14/034,963, Response filed Nov. 20, 2015 to Final Office Action dated Oct. 13, 2015", 12 pgs.
"U.S. Appl. No. 14/063,593, Advisory Action dated Aug. 19, 2016", 3 pgs.
"U.S. Appl. No. 14/063,593, Final Office Action dated Jun. 9, 2016", 10 pgs.
"U.S. Appl. No. 14/063,593, Non Final Office Action dated Jan. 25, 2015-16", 9 pgs.
"U.S. Appl. No. 14/063,593, Non Final Office Action dated Nov. 30, 2016", 12 pgs.
"U.S. Appl. No. 14/063,593, Preliminary Amendment filed Oct. 25, 2013", 3 pgs.
"U.S. Appl. No. 14/063,593, Response filed Jan. 4, 2016 to Restriction Requirement dated Nov. 6, 2015", 6 pgs.
"U.S. Appl. No. 14/063,593, Response filed Aug. 11, 2016 to Final Office Action dated Jun. 9, 2016", 10 pgs.
"U.S. Appl. No. 14/063,593, Restriction Requirement dated Nov. 6, 2015", 6 pgs.
"U.S. Appl. No. 14/278,805, Notice of Allowance dated Dec. 1, 2015", 8 pgs.
"U.S. Appl. No. 14/278,805, Supplemental Notice of Allowability dated Jan. 21, 2016", 2 pgs.
"U.S. Appl. No. 14/284,144, Final Office Action dated Aug. 7, 2015", 13 pgs.
"U.S. Appl. No. 14/284,144, Non Final Office Action dated Mar. 25, 2015", 26 pgs.
"U.S. Appl. No. 14/284,144, Notice of Allowance dated Oct. 29, 2015", 8 pgs.
"U.S. Appl. No. 14/284,144, Preliminary Amendment filed May 21, 2014", 3 pgs.
"U.S. Appl. No. 14/284,144, Response filed Oct. 9, 215 to Final Office Action dated Aug. 7, 2015", 13 pgs.
"U.S. Appl. No. 14/284,144, Response filed Jun. 23, 2015 to Non Final Office Action dated Mar. 25, 2015", 22 pgs.
"U.S. Appl. No. 14/284,144, Supplemental Preliminary Amendment filed Jul. 3, 2014", 10 pgs.
"U.S. Appl. No. 14/791,952, Final Office Action dated Sep. 1, 2016", 17 pgs.
"U.S. Appl. No. 14/791,952, Non Final Office Action dated Apr. 21, 2016", 12 pgs.
"U.S. Appl. No. 14/791,952, Non Final Office Action dated Dec. 29, 2016", 12 pgs.
"U.S. Appl. No. 14/791,952, Preliminary Amendment filed Jul. 7, 2015", 7 pgs.
"U.S. Appl. No. 14/791,952, Response filed Jul. 15, 2015 to Non Final Office Action dated Apr. 21, 2016", 18 pgs.
"U.S. Appl. No. 14/791,952, Response filed Nov. 21, 2016 to Final Office Action dated Sep. 1, 2016", 15 pgs.
"U.S. Appl. No. 15/003,091, Preliminary Amendment filed Jan. 22, 2016", 12 pgs.
"U.S. Appl. No. 15/045,799, Non Final Office Action dated Nov. 1, 2016", 8 pgs.
"U.S. Appl. No. 15/045,799, Notice of Allowance dated Mar. 10, 2017", 10 pgs.
"U.S. Appl. No. 15/045,799, Preliminary Amendment filed Feb. 18, 2016", 9 pgs.
"U.S. Appl. No. 15/045,799, PTO Response to Rule 312 Communication dated Apr. 18, 2017", 2 pgs.
"U.S. Appl. No. 15/045,799, Response filed Feb. 1, 2017 to Non Final Office Action dated Nov. 1, 2016", 15 pgs.
"U.S. Appl. No. 14/063,593, Response filed Apr. 20, 2016 to Non Final Office Action dated Jan. 25, 2016", 17 pgs.
"Australian Application Serial No. 2011286306, First Examiner Report dated Jun. 19, 2013", 4 pgs.
"Australian Application Serial No. 2011286306, Response filed Jun. 3, 2014 to First Examiner Report dated Jun. 19, 2013", 16 pgs.
"Australian Application Serial No. 2011286307, First Examiner Report dated Oct. 17, 2013", 2 pgs.
"Australian Application Serial No. 2011286307, Response filed May 21, 2014 to First Examiner Report dated Oct. 17, 2013", 16 pgs.
"Australian Application Serial No. 2011286308, First Examiner Report dated Jun. 21, 2013", 4 pgs.
"Australian Application Serial No. 2011286308, Response filed Jun. 6, 2014 First Examiner Report dated Jun. 21, 2013", 19 pgs.
"Australian Application Serial No. 2011286309, First Examiner Report dated Jun. 21, 2013", 3 pgs.
"Australian Application Serial No. 2011286309, Response filed Jun. 10, 2014 to First Examiner Report dated Jun. 21, 2013", 4 pgs.
"Australian Application Serial No. 2012341026, First Examiner Report dated Jul. 14, 2014", 2 pgs.
"Australian Application Serial No. 2012341026, Response filed Nov. 21, 2014 to First Examiner Report dated Jul. 14, 2014", 1 pg.
"Australian Application Serial No. 2012341026, Statement of Proposed Amendment filed Jun. 18, 2014", 25 pgs.
"Australian Application Serial No. 2012368262, First Examiner Report dated Nov. 2, 2016", 4 pgs.
"Australian Application Serial No. 2014250709, First Examiner Report dated Dec. 21, 2015", 3 pgs.
"Australian Application Serial No. 2014250709, Response filed May 4, 2016 to First Examiner Report dated Dec. 21, 2015", 12 pgs.
"Australian Application Serial No. 2014250709, Subsequent Examiners Report dated May 31, 2016", 6 pgs.
"Australian Application Serial No. 2014250710, First Examiner Report dated Dec. 11, 2015", 7 pgs.
"Australian Application Serial No. 2014250710, Response filed Mar. 22, 2016 to First Examiner Report dated Dec. 11, 2015", 18 pgs.
"Australian Application Serial No. 2014250710, Response filed May 4, 2016 to Subsequent Examiners Report dated Mar. 23, 20q16", 15 pgs.
"Australian Application Serial No. 2014250710, Subsequent Examiners Report dated Mar. 23, 2016", 3 pgs.
"Australian Application Serial No. 2014250711, First Examiner Report dated Feb. 12, 2016", 7 pgs.
"Australian Application Serial No. 2014250711, Response filed Apr. 27, 2016 to First Examiner Report dated Feb. 12, 2016", 32 pgs.
"Australian Application Serial No. 2015201511, First Examination Report dated Apr. 18, 2016", 2 pgs.
"Australian Application Serial No. 2015201511, Response filed Jun. 30, 2016 to First Examiner Report dated Apr. 18, 2016", 12 pgs.
"Bi-Cruciate Stabilized Knee System", Design Rationale, Smith & Nephew Journal, (2006), 20 pgs.
"Canadian Application Serial No. 2,806,325, Office Action dated Mar. 14, 2016", 4 pgs.
"Canadian Application Serial No. 2,806,325, Response filed Sep. 14, 2016 to Office Action dated Mar. 14, 2016", 17 pgs.
"Canadian Application Serial No. 2,856,571 Response filed Jan. 22, 2015 to Office Action dated Jul. 22, 2014", 24 pgs.
"Canadian Application Serial No. 2,856,571, Office Action dated Jul. 22, 2014", 2 pgs.
"Chinese Application Serial No. 201180045673.3, Office Action dated Feb. 14, 2016", (W/English Translation), 17 pgs.
"Chinese Application Serial No. 201180045673.3, Office Action dated Mar. 29, 2015", (W/English Translation), 6 pgs.
"Chinese Application Serial No. 201180045673.3, Office Action dated Aug. 12, 2015", (W/English Translation), 7 pgs.
"Chinese Application Serial No. 201180045673.3, Response filed Jun. 19, 2015 to Office Action dated Mar. 29, 2015", (W/ English translation of claims), 11 pgs.
"Chinese Application Serial No. 201180045673.3, Response filed Oct. 27, 2015 to Office Action dated Aug. 12, 2015", (W/ English translation of claims), 9 pgs.

(56) References Cited

OTHER PUBLICATIONS

"Chinese Application Serial No. 201180045681.8, Office Action dated Jan. 22, 2015", (W/English Translation), 11 pgs.
"Chinese Application Serial No. 201180045681.8, Response filed May 14, 2015 to Office Action dated Jan. 22, 2015", W/ English Claims, 17 pgs.
"Chinese Application Serial No. 201180045683.7, Office Action dated Mar. 9, 2015", (W/English Translation), 6 pgs.
"Chinese Application Serial No. 201180045683.7, Response filed Jul. 14, 2015 to Office Action dated Mar. 9, 2015", (W/ English translation of claims), 30 pgs.
"Chinese Application Serial No. 201180045689.4, Office Action dated Jan. 5, 2015", (W/English Translation), 4 pgs.
"Chinese Application Serial No. 201180045689.4, Office Action dated Aug. 15, 2015", (W/English Translation), 11 pgs.
"Chinese Application Serial No. 201180045689.4, Response filed May 1, 2015 to Office Action dated Jan. 5, 2015", W/ English Claims, 13 pgs.
"Chinese Application Serial No. 201280067473.2, Office Action dated Feb. 1, 2016", (W/English Translation), 4 pgs.
"Chinese Application Serial No. 201280067473.2, Office Action dated May 20, 2015", (W/English Translation), 15 pgs.
"Chinese Application Serial No. 201280067473.2, Office Action dated Nov. 20, 2015", W/English Translation of Claims, 7 pgs.
"Chinese Application Serial No. 201280067473.2, Response filed Apr. 7, 2016 to Office Action dated Feb. 21, 2016", (W/ English translation of claims), 11 pgs.
"Chinese Application Serial No. 201280067473.2, Response filed Sep. 7, 2015 to Office Action dated May 20, 2015", (W/ English translation of claims), 12 pgs.
"Chinese Application Serial No. 201280071940.9, Office Action dated Jul. 22, 2015", (W/ English Translation), 13 pgs.
"Chinese Application Serial No. 201280071940.9, Preliminary Amendment filed Mar. 23, 2015", W/ English Claims, 11 pgs.
"Chinese Application Serial No. 201510640436.1, Office Action dated Sep. 28, 2016", (W/ English Translation), 13 pgs.
"European Application Serial No. 11738918.9, Examination Notification Art. 94(3) dated Oct. 23, 2014", 5 pgs.
"European Application Serial No. 11738918.9, Preliminary Amendment dated Sep. 24, 2013", 11 pgs.
"European Application Serial No. 11738918.9, Response filed Mar. 2, 2015 to Examination Notification Art. 94(3) dated Oct. 23, 2014", 14 pgs.
"European Application Serial No. 11738919.7, Examination Notification Art. 94(3) dated Jul. 7, 2014", 4 pgs.
"European Application Serial No. 11738919.7, Preliminary Amendment filed Nov. 4, 2013", 25 pgs.
"European Application Serial No. 11738919.7, Response filed Nov. 13, 2014 to Examination Notification Art. 94(3) dated Jul. 7, 2014", 14 pgs.
"European Application Serial No. 11738920.5, Communication Pursuant to Article 94(3) EPC dated Mar. 15, 2016", 4 pgs.
"European Application Serial No. 11738920.5, Preliminary Amendment dated Sep. 24, 2013", 9 pgs.
"European Application Serial No. 11738920.5, Response filed Jul. 25, 2016 to Communication Pursuant to Article 94(3) EPC dated Mar. 15, 2016", 6 pgs.
"European Application Serial No. 11738920.5, Response filed Sep. 24, 2013 to Communication pursuant to Rules 161(2) and 162 EPC dated Mar. 15, 2013", 22 pgs.
"European Application Serial No. 11758060.5, Response filed Apr. 21, 2016 to Communication Pursuant to Article 94(3) EPC dated Dec. 11, 2015", 16 pgs.
"European Application Serial No. 11758060.5, Communication Pursuant to Article 94(3) EPC dated Jul. 12, 2016", 3 pgs.
"European Application Serial No. 11758060.5, Communication Pursuant to Article 94(3) EPC dated Dec. 11, 2015", 4 pgs.
"European Application Serial No. 11758060.5, Preliminary Amendment filed Nov. 4, 2013", 15 pgs.
"European Application Serial No. 11758060.5, Response filed Nov. 15, 2016 to Communication Pursuant to Article 94(3) EPC dated Jul. 12, 2016", 23 pgs.
"European Application Serial No. 11815029.1, Communication Pursuant to Article 94(3) EPC dated Sep. 29, 2016", 4 pgs.
"European Application Serial No. 11815029.1, Extended European Search Report dated Dec. 10, 2013", 8 pgs.
"European Application Serial No. 11815029.1, Response filed Jul. 21, 2014 Extended European Search Report dated Dec. 10, 2013", 15 pgs.
"European Application Serial No. 12756058.9, Office Action dated Jan. 23, 2017", 5 Pgs.
"European Application Serial No. 12756058.9, Preliminary Amendment filed Apr. 20, 2015", 12 pgs.
"European Application Serial No. 12756869.9 Response filed Feb. 10, 2015 to Communication Pursuant to Rule 161(1) and 162 EPC dated Jul. 31, 2014", 14 pgs.
"European Application Serial No. 12756869.9, Examination Notification Art. 94(3) dated Jul. 2, 2015", 4 pgs.
"European Application Serial No. 12756869.9, Response filed Nov. 12, 2015 to Examination Notification Art. 94(3) dated Jul. 2, 2015", 28 pgs.
"European Application Serial No. 15160934.4, Extended European Search Report dated Jun. 1, 2016", 8 pgs.
"European Application Serial No. 15160934.4, Response filed Dec. 21, 2016 to Extended European Search Report dated Jun. 1, 2016", 5 pgs.
"European Application Serial No. 15174394.5, Extended European Search Report dated Mar. 21, 2016", 8 pgs.
"European Application Serial No. 15174394.5, Response filed Nov. 18, 2016 to Extended European Search Report dated Mar. 21, 2016", 12 pgs.
"Gender Solutions Natural-Knee Flex System", Zimmer, Inc., (2007, 2009), 6 pgs.
"International Application Serial No. PCT/US2011/045077, International Preliminary Report on Patentability dated Jul. 5, 2012", 23 pgs.
"International Application Serial No. PCT/US2011/045077, International Search Report and Written Opinion dated Jan. 9, 2012", 15 pgs.
"International Application Serial No. PCT/US2011/045078, International Preliminary Report on Patentability dated Feb. 7, 2013", 11 pgs.
"International Application Serial No. PCT/US2011/045078, International Search Report and Written Opinion dated Jan. 9, 2012", 14 pgs.
"International Application Serial No. PCT/US2011/045080, International Preliminary Report on Patentability dated Feb. 7, 2013", 13 pgs.
"International Application Serial No. PCT/US2011/045080, International Search Report dated Jan. 9, 2012", 7 pgs.
"International Application Serial No. PCT/US2011/045080, Written Opinion dated Jan. 9, 2012", 11 pgs.
"International Application Serial No. PCT/US2011/045082, International Preliminary Report on Patentability dated Feb. 7, 2013", 11 pgs.
"International Application Serial No. PCT/US2011/045082, International Search Report dated Jan. 9, 2012", 5 pgs.
"International Application Serial No. PCT/US2011/045082, Written Opinion dated Jan. 9, 2012", 10 pgs.
"International Application Serial No. PCT/US2011/045083, International Preliminary Report on Patentability dated Feb. 7, 2013", 8 pgs.
"International Application Serial No. PCT/US2011/045083, International Search Report dated Dec. 7, 2011", 2 pgs.
"International Application Serial No. PCT/US2011/045083, Written Opinion dated Dec. 7, 2011", 6 pgs.
"International Application Serial No. PCT/US2011/051021, International Preliminary Report on Patentability dated Mar. 21, 2013", 8 pgs.
"International Application Serial No. PCT/US2011/051021, International Search Report dated Nov. 23, 2011", 12 pgs.

(56) References Cited

OTHER PUBLICATIONS

"International Application Serial No. PCT/US2011/051021, Written Opinion dated Nov. 23, 2011",7 pgs.
"International Application Serial No. PCT/US2012/052132, International Preliminary Report on Patentability dated Jun. 5, 2014", 12 pgs.
"International Application Serial No. PCT/US2012/052132, International Search Report dated Jan. 10, 2013", 5 pgs.
"International Application Serial No. PCT/US2012/052132, Invitation to Pay Additional Fees and Partial Search Report dated Nov. 15, 2012", 7 pgs.
"International Application Serial No. PCT/US2012/052132, Written Opinion dated Jan. 10, 2013", 10 pgs.
"International Application Serial No. PCT/US2012/052340, International Preliminary Report on Patentability dated Aug. 14, 2014", 8 pgs.
"International Application Serial No. PCT/US2012/052340, Search Report dated Oct. 12, 2012", 4 pgs.
"International Application Serial No. PCT/US2012/052340, Written Opinion dated Oct. 12, 2012", 6 pgs.
"Japanese Application Serial No. 2015-162707, Office Action dated Jun. 28, 2016", (W/ English Translation), 8 pgs.
"Japanese Application Serial No. 2013-521854, Notice of Reason for Rejection dated Sep. 16, 2014", (W/ English Translation), 6 pgs.
"Japanese Application Serial No. 2013-521854, Response filed Dec. 16, 2014 to Notice of Reason for Rejection dated Sep. 16, 2014", W/ English Claims, 11 pgs.
"Japanese Application Serial No. 2013-521855, Amendment filed Jul. 22, 2014", (W/ English Translation), 20 pgs.
"Japanese Application Serial No. 2013-521855, Office Action dated Mar. 24, 2015", W/ English Translation, 8 pgs.
"Japanese Application Serial No. 2013-521856, Office Action dated Sep. 1, 2015", (W/ English Translation), 5 pgs.
"Japanese Application Serial No. 2013-521857, Notice of Reasons for Rejection dated Aug. 18, 2015", (W/ English Translation), 6 pgs.
"Japanese Application Serial No. 2013-521857, Preliminary Amendment filed May 18, 2014", (W/ English translation of claims), 9 pgs.
"Japanese Application Serial No. 2013-521857, Response filed Jan. 25, 2016 to Notice of Reasons for Rejection dated Aug. 18, 2015", (W/ English Translation), 17 pgs.
"Japanese Application Serial No. 2014-542301, Office Action dated May 12, 2015", (W/ English Translation), 6 pgs.
"Japanese Application Serial No. 2014-542301, Response filed Aug. 10, 2015 to Office Action dated May 12, 2015", (W/ English translation of claims), 21 pgs.
"Japanese Application Serial No. 2014-554709, Office Action dated Jul. 5, 2016", (W/ English Translation), 6 pgs.
"Japanese Application Serial No. 2014-554709, Preliminary Amendment filed Jul. 29, 2015", (W/ English translation of claims), 8 pgs.
"Japanese Application Serial No. 2014-554709, Response filed Dec. 19, 2016 to Office Action dated Jul. 5, 2016", (W/ English Translation of Claims), 11 pgs.
"Japanese Application Serial No. 2015-162707, Office Action dated Nov. 29, 2016", (W/ English Translation), 3 pgs.
"Japanese Application Serial No. 2015-199496, Office Action dated Sep. 6, 2016", (W/ English Translation), 5 pgs.
"Japanese Application Serial No. 2015-199496, Response filed Dec. 5, 2016 to Office Action dated Sep. 6, 2016", (W/ English Translation of Claims), 9 pgs.
"LPS-Flex Fixed Bearing Knee: Surgical Technique", Zimmer, Inc., (2004, 2007, 2008), 16 pgs.
"Mexican Application Serial No. MX/a/2013/000988, Response filed Jun. 1, 2015 to Office Action dated Mar. 18, 2015", (W/ English Translation), 12 pgs.
"Mexican Application Serial No. MX/A/2013/000990, Office Action dated Feb. 19, 2015", (W/ English Translation), 4 pgs.
"Mexican Application Serial No. MX/A/2013/000990, Response filed Apr. 29, 2015 to Office Action dated Feb. 19, 2015", W/ English Claims, 18 pgs.

"Nexgen Complete Knee Solution", Extramedullary/Intramedullary Tibial Resector: Surgical Technique, Zimmer, Inc. 97-5997-02 Rev 1, (2000), 26 pgs.
"Nexgen Complete Knee Solution", Extramedullary/Intramedullary Tibial Resector: Surgical Technique, Zimmer, Inc. 97-5997-002-00 Rev. 2, (2000, 2008, 2009), 28 pgs.
"NexGen Trabecular Metal Modular Plates", Zimmer Inc., (2007), 19 pgs.
"PFC Sigma Knee System with Rotating Platform Technical/ Monograph", Depuy PFC Sigma RP, 0611-29-050 (Rev. 3), (1999), 70 pgs.
"Russian Application Serial No. 2013106942, Office Action dated Apr. 16, 2015", W/ English Translation, 5 pgs.
"Russian Application Serial No. 2013106942, Response filed Jul. 15, 2015 Office Action dated Apr. 16, 2015", (W/ English translation of claims), 146 pgs.
"Russian Application Serial No. 2013106943, Office Action dated Jul. 1, 2015", (W/ English Translation), 6 pgs.
"Russian Application Serial No. 2013106943, Response filed Apr. 28, 2016 to Office Action dated Dec. 28, 2015", (W/ English translation of claims), 19 pgs.
"Russian Application Serial No. 2013106943, Response filed Oct. 30, 2015 to Office Action dated Jul. 1, 2015", (W/ English translation of claims), 21 pgs.
"South African Application Serial No. 2013/01327, Amendment filed Apr. 24, 2014", W/ English Translation, 4 pgs.
"South African Application Serial No. 2013/01328, Amendment filed Apr. 24, 2014", W/ English Translation, 4 pgs.
"Surgical Technique for the CR-Flex Fixed Bearing Knee", NexGen Complete Knee Solution, Zimmer, Inc., (2003), 22 pgs.
"Tibial Baseplate: Pocket Guide (United States Version)", Zimmer, Inc.,, (2009), 17 pgs.
"Trabecular Metal Monoblock Tibial Components", Zimmer, Inc., (2007), 4 pgs.
"Trabecular Metal Monoblock Tibial Components Surgical Technique Addendum", Nexgen Zimmer, Inc., (2005, 2007), 12 pgs.
"Trabecular Metal Tibial Tray: Surgical Technique", NexGen Zimmer, Inc., (2007, 2009), 16 pgs.
Annayappa, Ramesh, et al., "Tibial Prosthesis", U.S. Appl. No. 13/189,324, filed Jul. 22, 2011, 50 pgs.
Annayappa, Ramesh, "Tibial Prosthesis", U.S. Appl. No. 13/189,328, filed Jul. 22, 2011, 82 pgs.
Ding, M., et al., "Age-related variations in the microstructure of human tibial cancellous bone", Journal of Orthopaedic Research, 20(3), (2002), 615-621.
Ding, M., et al., "Changes in the three-dimensional microstructure of human tibial cancellous bone in early osteoarthritis", Journal of Bone & Joint Surgery (British), 85-B(6), (Aug. 2003), 906-912.
Doyle, et al., "Comparative Analysis of Human Trabecular Bone and Polyurethane Foam", Purdue University., 1 pg.
Dunbar, M. J., et al., "Fixation of a Trabecular Metal Knee Arthroplasty Component: A Prospective Randomized Study", The Journal of Bone & Joint Surgery (American), vol. 91-A(7), (Jul. 2009), 1578-1586.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Hvid, Ivan, et al., "Trabecular bone Strength Patterns at the Proximal Tibial Epiphysis", Journal of Orthopaedic Research, vol. 3, No. 4, (1985), 464-472.
Klostermann, et al., "Distribution of bone mineral density with age and gender in the proximal tibia", Clinical Biomechanics 19, 376-376.
Lorenz, Stephan, et al., "Radiological evaluation of the anterolateral and posteromedial bundle insertion sites of the posterior cruciate ligament", Knee Surg Sports Traumatol Arthosc, vol. 17, (2009), 683-690.
Moorman, Claude, et al., "Tibial Insertion of the Posterior Cruciate Ligament: A Sagittal Plane Analysis Using Gross, Histologic, and Radiographic Methods", Arthroscopy: The Journal of Arthroscopic and Related Surgery, vol. 24, No. 3, (Mar. 2008), 269-275.

(56) References Cited

OTHER PUBLICATIONS

Parisi, Raymond C, "Motion Facilitating Tibial Components for a Knee Prosthesis", U.S. Appl. No. 13/229,103, filed Sep. 9, 2011, 46 pgs.
Stilling, et al., "Superior fixation of pegged trabecular metal over screw-fixed pegged porous titanium fiber mesh", Acta Orthopaedica., (2011), 177-186.
Wentorf, Mary S. S, "Asymmetric Tibial Components for a Knee Prosthesis", U.S. Appl. No. 13/189,338, filed Jul. 22, 2011, 58 pgs.
Wentorf, Mary S. S, "Asymmetric Tibial Components for a Knee Prosthesis", U.S. Appl. No. 13/189,339, filed Jul. 22, 2011, 52 pgs.
Wentorf, Mary S. S, "Asymmetric Tibial Components for a Knee Prosthesis", U.S. Appl. No. 13/189,336, filed Jul. 22, 2011, 60 pgs.
"U.S. Appl. No. 15/267,793, Non Final Office Action dated Jun. 14, 2018", 12 pgs.
"U.S. Appl. No. 15/267,793, Response filed Apr. 11, 2018 to Restriction Requirement dated Feb. 16, 2018", 8 pgs.
"U.S. Appl. No. 15/267,793, Response filed Aug. 22, 2018 Non Final Office Action dated Jun. 14, 2018", 16 pgs.
"U.S. Appl. No. 15/703,678, Restriction Requirement dated Nov. 5, 2018", 6 pgs.
"U.S. Appl. No. 15/703,713, Notice of Allowance dated Sep. 25, 2018", 11 pgs.
"U.S. Appl. No. 15/703,713, Response filed Jun. 15, 2018 to Non-Final Office Action dated Mar. 27, 2018", 16 pgs.
"U.S. Appl. No. 15/827,654, Non Final Office Action dated Sep. 7, 2018", 21 pgs.
"U.S. Appl. No. 15/827,654, Response filed Jun. 6, 2018 to Restriction Requirement dated Apr. 6, 2018", 11 pgs.
"U.S. Appl. No. 15/827,654, Restriction Requirement dated Apr. 6, 2018", 6 pgs.
"Canadian Application Serial No. 2,806,321, Office Action dated Jan. 15, 2018", 3 pgs.
"Canadian Application Serial No. 2,806,321, Response filed Jan. 22, 2018 to Office Action dated Jan. 15, 2018", 7 pgs.
"Canadian Application Serial No. 2,806,321, Response filed Dec. 6, 2017 to Office Action dated Jun. 15, 2017", 12 pgs.
"Canadian Application Serial No. 2,806,326, Examiner's Rule 30(2) Requisition dated Sep. 20, 2018", 4 pgs.
"Canadian Application Serial No. 2,806,326, Response filed Jul. 20, 2018 to Office Action dated Feb. 8, 2018", 12 pgs.
"Canadian Application Serial No. 2,863,375, Office Action dated Apr. 20, 2018", 3 pgs.
"Canadian Application Serial No. 2,863,375, Response filed Office Action dated Apr. 20, 2018", 12 pgs.
"Canadian Application Serial No. 2,956,119, Examiner's Rule 30(2) Requisition dated Sep. 27, 2018", 4 pgs.
"Canadian Application Serial No. 2,989,184, Office Action dated Oct. 1, 2018", 4 pgs.
"Chinese Application Serial No. 201610634595.5, Office Action dated Apr. 20, 2018", (W/ English Translation), 8 pgs.
"Chinese Application Serial No. 201610634595.5, Response filed Jun. 4, 2018 to Office Action dated Apr. 20, 2018", (W/ English Translation of Claims), 8 pgs.
"European Application Serial No. 15160934.4, Communication Pursuant to Article 94(3) EPC dated Apr. 26, 2018", 5 pgs.
"European Application Serial No. 15160934.4, Response filed Aug. 30, 2018 to Communication Pursuant to Article 94(3) EPC dated Apr. 26, 2018", 63 pgs.
"European Application Serial No. 15191781.2, Response filed May 17, 2018 to Communication Pursuant to Article 94(3) EPC dated Jan. 8, 2018", 58 pgs.
"European Application Serial No. 16189084.3, Response filed May 10, 2018 to Extended European Search Report dated Oct. 9, 2017", 20 pgs.
"European Application Serial No. 17163432.2, Extended European Search Report dated May 14, 2018", 6 pgs.
"European Application Serial No. 17168095.2, Extended European Search Report dated Jun. 8, 2018", 8 pgs.
"European Application Serial No. 17168308.9, Extended European Search Report dated Jun. 13, 2018", 8 pgs.
"International Application Serial No. PCT/US2016/052163, International Preliminary Report on Patentability dated Apr. 5, 2018", 10 pgs.
"International Application Serial No. PCT/US2018/021571, International Search Report dated Jun. 7, 2018", 6 pgs.
"International Application Serial No. PCT/US2018/021571, Written Opinion dated Jun. 7, 2018", 6 pgs.
"Australian Application Serial No. 2017235987, First Examination Report dated Nov. 1, 2018", 4 pgs.
"European Application Serial No. 16770657.1, Response filed Nov. 26, 2018 to Office Action dated May 14, 2018", 17 pgs.

* cited by examiner

TIBIAL BASEPLATE WITH ASYMMETRIC PLACEMENT OF FIXATION STRUCTURES

CROSS-REFERENCE TO RELATED APPLICATIONS

This application is a continuation of U.S. patent application Ser. No. 15/045,799 filed on Feb. 17, 2016, which is a continuation of U.S. patent application Ser. No. 14/278,805 filed on May 15, 2014, now issued as U.S. Pat. No. 9,308,096, which is a continuation of U.S. patent application Ser. No. 13/593,339 filed on Aug. 23, 2012, now issued as U.S. Pat. No. 8,758,444, which claims the benefit under Title 35 U.S.C. § 119(e) of U.S. Provisional Patent Application Ser. No. 61/562,133 filed Nov. 21, 2011, U.S. Provisional Patent Application Ser. No. 61/592,571 filed Jan. 30, 2012, U.S. Provisional Patent Application Ser. No. 61/594,030 filed Feb. 2, 2012, and U.S. Provisional Patent Application Ser. No. 61/621,369 filed Apr. 6, 2012, each entitled TIBIAL BASEPLATE WITH ASYMMETRIC PLACEMENT OF FIXATION STRUCTURES and U.S. Provisional Patent Application Ser. No. 61/592,574 filed Jan. 30, 2012 and U.S. Provisional Patent Application Ser. No. 61/621,374 filed Apr. 6, 2012, both entitled ASYMMETRIC TIBIAL COMPONENTS FOR A KNEE PROSTHESIS. The entire disclosures of all of the above-identified patent applications are hereby expressly incorporated by reference herein.

FIELD OF THE DISCLOSURE

The present disclosure relates to orthopaedic prostheses and, more particularly, to tibial baseplate components in a knee prosthesis.

BACKGROUND OF THE DISCLOSURE

Orthopaedic prostheses are commonly utilized to repair and/or replace damaged bone and tissue in the human body. For a damaged knee, a knee prosthesis may be implanted using a proximal tibial baseplate component, a tibial bearing component, and a distal femoral component. The tibial baseplate component is affixed to a proximal end of the patient's tibia, which is typically resected to accept the baseplate component. The femoral component is implanted on a distal end of the patient's femur, which is also typically resected to accept the femoral component. The tibial bearing component is placed between the tibial baseplate component and the femoral component, and may be fixed or slidably coupled to the tibial baseplate component.

The tibial baseplate component provides support for the tibial bearing component. Forces generated by use of the knee prosthesis are transferred through the tibial bearing component to the tibial baseplate component, and ultimately to the tibia. In order to ensure long term performance of the knee prosthesis, stable and firm securement of the tibial baseplate component to the proximal end of the patient's tibia is desired.

SUMMARY

This application is related to U.S. Provisional Patent Application Ser. No. 61/562,133, filed Nov. 21, 2011, to U.S. Provisional Patent Application Ser. No. 61/592,571, filed Jan. 30, 2012, and to U.S. Provisional Patent Application Ser. No. 61/594,030, filed Feb. 2, 2012, the entire disclosures of which are hereby expressly incorporated by reference herein.

The present disclosure provides an orthopaedic knee prosthesis including a tibial baseplate component having a distal, bone-contacting surface with one or more fixation structures extending distally therefrom, the fixation structures being asymmetrically arranged within the outer periphery of the baseplate.

For designs utilizing a plurality of fixation pegs that extend distally from the bone-contacting surface of the tibial baseplate, fixation pegs are asymmetrically arranged in opposite anterior/lateral and posterior/medial regions of the tibial baseplate, thereby maximizing distance between the fixation pegs, avoiding overlap with the intramedullary canal, avoiding areas of low bone density, and avoiding cortical impingement by positioning the fixation pegs in regions of cancellous bone.

For designs utilizing a single keel that extends distally from the bone-contacting surface of the tibial baseplate, the keel is medialized with respect to the outer periphery of the tibial baseplate, where the degree of medialization increases as prosthesis sizes grow progressively.

According to an embodiment thereof, the present disclosure provides a tibial prosthesis system comprising: a first tibial baseplate comprising: a first proximal surface; a first distal surface opposite the first proximal surface, the first distal surface sized and shaped to substantially cover a proximal resected surface of a tibia; a first medial face; a first lateral face opposite the first medial face; a first total width measured from the first medial face to the first lateral face; and a first keel extending distally from the first distal surface, the first keel spaced from the first medial face by a first medial distance and spaced apart from the first lateral face by a first lateral distance; and a second tibial baseplate comprising: a second proximal surface; a second distal surface opposite the second proximal surface, the second distal surface sized and shaped to substantially cover a proximal resected surface of a tibia; a second medial face; a second lateral face opposite the second medial face; a second total width measured between the second medial face and the second lateral face, the second total width differing from the first total width whereby the first and second tibial baseplates comprise unique nominal sizes; and a second keel extending distally from the second distal surface, the second keel spaced apart from the second medial face by a second medial distance and spaced apart from the second lateral face by a second lateral distance, a first ratio of the first medial distance to the first total width differing from a second ratio of the second medial distance to the second total width.

According to another embodiment thereof, the present disclosure provides a tibial baseplate configured for implantation upon a patient's proximal tibia, the tibial baseplate comprising: a medial compartment; a lateral compartment opposite the medial compartment; a proximal surface; a distal surface opposite the proximal surface, the distal surface sized and shaped to substantially cover the patient's proximal tibia; an outer periphery cooperatively defined by an anterior face, a medial face, a lateral face, and at least one posterior face; a first, anterior-posterior axis located between the medial face and the lateral face and intersecting the anterior face, the first axis extending centrally between the medial and lateral compartments throughout its length; a plurality of fixation pegs extending distally from the distal surface, each of the plurality of fixation pegs being positioned inward of the outer periphery for implantation into the patient's proximal tibia, the plurality of fixation pegs comprising: a medial fixation peg located at the medial compartment; and a lateral fixation peg located at the lateral compartment, the lateral fixation peg being positioned more anteriorly than each other fixation peg among the plurality of fixation pegs.

According to yet another embodiment thereof, the present disclosure provides a tibial baseplate configured for implantation upon a patient's proximal tibia, the tibial baseplate comprising: a medial compartment; a lateral compartment opposite the medial compartment; a proximal surface; a distal surface opposite the proximal surface, the distal surface sized and shaped to substantially cover the patient's proximal tibia; an outer periphery cooperatively defined by an anterior face, a medial face, a lateral face, and at least one posterior face; at most one medial fixation peg associated with the medial compartment, the medial fixation peg extending distally from the distal surface and positioned for implantation into the patient's proximal tibia; and at most one lateral fixation peg associated with the lateral compartment, the lateral fixation peg extending distally from the distal surface and positioned for implantation into the patient's proximal tibia, the lateral fixation peg being located closer to the anterior face than the medial fixation peg.

According to still another embodiment thereof, the present disclosure provides a tibial baseplate configured for implantation upon a patient's proximal tibia, the tibial baseplate comprising: a medial compartment; a lateral compartment opposite the medial compartment; a proximal surface; a distal surface opposite the proximal surface, the distal surface sized and shaped to substantially cover the patient's proximal tibia; an outer periphery cooperatively defined by an anterior face, a medial face, a lateral face, and at least one posterior face; a first, anterior-posterior axis located between the medial face and the lateral face and intersecting the anterior face, the first axis extending centrally between the medial and lateral compartments throughout its length; a first fixation peg extending distally from the distal surface, the first fixation peg being inset from the outer periphery for implantation into the patient's proximal tibia, the first fixation peg being medially spaced from the first axis by a first distance; and a second fixation peg extending distally from the distal surface, the second fixation peg being inset from the outer periphery for implantation into the patient's proximal tibia, the second fixation peg being laterally spaced from the first axis by a second distance, the second distance less than the first distance.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure provides a tibial baseplate component for a knee prosthesis including asymmetrically arranged distal fixation structures which promote secure and stable long term fixation of the tibial baseplate to a patient's proximal tibia.

Figure 1:
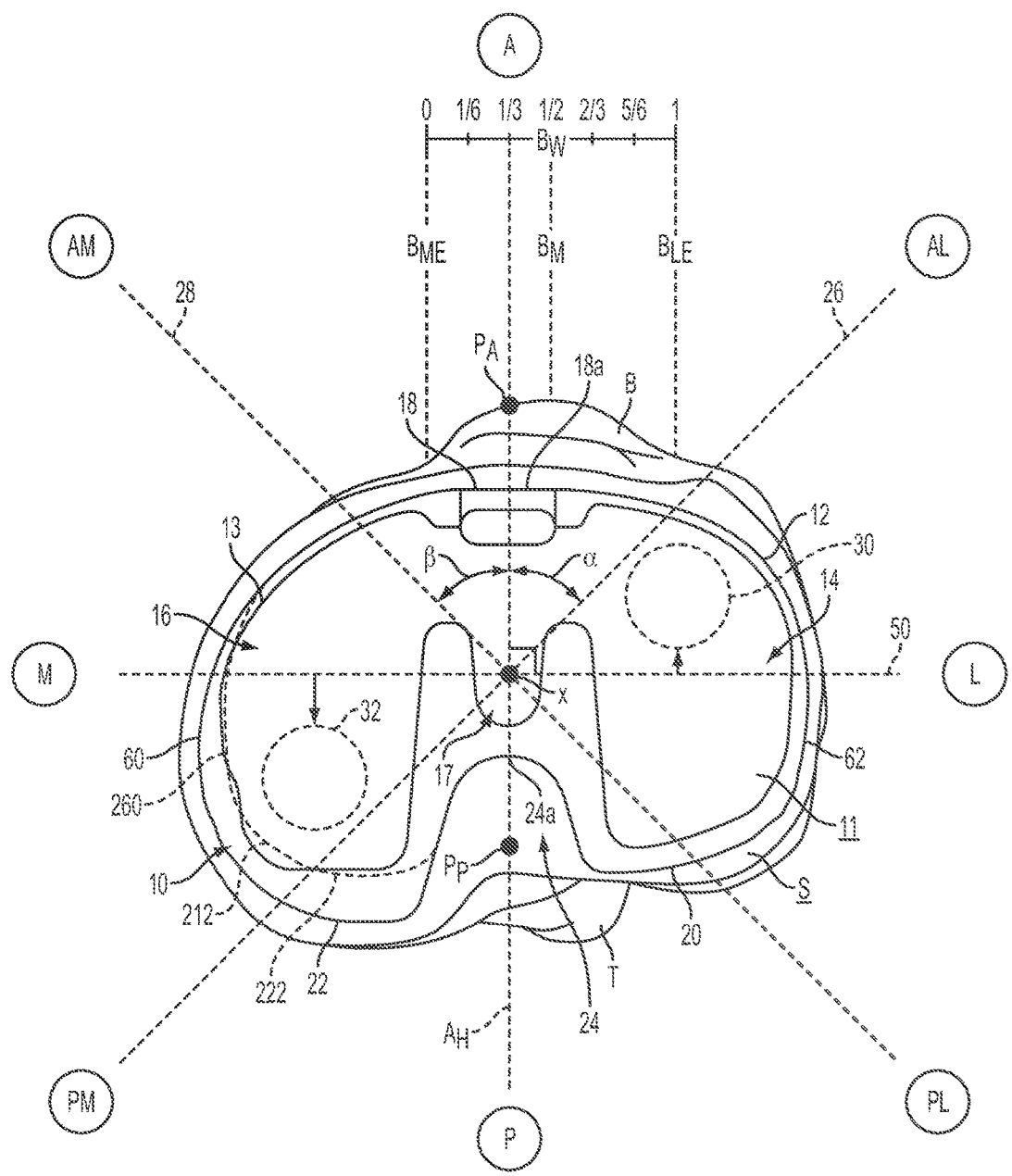
FIG. 1 is a proximal plan view of a tibial baseplate made in accordance with the present disclosure, the baseplate having a lateral fixation peg and a medial fixation peg, the baseplate shown implanted upon the resected proximal surface of a patient's tibia, the baseplate shown having an asymmetric outer periphery in solid lines and a symmetric outer periphery in phantom.

In order to prepare the tibia and femur for receipt of a knee joint prosthesis of the present disclosure, any suitable methods or apparatuses for preparation of the knee joint may be used. The surgical procedure may involve, for example, forming an incision in the patient's skin near the knee joint, resecting the distal end of the patient's femur (not shown), and resecting the proximal end of the patient's tibia T (FIG. 1). Resecting the proximal end of the patient's tibia T (FIG. 1), in particular, may involve guiding a saw blade through an appropriate cutting guide slot to form a substantially planar resected surface S of tibia T, as shown in FIG. 1.

Exemplary surgical procedures and associated surgical instruments are disclosed in Zimmer's "LPS-Flex Fixed Bearing Knee, Surgical Technique" bearing copyright dates of 2004, 2007 and 2008, "NexGen® Complete Knee Solution, Surgical Technique for the CR-Flex Fixed Bearing Knee" bearing a copyright date of 2003, "NexGen® Complete Knee Solution Extramedullary/Intramedullary Tibial Resector, Surgical Technique" bearing copyright dates of 2000, 2008 and 2009, "NexGen® Trabecular Metal™ Monoblock Tibial Components, Surgical Technique Addendum," bearing copyright dates of 2005 and 2007, "NexGen® Trabecular Metal™ Tibial Tray, Surgical Technique," bearing copyright dates of 2007 and 2009, and "Trabecular Metal™ Monoblock Tibial Components," bearing a copyright date of 2007 (collectively, the "Zimmer Surgical Techniques"), the entire disclosures of which are hereby expressly incorporated herein by reference, copies of which are submitted on even date herewith in an Information Disclosure Statement.

As used herein, "proximal" refers to a direction generally toward the torso of a patient, and "distal" refers to the opposite direction of proximal (i.e., away from the torso of a patient). "Anterior" refers to a direction generally toward the front of a patient or knee, and "posterior" refers to the opposite direction of anterior (i.e., toward the back of the patient or knee). "Lateral" refers to a direction generally away from the middle of the patient and the sagittal plane, and "medial" refers to the opposite direction of lateral (i.e., toward the middle of the patient and the sagittal plane). When referring to one of the patient's knees, "lateral" refers to the direction generally away from the other knee, and "medial" refers to the direction generally toward the other knee.

These anatomical regions are labeled in certain drawings for clarity. In FIG. 1, for example, the anterior region of tibia T is labeled "A," the posterior region of tibia T is labeled "P," the lateral region of tibia T is labeled "L," and the medial region of tibia T is labeled "M." Therebetween and moving in a clock-wise direction, the anterior/lateral region of tibia T is labeled "AL," the posterior/lateral region of tibia T is labeled "PL," the posterior/medial region of tibia T is labeled "PM," and the anterior/medial region of tibia T is labeled "AM." The AL, PL, PM, and AM regions can be described as dividing tibia T into four corners or quadrants. These labels are referenced throughout the following paragraphs.

The embodiments shown and described herein illustrate components for a right knee prosthesis. Right and left knee prosthesis configurations are generally mirror images of one another about a sagittal plane. Thus, it will be appreciated that the aspects of the prosthesis described herein for a right knee configuration are equally applicable to a left knee configuration.

1. Tibial Baseplate

Figure 14:
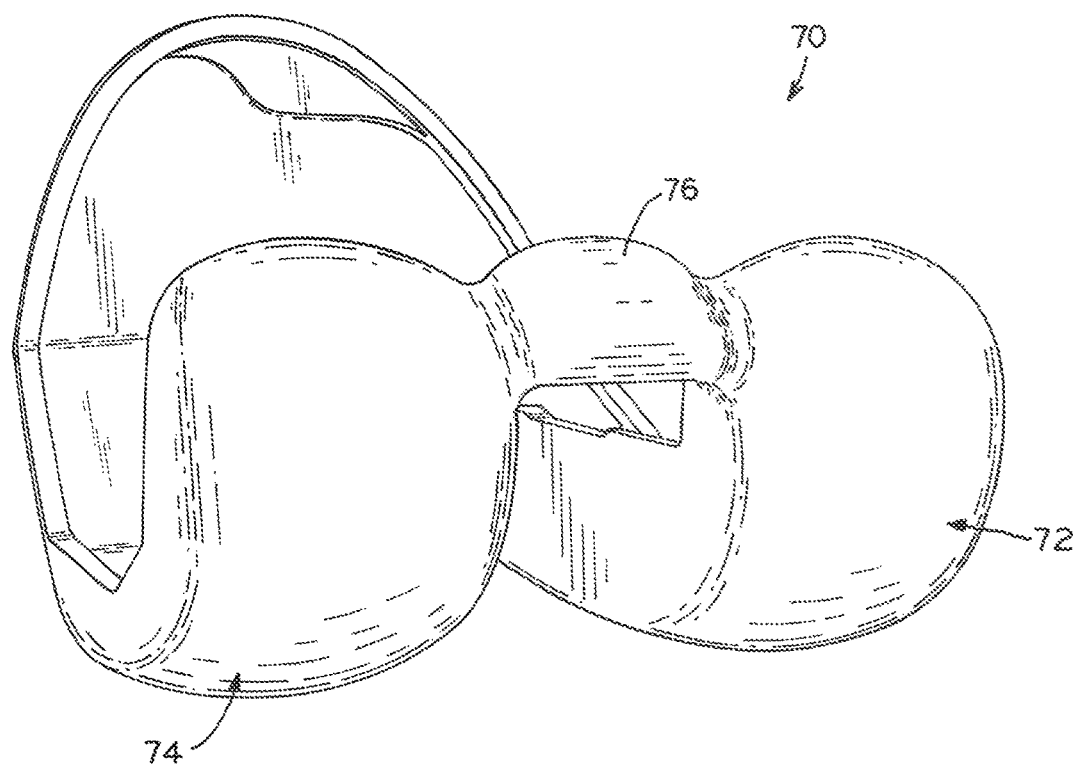
FIG. 14 is a perspective view of a posterior-stabilized femoral component in accordance with the present disclosure.

Referring now to FIG. 1, tibial baseplate 10 is shown disposed atop a proximal resected surface S of a patient's tibia T. The upper or proximal surface 11 of baseplate 10 is shown in FIG. 1. This proximal surface 11 of baseplate 10 is configured to receive a tibial bearing component 53 (FIG. 7) in a fixed or a sliding relationship, for example. To arrange baseplate 10 and the tibial bearing component 53 in a fixed relationship, the tibial bearing component 53 may be adhered to, mechanically fastened to, molded directly onto (as discussed further below), or otherwise fixedly coupled to baseplate 10. The illustrative baseplate 10 includes a raised rim 13 around proximal surface 11 to receive, surround, and hold the tibial bearing component 53 therein, but it is contemplated that other structures may be provided on baseplate 10 to receive and hold the tibial bearing component 53 on baseplate 10. In turn, tibial bearing component 53 is configured to interact with the patient's distal femur or a prosthetic femoral component, such as femoral component 70 shown in FIG. 14 and described below.

Baseplate 10 may be partially or entirely constructed of a highly porous biomaterial. A highly porous biomaterial is useful as a bone substitute and as cell and tissue receptive material. A highly porous biomaterial may have a porosity as low as 55%, 65%, or 75% or as high as 80%, 85%, or 90%. An example of such a material is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 to Kaplan, the entire disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%, 85%, or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of baseplate 10 to the patient's bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

Bearing component 53 may be molded directly onto baseplate 10, specifically proximal surface 11 of baseplate 10. If baseplate 10 is constructed of a highly porous biomaterial, as discussed above, the material that is used to construct bearing component 53 (e.g., polyethylene) may interdigitate into the pores of baseplate 10 during the molding process. The pores may be located at and beneath proximal surface 11 of baseplate 10, so the resulting molded bearing component 53 may also be located at and beneath proximal surface 11 of baseplate 10. The resulting structure may be a monoblock component having a strong, wear-resistant connection between baseplate 10 and bearing component 53, especially along proximal surface 11 of baseplate 10.

Baseplate 10 includes outer periphery 12, which may be visible in a top plan view (FIG. 1) or a bottom plan view (FIGS. 2A-2C) with baseplate 10 positioned in a generally transverse anatomical plane. As shown in FIG. 1, outer periphery 12 is cooperatively defined by anterior face 18, posterior/lateral face 20, posterior/medial face 22, PCL cutout area 24, lateral face 62, and medial face 60. Each of these surfaces is described further below.

Baseplate 10 also includes lateral compartment 14, medial compartment 16, and interior compartment 17 therebetween. Lateral compartment 14 and medial compartment 16 are separated by an anterior-posterior home axis $A_H$, which is discussed further below. Because FIG. 1 is a proximal view of the patient's right tibia T, lateral compartment 14 of baseplate 10 is located on the right side of FIG. 1 and medial compartment 16 of baseplate 10 is located on the left side of FIG. 1.

Figure 7:
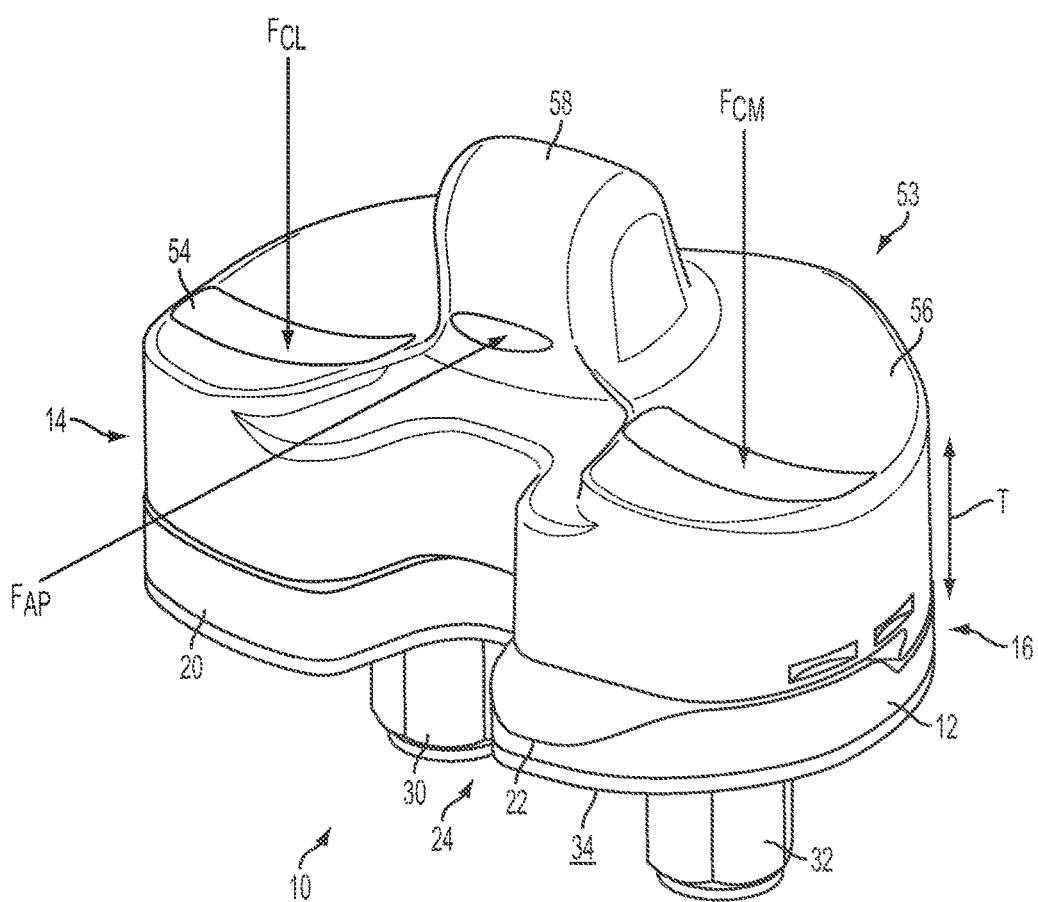
FIG. 7 is a posterior perspective view of the baseplate of FIG. 1, shown with a tibial bearing component mounted thereon.

With bearing component 53 in place against baseplate 10 (FIG. 7) to articulate with adjacent femoral component 70, for example, lateral compartment 14 of baseplate 10 will be positioned generally beneath lateral condyle 74 of femoral component 70 to support and articulate with lateral condyle 74, and medial compartment 16 of baseplate 10 will be positioned generally beneath medial condyle 72 of femoral component 70 to support medial condyle 72. Tibial bearing component 53 (FIG. 7) may be disposed between medial and lateral condyles 72, 74 of femoral component 70 and medial and lateral compartments 16, 14 to provide a low-friction articular interface, as described below. In the illustrative embodiment, femoral component 70 includes cam 76 adapted to articulate with a spine of a tibial bearing component, e.g., spine 58 of tibial bearing component 53 (FIG. 7). However, it is contemplated that femoral component 70 may omit spine 76 to provide an uninterrupted space between medial and lateral condyles 72, 74 in some prosthesis designs.

Anterior face 18 of the illustrative baseplate 10 is disposed anteriorly on periphery 12 of baseplate 10 (i.e., in the A region of tibia T). Anterior face 18 is generally centrally located between lateral and medial compartments 14, 16. More specifically, as shown in FIG. 1, anterior face 18 includes a linear or flat portion 18a that is generally centrally located between lateral and medial compartments 14, 16. In this illustrated embodiment, flat portion 18a of anterior face 18 defines the anterior-most extent of baseplate 10.

Posterior/lateral face 20 of the illustrative baseplate 10 is disposed generally opposite anterior face 18 in the posterior region of lateral compartment 14 (i.e., near the PL region of tibia T). Posterior/medial face 22 of the illustrative baseplate 10 is disposed generally opposite anterior face 18 in the posterior region of medial compartment 16 (i.e., near the PM region of tibia T). The PCL cutout area 24 is disposed between posterior/lateral face 20 and posterior/medial face 22 (i.e., near the P region of tibia T). From both posterior/lateral face 20 and posterior/medial face 22, the PCL cutout area 24 extends generally anteriorly until reaching apex 24a.

Lateral face 62 of the illustrative baseplate 10 is disposed laterally of lateral compartment 14 on periphery 12 of baseplate 10 (i.e., near the L region of tibia T). Medial face 60 of the illustrative baseplate 10 is located medially of medial compartment 16 on periphery 12 of baseplate 10 (i.e., near the M region of tibia T).

2. Home Axis and Other Reference Axes of Tibial Baseplate

In the context of patient anatomy, such as tibia T described herein, "home axis" $A_H$ of tibia T extends anteriorly from a posterior point $P_P$ on tibia T to an anterior point $P_A$ on tibia T. The posterior point $P_P$ and the anterior point $P_A$ of tibia T are discussed further below.

The posterior point $P_P$ is generally disposed in the area where the patient's posterior cruciate ligament (PCL) attaches to tibia T. More specifically, the posterior point $P_P$ is generally disposed at the geometric center of the attachment between the patient's PCL and tibia T. The patient's PCL typically attaches to tibia T in two ligament "bundles," the first bundle having a more anterolateral attachment location and the second bundle having a more posteromedial attachment location. In FIG. 1, the posterior point $P_P$ is shown at the geometric center of the first bundle. It is also within the scope of the present disclosure that the posterior point $P_P$ may be located at the geometric center of the second bundle or at the geometric center of the first and second bundles, together.

The anterior point $P_A$ is disposed on the patient's anterior tibial tubercle B. In FIG. 1, the anterior point $P_A$ is medially spaced from the tubercle midpoint $B_M$ (at marking ½) by an amount equal to ⅙ of the overall medial/lateral tubercle width $B_W$ (which spans between markings 0 and 1). Stated another way, the anterior point $P_A$ is laterally spaced from the tubercle medial end $B_{ME}$ (at marking 0) by an amount equal to ⅓ of the overall medial/lateral tubercle width $B_W$ (which spans between markings 0 and 1), such that the anterior point $P_A$ lies on the "medial third" of the anterior tibial tubercle B (at marking ⅓).

In the context of a prosthesis, such as tibial baseplate 10 described herein, "home axis" $A_H$ of baseplate 10 refers to an anterior-posterior extending axis of baseplate 10 that aligns with home axis $A_H$ of tibia T upon implantation of baseplate 10 onto resected surface S of tibia T in a proper rotational and spatial orientation (as shown in FIG. 1). According to an exemplary embodiment of the present disclosure, and as shown in FIG. 1, home axis $A_H$ of baseplate 10 is centrally located between the inner-most portion of lateral compartment 14 and the inner-most portion of medial compartment 16 of baseplate 10 throughout its length. In other words, home axis $A_H$ of baseplate 10 is equidistant from the inner-most portion of lateral compartment 14 and the inner-most portion of medial compartment 16 of baseplate 10 to divide the interior compartment 17 therebetween into substantially equal halves.

In the illustrative embodiment of FIG. 1, home axis $A_H$ of baseplate 10 bisects anterior face 18 of baseplate 10 (which is located anteriorly on periphery 12 of baseplate 10) and is generally perpendicular to flat portion 18a of anterior surface 18. Also, home axis $A_H$ of baseplate 10 bisects PCL cutout area 24 of baseplate 10 (which is located posteriorly on periphery 12 of baseplate 10) and is generally perpendicular to apex 24a of PCL cutout area 24. It is contemplated that home axis $A_H$ of baseplate 10 may be oriented to other features of baseplate 10, it being understood that proper alignment and orientation of baseplate 10 upon resected surface S of tibia T will position home axis $A_H$ of baseplate 10 coincident with home axis $A_H$ of tibia T.

The home axes $A_H$ of tibia T and baseplate 10 are further described in U.S. Patent Application Publication No. 2012/0022659, filed Jul. 22, 2011, entitled "ASYMMETRIC TIBIAL COMPONENTS FOR A KNEE PROSTHESIS," the entire disclosure of which is hereby expressly incorporated herein by reference.

A pair of reference axes 26, 28 is presented in FIG. 1. A first reference axis 26 extends diagonally across baseplate 10 from the back-left PM region of tibia T to the front-right AL region of tibia T, intersecting home axis $A_H$ to define a first angle α with home axis $A_H$, as shown in FIG. 1. A second reference axis 28 extends diagonally across baseplate 10 and perpendicularly to the first axis 26 from the back-right PL region of tibia T to the front-left AM region of tibia T, intersecting home axis $A_H$ to define a second angle β with home axis $A_H$, as shown in FIG. 1. The first and second angles α and β are each approximately 45 degrees such that, when combined, the first and second angles α and β together total approximately 90 degrees.

The first and second reference axes 26, 28 illustratively intersect one another and home axis $A_H$ at a common point X within periphery 12 of baseplate 10. According to an exemplary embodiment of the present disclosure, point X is generally centered within periphery 12 of baseplate 10 to maximize the aggregated extent of each reference axis 26, 28 that is located within periphery 12 of baseplate 10 while maintaining the desired first and second angles α and β, as discussed above. Point X is illustratively positioned along home axis $A_H$ between flat portion 18a of anterior face 18 and apex 24a of PCL cutout area 24.

Illustratively, a medial-lateral axis 50 also extends through point X in a direction perpendicular to home axis $A_H$. Together, the medial-lateral axis 50 (e.g., the x-axis) and the anterior-posterior home axis $A_H$ (e.g., the y-axis) cooperate to define a component coordinate system (e.g., an x-y coordinate system) useful for quantifying and identifying certain features of baseplate 10.

3. Shape of Outer Periphery of Tibial Baseplate

According to an exemplary embodiment of the present disclosure, and as shown in FIG. 1, baseplate 10 has an asymmetric outer periphery 12. The asymmetric outer periphery 12 may be designed to closely match the corresponding periphery of resected surface S of tibia T. In the illustrated embodiment of FIG. 1, for example, medial compartment 16 is larger than lateral compartment 14. Medial compartment 16 is wider than lateral compartment 14, so medial face 60 is spaced further apart from the anterior-posterior home axis $A_H$ than lateral face 62. Medial compartment 16 is also deeper than lateral compartment 14, so posterior/medial face 22 is spaced further apart posteriorly from the medial-lateral axis 50 than posterior/lateral face 20. For at least these reasons, the outer periphery 12 of baseplate 10 is asymmetric.

The asymmetric shape of baseplate 10 is further described in U.S. Patent Application Publication No. 2012/0022659, filed Jul. 22, 2011, entitled "ASYMMETRIC TIBIAL COMPONENTS FOR A KNEE PROSTHESIS," the entire disclosure of which is hereby expressly incorporated herein by reference.

It is also within the scope of the present disclosure that baseplate 10 may have a symmetric outer periphery 212, as shown in phantom in FIG. 1. In this embodiment, lateral compartment 14 and medial compartment 16 are the same shape and size. Lateral compartment 14 and medial compartment 16 are the same width, so lateral face 62 and the modified medial face 260 (shown in phantom) are equidistant from the anterior-posterior home axis $A_H$. In this manner, an anterior-posterior axis of symmetry through outer periphery 212 of symmetric baseplate 10 may overlay "home axis" $A_H$ and may serve as a reference for lateral compartment 14, medial compartment 16, lateral face 62, medial face 260, lateral and fixation pegs 30, 32 (described below) and other components of baseplate 10. Thus, in addition to being centered within interior compartment 17 between lateral compartment 14 and medial compartment 16 of the symmetric embodiment of baseplate 10, the anterior-posterior home axis $A_H$ would also be centered between lateral face 62 and the modified medial face 260 (shown in phantom). Lateral compartment 14 and medial compartment 16 also define a common anterior/posterior depth, so posterior/lateral face 20 and the modified posterior/medial face 222 (shown in phantom) are equidistant from the medial-lateral axis 50. Generally, a symmetric outer periphery 212 allows the same baseplate 10 to be implanted onto either a patient's right tibia or left tibia.

4. Fixation Pegs

Figure 2A:
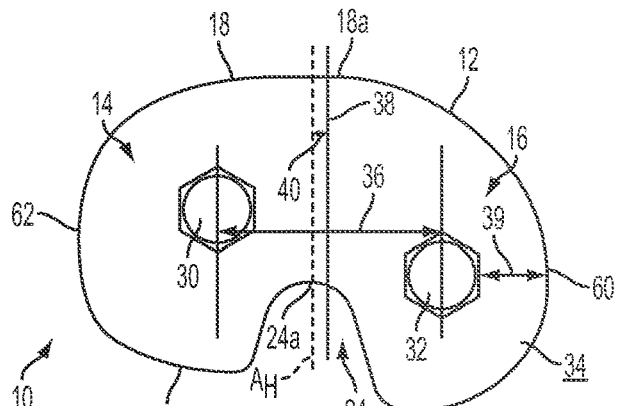
FIG. 2A is a first, distal plan view of the baseplate of FIG. 1, showing medial/lateral positioning of the fixation pegs and the overall medial bias thereof.
Figure 2B:
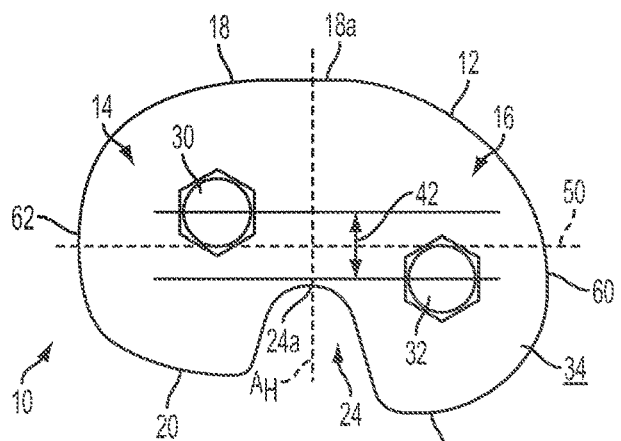
FIG. 2B is a second, distal plan view of the baseplate of FIG. 1 similar to FIG. 2A, showing anterior/posterior positioning of the fixation pegs.
Figure 2C:
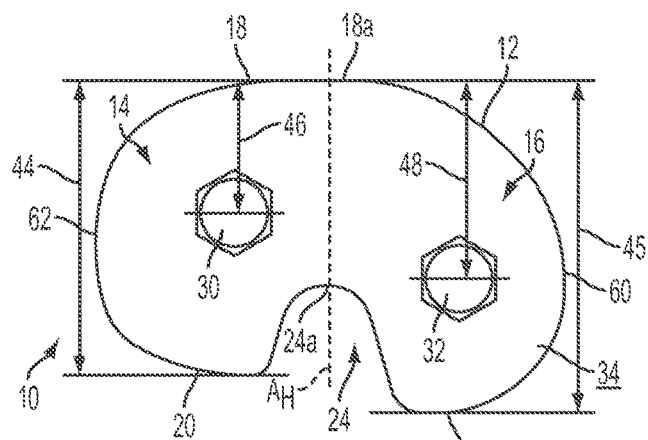
FIG. 2C is a third, distal plan view of the baseplate of FIG. 1 similar to FIGS. 2A and 2B, also showing anterior/posterior positioning of the fixation pegs.
Figure 3:
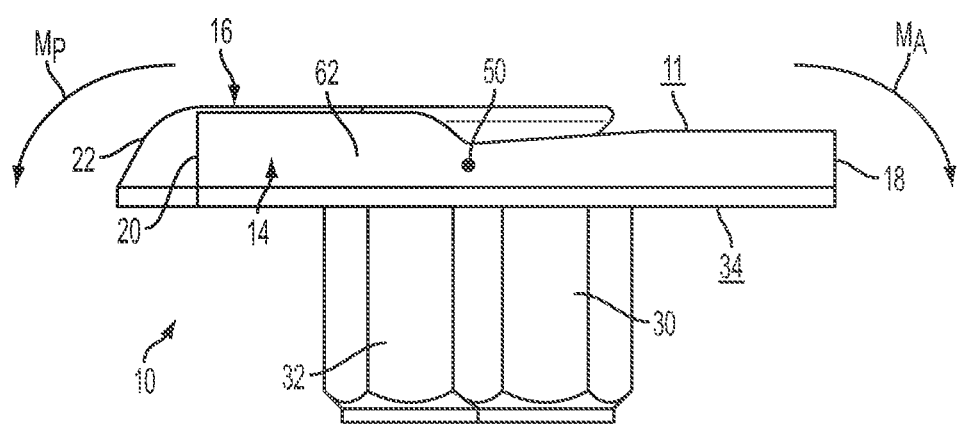
FIG. 3 is a lateral elevational view of the baseplate of FIG. 1.

Referring next to FIGS. 2A-2C and 3, the underside or distal surface 34 of baseplate 10 is shown. Distal surface 34 is the surface which contacts resected surface S of tibia T (FIG. 1) after implantation of baseplate 10. As shown in FIG. 3, distal surface 34 is located opposite proximal surface 11. Baseplate 10 includes a plurality of fixation structures, illustratively lateral fixation peg 30 and medial fixation peg 32, that extend distally from distal surface 34 and into tibia T (FIG. 1).

Each fixation peg 30, 32 is inset from outer periphery 12 of baseplate 10. Each fixation peg 30, 32 may have a minimum inset distance 39 (FIG. 2A) that exceeds 0 mm, such as 1 mm, 3 mm, 5 mm, or more, for example. For purposes of the present disclosure, and as shown in FIG. 2A, the minimum inset distance 39 is the smallest distance measured between outer periphery 12 of baseplate 10 and the outer perimeter of each fixation peg 30, 32.

According to an exemplary embodiment of the present disclosure, fixation pegs 30, 32 of baseplate 10 are constructed of a highly porous biomaterial, such as the above-described porous tantalum material. Distal surface 34 of baseplate 10 may also be constructed of a highly porous biomaterial. With distal surface 34 of baseplate 10 resting against resected surface S of tibia T and fixation pegs 30, 32 of baseplate 10 extending distally into tibia T, the highly porous biomaterial may provide a matrix into which cancellous bone may grow to provide fixation of baseplate 10 to tibia T.

As shown in FIG. 3, the illustrative fixation pegs 30, 32 are hexagonal in cross-section near distal surface 34 of baseplate 10. As fixation pegs 30, 32 continue extending distally away from distal surface 34 of baseplate 10, fixation pegs 30, 32 transition to a circular cross-section. The hexagonal to circular transition of fixation pegs 30, 32 is also evident in FIGS. 2A-2C. In FIG. 1, by contrast, each fixation peg 30, 32 is represented by a phantom circle to schematically show the general location of each fixation peg 30, 32, not necessarily the size or shape of each fixation peg 30, 32. Exemplary fixation pegs 30, 32 are shown at pages 16-19 of the "Zimmer® Tibial Baseplate, Pocket Guide United States Version," the entire disclosure of which is hereby expressly incorporated herein by reference, a copy of which is submitted on even date herewith in an Information Disclosure Statement.

According to an exemplary embodiment of the present disclosure, and as discussed further below, lateral and medial fixation pegs 30, 32 are asymmetrically arranged on distal surface 34 of baseplate 10. In one exemplary embodiment, fixation pegs 30, 32 are asymmetrically arranged about the anterior-posterior home axis $A_H$, such that the anterior-posterior home axis $A_H$ is not an axis of symmetry of fixation pegs 30, 32. In another embodiment, fixation pegs 30, 32 are asymmetrically arranged about the medial-lateral axis 50, such that the medial-lateral axis 50 is not an axis of symmetry of fixation pegs 30, 32. In yet another embodiment, fixation pegs 30, 32 are asymmetrically arranged about both the anterior-posterior home axis $A_H$ and the medial-lateral axis 50, such that neither the anterior-posterior home axis $A_H$ nor the medial-lateral axis 50 is an axis of symmetry of fixation pegs 30, 32.

5. Anterior/Lateral (AL) and Posterior/Medial (PM) Positioning of Fixation Pegs

Returning now to FIG. 1, lateral fixation peg 30 in lateral compartment 14 of baseplate 10 is positioned anteriorly relative to the medial-lateral axis 50 and anteriorly of medial fixation peg 32. Thus, lateral fixation peg 30 is more generally positioned in the AL region of tibia T while being substantially distanced from the PL region of tibia T. The AL bias of lateral fixation peg 30 is evident in FIG. 1, because from the center point X, the first axis 26 extends toward the AL region and approaches or even intersects lateral fixation peg 30, while the second axis 28 extends toward the PL region extends further away from lateral fixation peg 30.

In the medial compartment 16 of baseplate 10, medial fixation peg 32 is positioned posteriorly relative to the medial-lateral axis 50 and posteriorly of lateral fixation peg 30. Thus, medial fixation peg 32 is more generally positioned in the PM region of tibia T while being substantially distanced from the AM region of tibia T. The PM bias of medial fixation peg 32 is evident in FIG. 1, because from the center point X, the first axis 26 extends toward the PM region and approaches or even intersects medial fixation peg 32, while the second axis 28 extends toward the AM region and travels away from medial fixation peg 32. In this exemplary embodiment, both fixation pegs 30, 32 are generally positioned along the same first reference axis 26 which spans the PM and AL regions.

Figure 4:
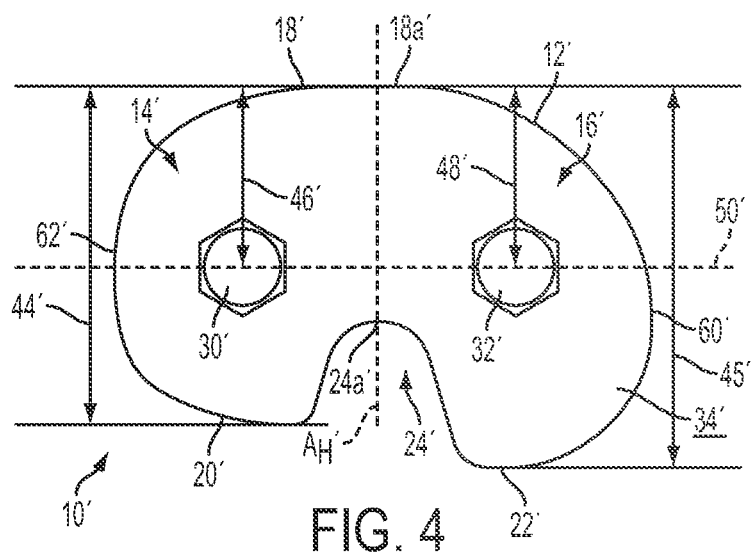
FIG. 4 is a distal plan view of an alternative baseplate.

An alternative baseplate 10' is shown in FIG. 4 for contrast. Outer periphery 12' of the alternative baseplate 10' of FIG. 4 is generally the same as outer periphery 12 of baseplate 10 (shown in solid lines in FIG. 1)—both are asymmetric in shape. However, unlike fixation pegs 30, 32 of FIGS. 2A-2C, which are located on opposite sides of the medial-lateral axis 50, fixation pegs 30', 32' of FIG. 4 are aligned along and intersect with medial-lateral axis 50'. With respect to baseplate 10', both the anterior-posterior home axis $A_H$' and the medial-lateral axis 50' are axes of symmetry for fixation pegs 30', 32', such that fixation pegs 30', 32' may be said to be symmetrically oriented with respect to the component coordinate system.

Figure 5:
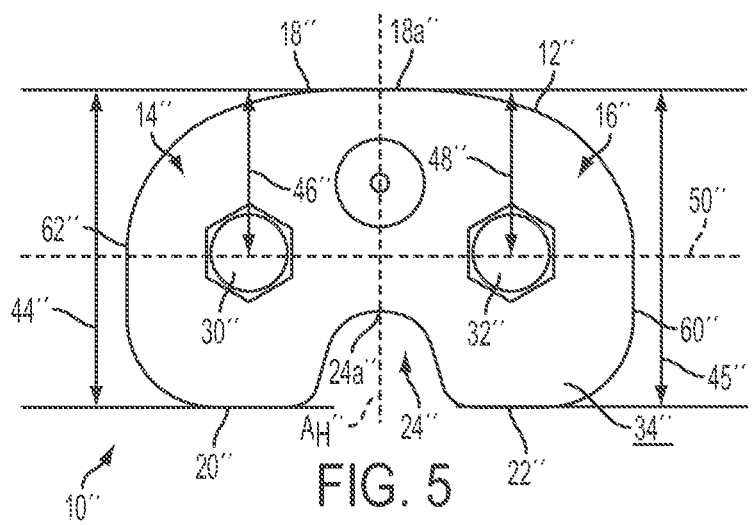
FIG. 5 is a distal plan view of another alternative baseplate.

Another alternative baseplate 10" is shown in FIG. 5 for contrast. Outer periphery 12" of the alternative baseplate 10" of FIG. 5 is generally the same as outer periphery 212 of baseplate 10 (shown in phantom in FIG. 1)—both are symmetric in shape. Lateral compartment 14" of the alternative baseplate 10" is generally the same size and shape as medial compartment 16" of the alternative baseplate 10". Therefore, the anterior-posterior home axis $A_H$" is an axis of symmetry for outer periphery 12" of baseplate 10". Like fixation pegs 30', 32' of FIG. 4, fixation pegs 30", 32" of FIG. 5 are aligned along and intersect with medial-lateral axis 50". With respect to baseplate 10", both the anterior-posterior home axis $A_H$" and the medial-lateral axis 50" are axes of symmetry for fixation pegs 30", 32", such that that fixation pegs 30", 32" may be said to be symmetrically oriented with respect to the component coordinate system.

Returning again to FIG. 1, the asymmetric positioning of lateral and medial fixation pegs 30, 32 near opposite AL and PM corners or quadrants, respectively, allows fixation pegs 30, 32 to be widely spaced apart across distal surface 34 of baseplate 10. Advantageously, this wide spacing facilitates avoidance of the anatomic intramedullary canal of tibia T upon implantation (which may be located near the intersection point X), particularly where baseplate 10 is used for a small-stature patient. By avoiding placement of fixation pegs 30, 32 within the intramedullary canal of tibia T, the associated areas of low bone density are avoided and, instead, fixation pegs 30, 32 may be implanted into areas of higher bone density, thereby promoting firm and stable long-term fixation of tibial baseplate 10 to tibia T. If fixation pegs 30, 32 are constructed of a highly porous biomaterial, as discussed above, this firm and stable long-term fixation may be achieved by cancellous bone growth into the porous fixation pegs 30, 32. Also advantageously, the wide spacing between fixation pegs 30, 32 encourages bone ingrowth therebetween. By contrast, if fixation pegs 30, 32 are too close together, there may not be enough space for bone to grow therebetween.

Also, the asymmetric arrangement of lateral and medial fixation pegs 30, 32 on opposite sides of the medial-lateral axis 50 may enhance the torsional stability of baseplate 10 when implanted upon tibia T (FIG. 1). During normal use, a significant portion of the forces generated on baseplate 10 are directed anteriorly or posteriorly. Activities which primarily generate such anteriorly-directed or posteriorly-directed forces include walking, running, squatting, and climbing stairs, for example. As shown in FIG. 3, such anteriorly-directed and posteriorly-directed forces give rise to anterior torsional moments $M_A$ and posterior torsional moments $M_P$, respectively, which urge rotation of baseplate 10 anteriorly and posteriorly about the medial-lateral axis 50. Having lateral and medial fixation pegs 30, 32 positioned on opposite sides of the medial-lateral axis 50 (i.e., the axis of rotation), as illustrated in FIG. 3 and discussed in detail above, presents greater resistance to such rotation.

Furthermore, positioning lateral and medial fixation pegs 30, 32 in the AL and PM regions of tibia T, rather than the PL and AM regions of tibia T, may avoid impingement of pegs 30, 32 on adjacent cortical bone upon implantation of baseplate 10. Advantageously, the AL and PM regions of tibia T (where fixation pegs 30, 32 are located) are typically populated with substantial areas of cancellous bone, thereby promoting firm and stable long-term fixation of tibial baseplate 10 to tibia T and promoting bone ingrowth. By contrast, the PL and AM regions of tibia T (where fixation pegs 30, 32 are not located) are typically populated with substantial areas of cortical bone. By avoiding the PL and AM regions of tibia T, the potential for impingement of fixation pegs 30, 32 upon cortical bone is minimized.

6. Lateral/Medial Positioning of Fixation Pegs

Because lateral fixation peg 30 extends from lateral compartment 14 and medial fixation peg 32 extends from medial compartment 16, as discussed above, lateral fixation peg 30 can be said to be positioned "more laterally" on distal surface 34 of baseplate 10 than medial fixation peg 32. Similarly, medial fixation peg 32 is positioned "more medially" on distal surface 34 of baseplate 10 than lateral fixation peg 30. Thus, as shown in FIG. 2A, fixation pegs 30, 32 are spaced apart by a medial-lateral separation distance 36. For purposes of the present disclosure, the medial-lateral separation distance 36 is measured on center between fixation pegs 30, 32 along a direction perpendicular to home axis $A_H$ and parallel to medial-lateral axis 50 (FIG. 2B). In an exemplary embodiment, the medial-lateral separation distance 36 is between 20 mm and 55 mm, with smaller separation distances 36 corresponding to smaller nominal prosthesis sizes, and larger separation distances 36 corresponding to larger nominal prosthesis sizes.

According to an exemplary embodiment of the present disclosure, lateral fixation peg 30 and/or medial fixation peg 32 are medially biased in their respective compartments 14, 16. In lateral compartment 14, the illustrative lateral fixation peg 30 is medially biased toward home axis $A_H$. In medial compartment 16, the illustrative medial fixation peg 32 is medially biased away from home axis $A_H$. The medial bias of fixation pegs 30, 32, is evident in FIG. 2A, for example, where central peg axis 38 (which is centered along the medial-lateral separation distance 36 between fixation pegs 30, 32) is medially biased toward medial compartment 16 and away from home axis $A_H$. Because central peg axis 38 is centered along medial-lateral separation distance 36, central peg axis 38 divides medial-lateral separation distance 36 into equal halves—one half being located between lateral fixation peg 30 and central peg axis 38 and the other half being located between medial fixation peg 32 and central peg axis 38.

If fixation pegs 30, 32 were equally spaced apart from home axis $A_H$, central peg axis 38 would coincide with home axis $A_H$. However, in FIG. 2A, pegs 30, 32 are not equally spaced apart from home axis $A_H$. Instead, lateral fixation peg 30 is located closer to home axis $A_H$ than medial fixation peg 32. As a result, central peg axis 38 between fixation pegs 30, 32 is medially spaced or offset toward medial compartment 16 and away from home axis $A_H$ by offset distance 40. Therefore, fixation pegs 30, 32 may be said to be asymmetrically, medially biased relative to home axis $A_H$. In an exemplary embodiment, offset distance 40 is between 3 mm and 6 mm. Smaller prosthesis sizes may have smaller values for offset distance 40, while larger prosthesis sizes may have larger values for offset distance 40.

7. Anterior/Posterior Positioning of Fixation Pegs

As discussed above, lateral fixation peg 30 is positioned relatively more anteriorly on distal surface 34 of baseplate 10 than medial fixation peg 32. Stated differently, medial fixation peg 32 is positioned relatively more posteriorly on distal surface 34 of baseplate 10 than lateral fixation peg 30. Thus, as shown in FIG. 2B, pegs 30, 32 are spaced apart by an anterior-posterior separation distance 42. For purposes of the present disclosure, the anterior-posterior separation distance 42 is measured on center between fixation pegs 30, 32 along a direction parallel to home axis $A_H$. In an exemplary embodiment, the anterior-posterior separation distance 42 is between 5 mm and 11 mm, with smaller separation distances 42 corresponding to smaller prosthesis sizes, and larger separation distances 42 corresponding to larger prosthesis sizes.

The alternative baseplates 10', 10'' of FIGS. 4 and 5 are provided for contrast. Because lateral and medial fixation pegs 30', 32' of the alternative baseplate 10' of FIG. 4, for example, are aligned in an anterior-posterior direction, lateral and medial fixation pegs 30', 32' lack an anterior-posterior separation distance analogous to the anterior-posterior separation distance 42 of FIG. 2B. Or stated differently, lateral and medial fixation pegs 30', 32' have an anterior-posterior separation distance equal to 0 mm. Similarly, lateral and medial fixation pegs 30'', 32'' of the alternative baseplate 10'' of FIG. 5 are aligned in an anterior-posterior direction and, therefore, have an anterior-posterior separation distance equal to 0 mm.

Turning now to FIG. 2C, another way of quantifying the anterior/posterior asymmetry of fixation pegs 30, 32 is by contrasting their different positions relative to a common reference marker. In FIG. 2C, for example, the common reference marker is flat portion 18a of anterior face 18 of baseplate 10, with measurements being taken posteriorly therefrom in a direction parallel to home axis $A_H$. Lateral fixation peg 30 is spaced posteriorly from anterior face 18 by a relatively smaller lateral peg distance 46, while medial fixation peg 32 is spaced posteriorly from anterior face 18 by a relatively larger medial peg distance 48. The lateral anterior/posterior depth 44 of lateral compartment 14 of baseplate 10 is also shown being measured from anterior face 18 to posterior/lateral face 20 of baseplate 10, and this lateral anterior/posterior depth 44 exceeds both peg distances 46, 48. Similarly, medial anterior/posterior depth 45 of medial compartment 16 of baseplate 10 is also shown being measured from anterior face 18 to posterior/medial face 22 of baseplate 10, and medial anterior/posterior depth 45 exceeds both peg distances 46, 48, as well as lateral anterior/posterior depth 44. If baseplate 10 had a symmetric outer periphery 212 (shown in phantom in FIG. 1) instead of the asymmetric outer periphery 12 of FIG. 2C, lateral depth 44 and medial depth 45 would be the same.

The alternative baseplates 10', 10'' of FIGS. 4 and 5 are provided for contrast. Because lateral and medial fixation pegs 30', 32' of the alternative baseplate 10' of FIG. 4, for example, are aligned in an anterior-posterior direction, the lateral peg distance 46' from anterior face 18' to lateral fixation peg 30' is the same as the medial peg distance 48' from anterior face 18' to medial fixation peg 32'. The same is also true for lateral peg distance 46'' and medial peg distance 48'' of the alternative baseplate 10'' of FIG. 5. Because the alternative baseplate 10' of FIG. 4 has an asymmetric outer periphery 12', medial depth 45' differs from lateral depth 44'. Because the alternative baseplate 10'' of FIG. 5 has a symmetric outer periphery 12'', on the other hand, medial depth 45'' is the same as lateral depth 44''.

8. Asymmetric Positioning of Fixation Pegs for Set of Prostheses

Baseplate 10 may be provided in a kit or set of different prosthesis sizes. In one embodiment, nine baseplates 10 are provided in the set, with baseplates 10 growing progressively in lateral anterior/posterior depth 44 and/or other dimensions, for example. The progressive growth of periphery 12 of baseplates 10 across the set or family of baseplate sizes is described in detail in U.S. Patent Application Publication No. 2012/0022660 filed Jul. 22, 2011 and entitled ASYMMETRIC TIBIAL COMPONENTS FOR A KNEE PROSTHESIS, the entire disclosure of which is hereby expressly incorporated herein by reference.

Figure 6:
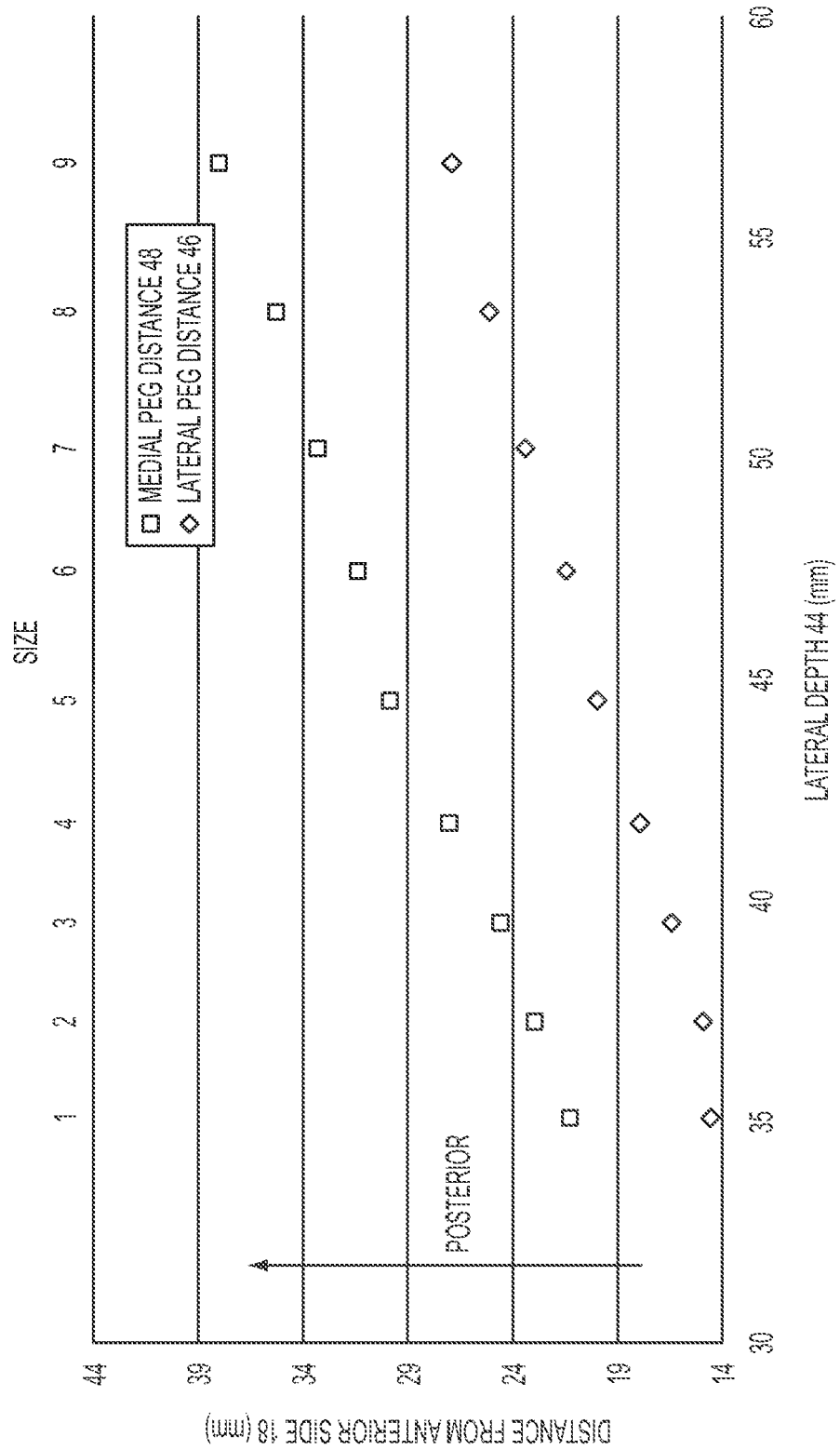
FIG. 6 is a graph illustrating the anterior/posterior positioning of the fixation pegs of FIGS. 1-3 across a range of prosthesis sizes.

Referring next to FIG. 6, exemplary peg distances 46, 48 are graphically presented for a set of prostheses of different sizes. More specifically, exemplary peg distances 46, 48 are graphically presented for a set of prostheses having different lateral depths 44. The vertical axis of FIG. 6 shows peg distances 46, 48 (in millimeters), while the horizontal axis of FIG. 6 shows various lateral depths 44 (also in millimeters) and the corresponding nominal size indicator (1-9). The data points located farther to the left represent smaller lateral depths 44 (and therefore smaller nominal prosthesis sizes), and data points located farther to the right represent larger lateral depths 44 (and therefore larger nominal prosthesis sizes). In accordance with FIG. 2C, peg distances 46, 48 and lateral depth 44 are measured posteriorly from flat portion 18a of anterior face 18.

For each given prosthesis size (i.e., each discrete value of lateral depth 44), a pair of points are presented for lateral and medial peg distances 46, 48, respectively, with a space between the pair of points. This space indicates that peg distances 46, 48 are different for each of the nine given prosthesis sizes. Medial peg distances 48 consistently exceed the corresponding lateral peg distances 46 for each of the nine given prosthesis sizes. For example, each medial peg distance 48 may exceed the corresponding lateral peg distance 46 by 7 mm to 11 mm. In this manner, each of the given prostheses has anterior/posterior asymmetry of fixation pegs 30, 32 with respect to anterior face 18.

FIG. 6 also demonstrates that, as the prosthesis size increases, medial peg distances 48 may increase at a faster rate than lateral peg distances 46. In the illustrated embodiment of FIG. 6, medial peg distances 48 increase at a rate (i.e., slope) of approximately 0.9, while lateral peg distances 46 increase at a rate of approximately 0.6. As a result, the difference between medial peg distance 48 and its corresponding lateral peg distance 46 increases as the prosthesis size increases, causing fixation pegs 30, 32 to become more and more spaced apart as the prosthesis size increases.

With respect to the alternative baseplate 10' of FIG. 4, by contrast, where the lateral peg distance 46' is the same as the medial peg distance 48', the peg distances 46', 48' would overlap graphically in FIG. 6. Thus, for any given prosthesis size, a single point corresponding to both lateral peg distance 46' and medial peg distance 48' would be presented in FIG. 6, without a space therebetween. Also, because fixation pegs 30', 32' of baseplate 10' are aligned along medial-lateral axis 50', and not forward of or behind medial-lateral axis 50' like fixation pegs 30, 32 of baseplate 10, the overlapping peg distances 46', 48' of the alternative baseplate 10' would fall somewhere between the spaced-apart peg distances 46, 48 of FIG. 6. The same result would occur with the overlapping peg distances 46", 48" of the alternative baseplate 10" of FIG. 5.

According to an exemplary embodiment of the present disclosure, the above-described distances, including inset distance 39, medial-lateral separation distance 36, offset distance 40, anterior-posterior separation distance 42, lateral peg distance 46, and medial peg distance 48, are measured along distal surface 34 of baseplate 10. As a result, the distances are measured near the intersection of each peg 30, 32 with distal surface 34 (e.g., near the proximal end of each peg 30, 32). In embodiments where pegs 30, 32 are perpendicular to distal surface 34, the distances could also be measured away from distal surface 34 (e.g., near the distal end of each peg 30, 32) without impacting the measurements. In embodiments where pegs 30, 32 are canted relative to distal surface 34, however, the measurements could vary if taken away from distal surface 34 (e.g., near the distal end of each canted peg 30, 32). Therefore, for consistency, the measurements are taken along distal surface 34 of baseplate 10.

9. Force Testing of Asymmetric Fixation Pegs

A first prosthesis was manufactured, as shown in FIG. 7, by mounting bearing component 53 onto baseplate 10, with baseplate 10 having an asymmetric outer periphery 12 and asymmetrically arranged lateral and medial fixation pegs 30, 32 (FIGS. 1-3). A second prosthesis (not shown) was manufactured by mounting a similar bearing component 53 onto an alternative baseplate 10', with the alternative baseplate 10' having an asymmetric outer periphery 12' but aligned lateral and medial fixation pegs 30', 32' (FIG. 4). A third prosthesis (not shown) was manufactured by mounting a similar bearing component 53 onto another alternative baseplate 10", with the other alternative baseplate 10" having a symmetric outer periphery 12" and aligned lateral and medial fixation pegs 30", 32" (FIG. 5).

The illustrative bearing component 53 has lateral articular surface 54, medial articular surface 56, and spine 58 located therebetween. When bearing component 53 is assembled onto baseplate 10, as shown in FIG. 7, lateral articular surface 54 of bearing component 53 aligns with lateral compartment 14 of baseplate 10, medial articular surface 56 of bearing component 53 aligns with medial compartment 16 of baseplate 10, and spine 58 aligns with interior compartment 17 (FIG. 1) of baseplate 10. For the first and second prostheses, bearing component 53 had a thickness T of 20 mm. For the third prosthesis, bearing component 53 had a thickness T of 17 mm. Bearing component 53 and its associated articular surfaces 54, 56 are described in detail in U.S. Provisional Patent Application Ser. No. 61/561,657, filed Nov. 18, 2011, and are further described in U.S. Provisional Patent Application Ser. No. 61/577,293, filed Dec. 19, 2011, and are further described in U.S. Provisional Patent Application Ser. No. 61/592,576, filed on Jan. 30, 2012, and are further described in U.S. Provisional Patent Application Ser. No. 61/621,361 filed Apr. 6, 2012, and are further described in U.S. Provisional Patent Application Ser. No. 61/621,363 filed Apr. 6, 2012, and are further described in U.S. Provisional Patent Application Ser. No. 61/621,364 filed Apr. 6, 2012, and are further described in U.S. Provisional Patent Application Ser. No. 61/621,366 filed Apr. 6, 2012, and are further described in U.S. patent application Ser. No. 13/459,037 filed Apr. 27, 2012, and are further described in U.S. patent application Ser. No. 13/459,041 filed Apr. 27, 2012, and are further described in U.S. patent application Ser. No. 13/459,048 filed Apr. 27, 2012, and are further described in U.S. patent application Ser. No. 13/459,056 filed Apr. 27, 2012, all entitled "TIBIAL BEARING COMPONENT FOR A KNEE PROSTHESIS WITH IMPROVED ARTICULAR CHARACTERISTICS," the entire disclosures of which are hereby incorporated by reference herein.

As shown in FIG. 7, a lateral compressive force $F_{CL}$ was applied onto lateral articular surface 54 of each bearing component 53, and a medial compressive force $F_{CM}$ was applied onto medial articular surface 56 of each bearing component 53. The compressive forces $F_{CL}$, $F_{CM}$ measured 202 N.

Simultaneously with application of the compressive forces $F_{CL}$, $F_{CM}$, an anterior-facing force $F_{AP}$ was applied to the distal/posterior base of spine 58, as shown in FIG. 7. The anterior-facing force $F_{AP}$ measured 725 N for the first and second prostheses and was scaled up to 791 N for the third prosthesis to account for the thinner bearing component 53.

Forces $F_{CL}$, $F_{CM}$, and $F_{AP}$ were designed in magnitude and area of application to replicate forces exerted on tibial bearing component 53 by a prosthetic femoral component, e.g., femoral component 70, during a kneeling motion. An exemplary femoral component which articulates with tibial bearing component 53 is described in U.S. Provisional Patent Application Ser. No. 61/561,658, filed Nov. 18, 2011, and is further described in U.S. Provisional Patent Application Ser. No. 61/579,873, filed Dec. 23, 2011, and is further described in U.S. Provisional Patent Application Ser. No. 61/592,575, filed on Jan. 30, 2012, and is further described in U.S. Provisional Patent Application Ser. No. 61/594,113 filed on Feb. 2, 2012, and is further described in and in U.S. Provisional Patent Application Ser. No. 61/621,370 filed Apr. 6, 2012, and are further described in U.S. Provisional Patent Application Ser. No. 61/621,372 filed Apr. 6, 2012, and are further described in U.S. Provisional Patent Application Ser. No. 61/621,373 filed Apr. 6, 2012, and are further described in U.S. patent application Ser. No. 13/459,061 filed Apr. 27, 2012, and are further described in U.S. patent application Ser. No. 13/459,064 filed Apr. 27, 2012, and are further described in U.S. patent application Ser. No. 13/459,060 filed Apr. 27, 2012, all entitled "FEMORAL COMPONENT FOR A KNEE PROSTHESIS WITH IMPROVED ARTICULAR CHARACTERISTICS," the entire disclosures of which are hereby expressly incorporated herein by reference.

Finite element analysis was performed on the first, second, and third prostheses to evaluate and compare stresses experienced at the interface of baseplates 10, 10', 10" and a simulated tibial bone that was well fixed to each respective baseplate. Peak stresses experienced in the above-described loading scenario were substantially reduced for the first baseplate 10 having asymmetrically arranged fixation pegs 30, 32 as compared to the second baseplate 10' having aligned fixation pegs 30', 32' and the third baseplate 10" having aligned fixation pegs 30", 32". More particularly, a 51% reduction in peak stress was observed in the first baseplate 10 as compared to the second baseplate 10', and a 46% reduction in peak stress was observed in the first baseplate 10 as compared to the third baseplate 10".

10. Additional Fixation Pegs

Figure 13:
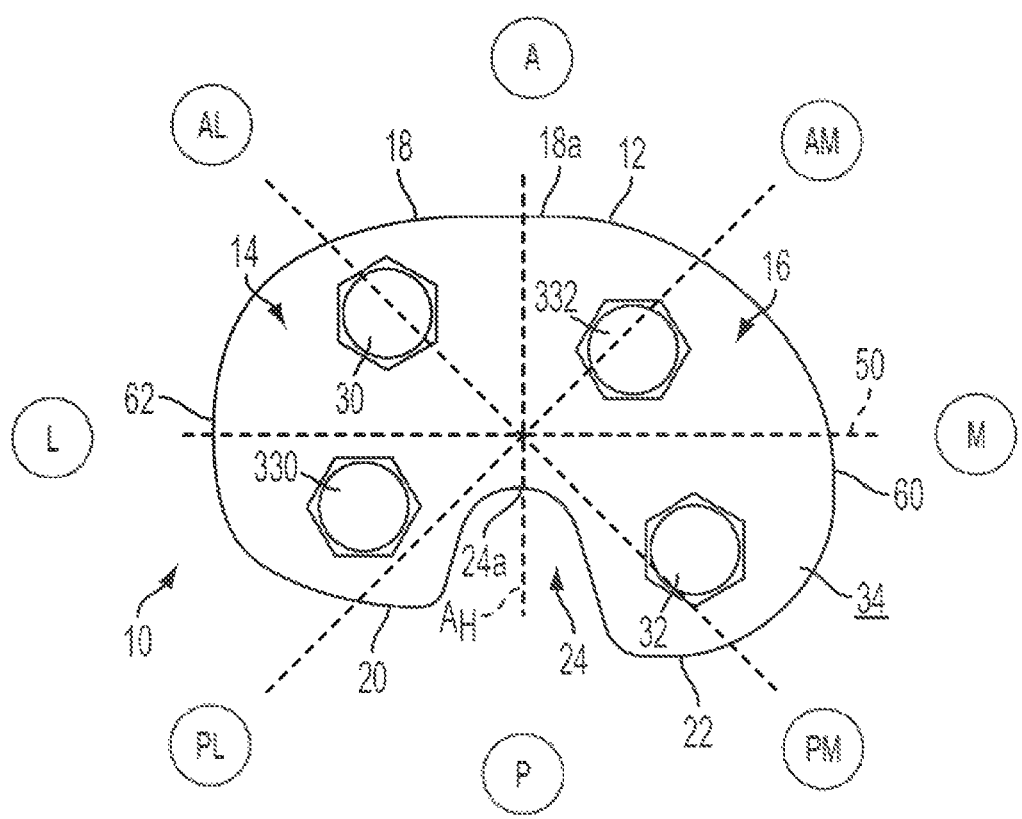
FIG. 13 is a distal plan view of another baseplate similar to the baseplate shown in FIGS. 2A-2C, but having another lateral fixation peg and another medial fixation peg.

In addition to lateral fixation peg 30 described above, lateral compartment 14 of tibial baseplate 100 may further include at least one additional lateral fixation peg 330. As shown in FIG. 13, the additional lateral fixation peg 330 is substantially centered within the PL quadrant. The illustrative lateral fixation peg 330 is positioned anteriorly/posteriorly between lateral fixation peg 30 and medial fixation peg 32, such that lateral fixation peg 30 is the anterior-most fixation peg on tibial baseplate 100 and medial fixation peg 32 is the posterior-most fixation peg on tibial baseplate 100. As a result of lateral fixation peg 30 being medially biased toward home axis $A_H$, as described above, the illustrative lateral fixation peg 330 is located laterally outward of lateral fixation peg 30 and is the lateral-most fixation peg on tibial baseplate 100.

In addition to medial fixation peg 32 described above, medial compartment 16 of tibial baseplate 100 may further include at least one additional medial fixation peg 332. As shown in FIG. 13, the additional medial fixation peg 332 is substantially centered within the AM quadrant. The illustrative medial fixation peg 332 is positioned anteriorly/posteriorly between lateral fixation peg 30 and medial fixation peg 32, such that lateral fixation peg 30 is the anterior-most fixation peg on tibial baseplate 100 and medial fixation peg 32 is the posterior-most fixation peg on tibial baseplate 100. As a result of medial fixation peg 32 being medially biased away from home axis $A_H$, as described above, the illustrative medial fixation peg 332 is located laterally inward of medial fixation peg 32.

11. Fixation Keel

Figure 8:
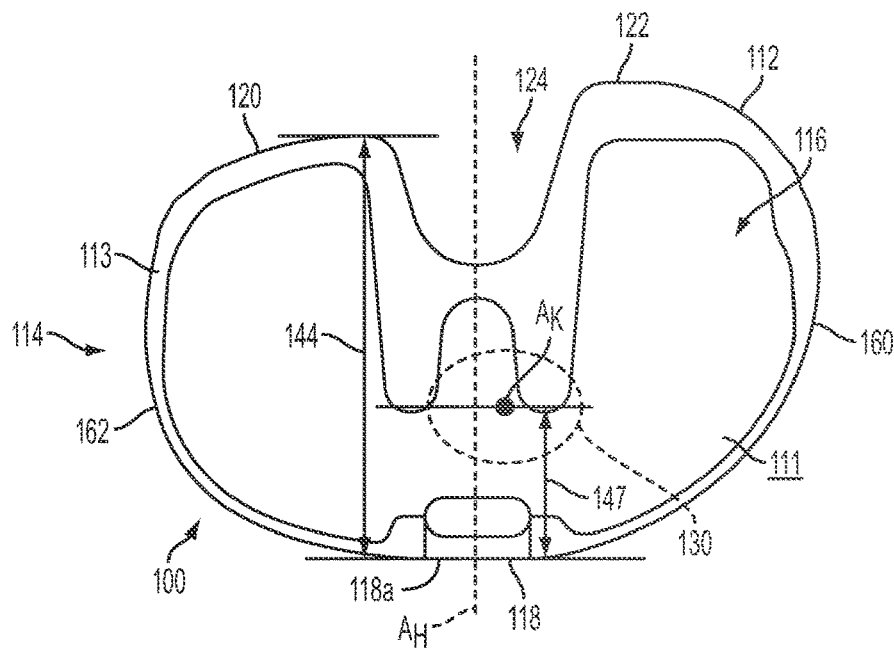
FIG. 8 is a proximal plan view of another tibial baseplate made in accordance with the present disclosure, the baseplate having a single fixation keel for fixation to the patient's tibia.

Turning to FIGS. 8 and 9, tibial baseplate 100 is provided that is substantially similar to baseplate 10 of FIGS. 1-3, except that baseplate 100 includes a single fixation structure, illustratively keel 130, that extends distally from distal surface 134 and into tibia T (FIG. 1). Keel 130 may be monolithically or integrally formed as part of tibial baseplate 100, or keel 130 may be separately attachable to distal surface 134 of tibial baseplate 100. Structures of baseplate 100 that correspond to structures of baseplate 10 have corresponding reference numerals, with the number 100 being added to the reference numerals of baseplate 10 to arrive at the corresponding reference numerals of baseplate 100, except as otherwise noted.

Figure 9A:
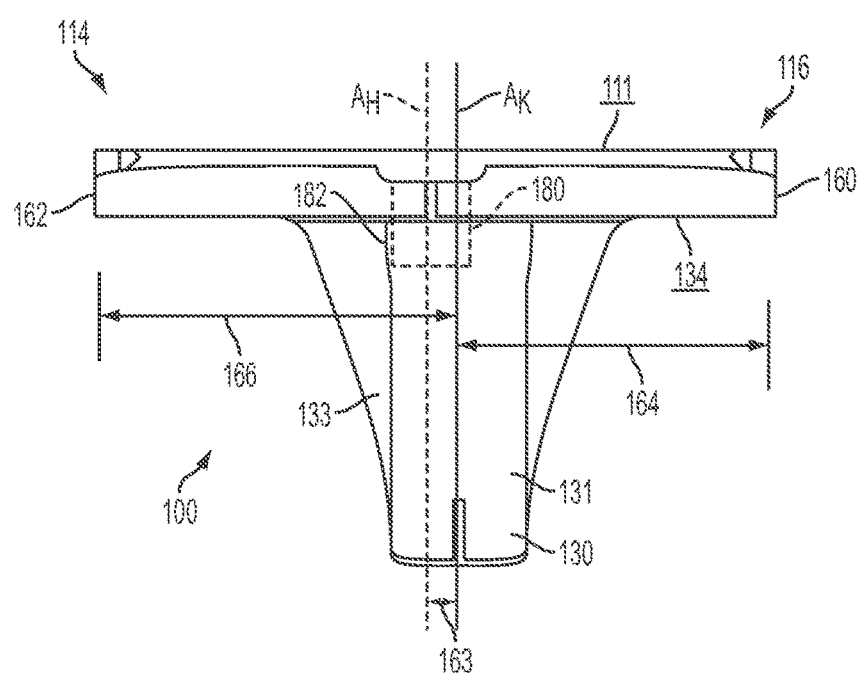
FIG. 9A is an anterior elevational view of the baseplate of FIG. 8.
Figure 9B:
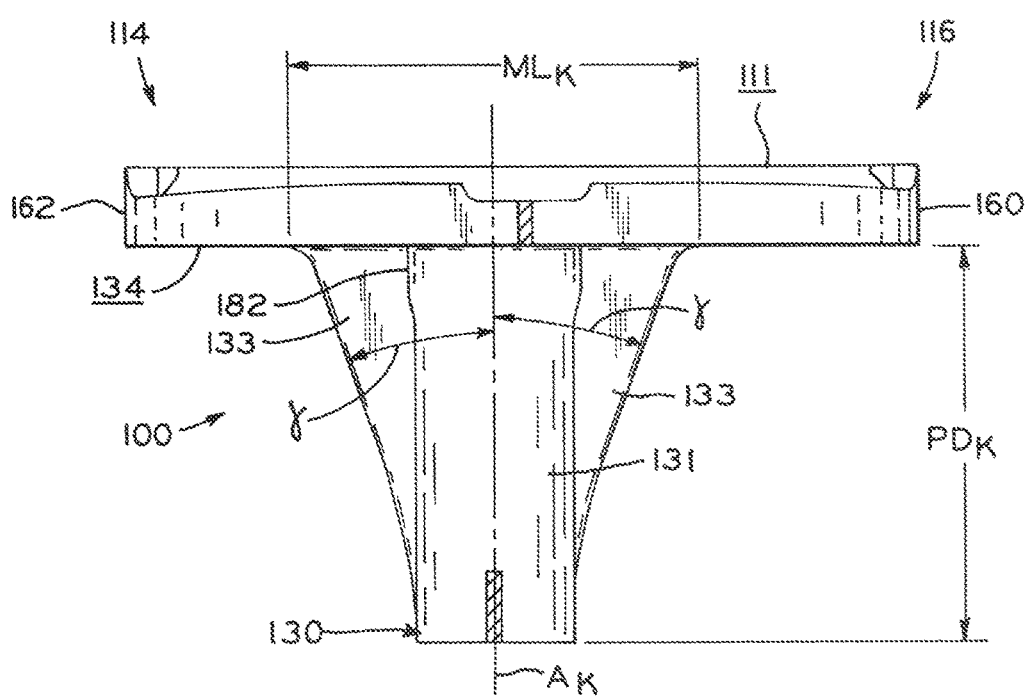
FIG. 9B is another anterior elevational view of the baseplate of FIG. 8.

The illustrative keel 130 of FIG. 9A has a cylindrical core 131 defining longitudinal axis $A_K$ (i.e., the axis of the cylinder defined by cylindrical core 131) and having two or more fins 133 extending radially outwardly therefrom, the fins being arranged symmetrically relative to the cylindrical core 131. More particularly, fins 133 extend along substantially all of the longitudinal extent $PD_K$ (FIG. 9B) of keel 130, as best shown in FIGS. 9A and 9B, such that fins 133 terminate at or near the distal tip of keel 133. In an exemplary embodiment, longitudinal extent $PD_K$ of tibial keel cylindrical core 131 may range from 27 mm to 48 mm, with smaller nominal sizes of baseplate 100 having relatively lesser extents $PD_K$ and larger nominal sizes of baseplate 100 having relatively greater extents $PD_K$.

Keel fins 133 also define keel fin angle γ with respect to longitudinal axis $A_K$ of cylindrical core 131 of keel 130. In an exemplary embodiment, keel angle γ is equal to between 22 degrees and 27 degrees. Keel fin angle γ and longitudinal extent longitudinal extent $PD_K$ of cylindrical core 131 cooperate to define a medial/lateral keel extent $ML_K$ (FIG. 9B) of between 38 mm and 54 mm, with smaller nominal sizes of baseplate 100 having relatively lesser extents $ML_K$ and larger nominal sizes of baseplate 100 having relatively greater extents $ML_K$. Advantageously, this medial/lateral extent $ML_K$ defined by fins 133 of keel 130 present high resistance to rotation of tibial baseplate 100 in vivo, and enhance the overall strength of baseplate 100.

In an exemplary embodiment, keel 130 defines a substantially cylindrical outer profile as illustrated in FIG. 9A. Where such cylindrical outer profile is employed, an exemplary embodiment of core 131 of keel 130 may maintain an outer diameter between 14 mm and 16 mm, with such diameter remaining constant across the longitudinal extent. However, it is contemplated that core 131 of keel 130 may have a conical, tapered outer profile, particularly for small-stature baseplate sizes. The taper angle may be formed, for example, by tapering core 131 of keel 130 from a circular outer diameter of 17.1 mm at the proximal terminus of keel 130 (i.e., at the junction between keel 130 and distal surface 134 of tibial baseplate 100) to a circular diameter of 13.4 mm at the distal terminus of keel 130. An exemplary conical keel used in conjunction with a small-stature baseplate size is disclosed in U.S. Provisional Patent Application Ser. No. 61/592,574 filed Jan. 30, 2012 and in U.S. Provisional Patent Application Ser. No. 61/621,374 filed Apr. 6, 2012 both entitled ASYMMETRIC TIBIAL COMPONENTS FOR A KNEE PROSTHESIS, the entire disclosures of which are hereby expressly incorporated herein by reference.

Prior art tibial baseplates include constant-diameter keels in this diameter range, such as the Zimmer NexGen Stemmed Tibial Plates and Natural Knee II Modular Cemented Tibial Plates. The NexGen Stemmed Tibial Plates and Natural Knee II Modular Cemented Tibial Plates are shown at pages 14 and 28, respectively, of the "Zimmer® Tibial Baseplate, Pocket Guide United States Version," the entire disclosure of which is hereby expressly incorporated herein by reference, a copy of which is submitted on even date herewith in an Information Disclosure Statement.

In FIG. 8, keel 130 is represented by a phantom oval to show the general location of keel 130, not necessarily the size or shape of keel 130. Rather than being cylindrical in shape, it is also within the scope of the present disclosure that core 131 of keel 130 may be conical in shape, with an outer diameter that tapers distally.

As discussed above, fixation pegs 30, 32 of baseplate 10 (FIGS. 1-3) may be designed to interact with cancellous bone surrounding the intramedullary canal of the patient's tibia T. To enhance this interaction with the cancellous bone, fixation pegs 30, 32 may be constructed of a highly porous biomaterial that accepts bone ingrowth. Keel 130 of baseplate 100 (FIGS. 8 and 9), by contrast, may be designed to fit into the intramedullary canal of the patient's tibia T. Like fixation pegs 30, 32, keel 130 may also be constructed of a highly porous biomaterial that accepts bone ingrowth. Alternatively, rather than achieving fixation via bone ingrowth, keel 130 may be constructed of a solid metal that achieves fixation via a tight interference fit with the patient's surrounding bone.

Although keel 130 may be the only fixation structure on baseplate 100, it is also within the scope of the present disclosure to combine keel 130 with additional fixation structures. In one embodiment, keel 130 may be combined with the above-described fixation pegs 30, 32 (FIGS. 1-3). On another embodiment, keel 130 may be combined with sharp spikes (not shown). Such spikes may be located in the same general areas discussed above with respect to fixation pegs 30, 32. However, unlike the blunt-tipped and porous fixation pegs 30, 32, the spikes may be sharp-tipped to pierce the patient's bone and may be solid in construction. The spikes may also have external ribs or barbs to enhance fixation with the patient's bone.

Keel 130 may also include a tapered bore (not shown) extending proximally into the distal tip of keel 130, designed to mate with a corresponding locking-taper surface of a tibial stem extension.

12. Lateral/Medial Positioning of Fixation Keel

As shown in FIG. 9A, keel 130 is asymmetrically disposed on distal surface 134 of baseplate 100 with respect to home axis $A_H$. More particularly, the longitudinal keel axis $A_K$ of keel 130 is biased medially with respect to the vertical plane that contains home axis $A_H$, i.e., keel axis $A_K$ is offset toward medial compartment 116 and away from lateral compartment 114 by offset distance 163. Throughout the following paragraphs, home axis $A_H$ and the vertical plane that contains home axis $A_H$ are used interchangeably.

According to an exemplary embodiment of the present disclosure, offset distance 163 is measured along distal surface 134 of baseplate 100. As a result, offset distance 163 is measured medially from the intersection of home axis $A_H$ and distal surface 134 to the intersection of keel axis $A_K$ and distal surface 134 (e.g., near the proximal end of keel 130). In embodiments where keel axis $A_K$ is perpendicular to distal surface 134, offset distance 163 could also be measured away from distal surface 134 (e.g., near the distal end of keel 130) without impacting the measurement. In embodiments where keel axis $A_K$ is canted relative to distal surface 134, however, the measurement could vary if taken away from distal surface 134 (e.g., near the distal end of the canted keel 130). Therefore, for consistency, the measurement is taken along distal surface 134 of baseplate 100.

In embodiments where baseplate 100 has a symmetric outer periphery 112, an anterior-posterior axis of symmetry through outer periphery 112 may be used as a "home axis" $A_H$ for referencing medial face 160, lateral face 162, keel 130, and other components of baseplate 100. This home axis $A_H$ would be substantially centered between medial face 160 and lateral face 162. With keel axis $A_K$ being medially offset from the central home axis $A_H$, keel axis $A_K$ would be positioned closer to medial face 160 than lateral face 162. Thus, medial distance 164 between keel axis $A_K$ and the medial-most portion of medial face 160 would be less than lateral distance 166 between keel axis $A_K$ and the lateral-most portion of lateral face 162.

In embodiments where baseplate 100 has an asymmetric outer periphery 112, as shown in FIGS. 8 and 9, home axis $A_H$ would not constitute an axis of symmetry and would be positioned closer to lateral face 162 than medial face 160. Depending on the degree to which keel axis $A_K$ is medially offset from home axis $A_H$, keel axis $A_K$ may still be positioned closer to medial face 160 than lateral face 162. Thus, medial distance 164 between keel axis $A_K$ and the medial-most portion of medial face 160 may be less than lateral distance 166 between keel axis $A_K$ and the lateral-most portion of lateral face 162.

The degree of medialization of keel 130 may be expressed as a ratio or a percentage and may be calculated by dividing the offset distance 163 between keel axis $A_K$ and home axis $A_H$ by the total medial/lateral width of distal surface 134 (i.e., medial distance 164 plus lateral distance 166). For baseplate 100 having the dimensions set forth in Table 1 below, for example, the degree of medialization would be approximately 6% (calculated as 5 mm/88 mm×100%).

TABLE 1

Sample Dimensions of a Large-Size Baseplate 100

| Dimension | Value (mm) | % of Total Width |
|---|---|---|
| Offset Distance 163 between Keel Axis $A_K$ and Home Axis $A_H$ | 5 | 6 |
| Medial Distance 164 | 41 | 47 |
| Lateral Distance 166 | 47 | 53 |
| Total Width (Medial Distance 164 + Lateral Distance 166) | 88 | N/A |

Advantageously, the medial bias of keel 130 (i.e., the relatively short medial distance 164 and the relatively long lateral distance 166) more closely aligns keel 130 with the intramedullary canal of the patient's tibia T (FIG. 1). Thus, upon implantation of baseplate 100 onto the patient's tibia T, keel 130 may be centered or nearly centered within the intramedullary canal. In this manner, keel 130 may avoid impinging onto hard, cortical bone around the intramedullary canal, thereby promoting firm and stable long-term fixation of tibial baseplate 100 to tibia T. The medial bias of keel 130 may also be important if it becomes necessary to attach a distal stem extension (not shown) to keel 130, such as during a revision surgical procedure. In this manner, tibial baseplate 100 may achieve an optimum metaphyseal fit on tibia T in the region of keel 130 and diaphyseal fit on tibia T in the region of the distal stem extension.

13. Lateral/Medial Positioning of Fixation Keel for Set of Prostheses

Baseplate 100 may be provided in a kit or set of different prosthesis sizes. In one embodiment, nine nominal sizes of baseplate 100 are provided in the set, with baseplates 100 growing progressively in size.

According to an exemplary embodiment of the present disclosure, the degree of medialization of keel 130 increases as the prostheses in the set grow in size. Thus, rather than maintaining a fixed relationship between medial distance 164 and lateral distance 166 as the prostheses grow in size, medial distance 164 makes up a smaller and smaller portion of the total width as the prostheses grow in size, and lateral distance 166 makes up a larger and larger portion of the total width as the prostheses grow in size. Stated differently, the rate at which keel 130 moves toward medial face 160 exceeds that rate at which the prostheses grow in size.

The dimensions of another sample baseplate 100 are provided in Table 2 below. Baseplate 100 of Table 2, which has a total width of 58 mm, is smaller than baseplate 100 of Table 1 above, which has a total width of 88 mm.

TABLE 2

Sample Dimensions of a Small-Size Baseplate 100

| Dimension | Value (mm) | % of Total Width |
|---|---|---|
| Offset Distance 163 between Keel Axis $A_K$ and Home Axis $A_H$ | 1 | 2 |
| Medial Distance 164 | 29 | 50 |
| Lateral Distance 166 | 29 | 50 |
| Total Width (Medial Distance 164 + Lateral Distance 166) | 58 | N/A |

As baseplates 100 of the present set grow in size from Table 2 to Table 1 (i.e., from a small nominal size having a 58 mm total width to a large nominal size having an 88 mm total width), the degree of medialization of keel 130 increases relative to home axis $A_H$ (from 2% to 6%). Also, as keel 130 moves medially from the small size of Table 2 to the large size of Table 1, medial distance 164 makes up a smaller portion of the total width (from 50% to 47%), and lateral distance 166 makes up a larger portion of the total width (from 50% to 53%).

Advantageously, increasing the degree of medialization of keel 130 as baseplate 100 grows in size may better track the position of the intramedullary canal as the patient's tibia T (FIG. 1) grows in size. Therefore, keel 130 may be positioned inside the intramedullary canal rather than in hard, cortical bone around the intramedullary canal.

Figure 10:
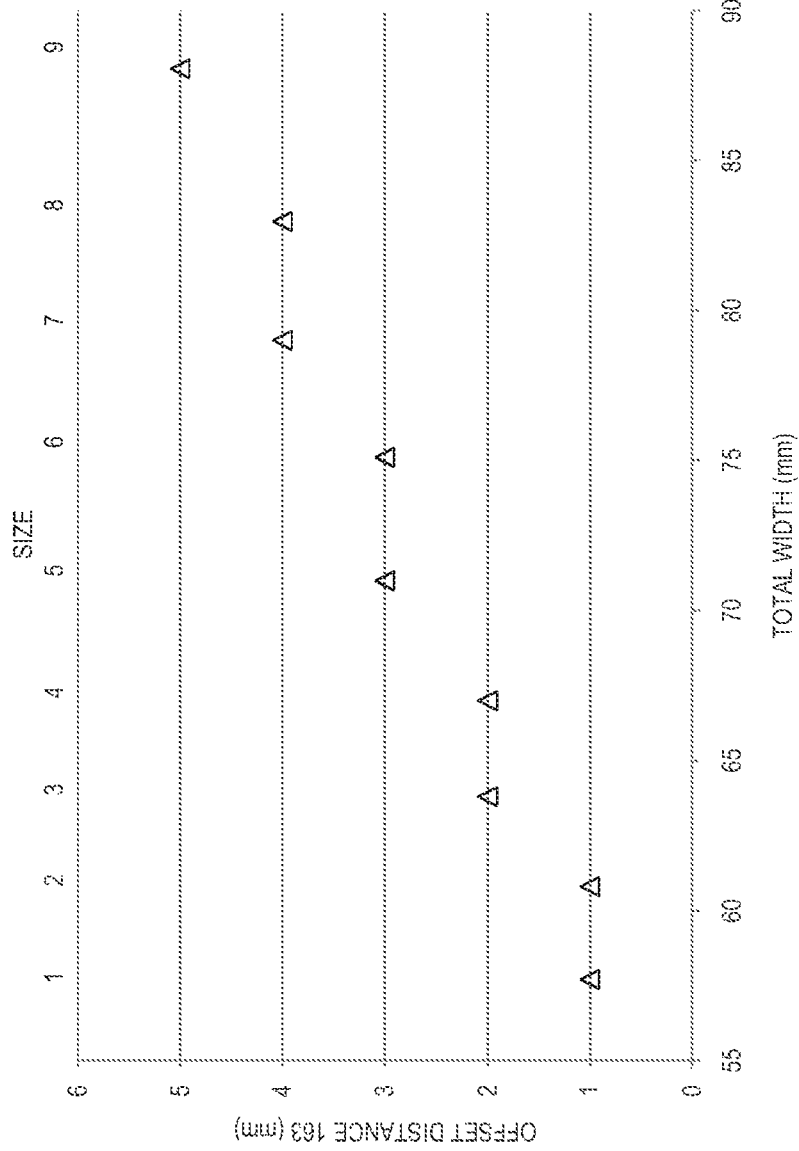
FIG. 10 is a graph illustrating the medialization of the fixation keel of FIGS. 8 and 9 across a range of prosthesis sizes.

The increasing medialization of keel 130 is presented graphically in FIG. 10, where exemplary offset distances 163 between keel axis $A_K$ and home axis $A_H$ are shown for a set of prostheses of different sizes. More specifically, exemplary offset distances 163 between keel axis $A_K$ and home axis $A_H$ are shown for a set of prostheses having different medial/lateral widths (i.e., medial distance 164 plus lateral distance 166). The data points located farther to the left represent smaller medial/lateral widths (and therefore smaller prosthesis sizes), and data points located farther to the right represent larger medial/lateral widths (and therefore larger prosthesis sizes). Although adjacent nominal prosthesis sizes may share the same offset distance 163 between keel axis $A_K$ and home axis $A_H$ (compare, for example, the corresponding offset distances 163 of the size 5 and size 6 implants, shown as the fifth- and sixth-from left data points respectively), the overall trend in FIG. 10 is that offset distance 163 increases as total medial/lateral width increases.

In a smaller bone, the metaphyseal region of tibia T is more closely aligned with the diaphyseal region of tibia T. Therefore, keel 130 may achieve an optimum metaphyseal and diaphyseal fit with a relatively small offset distance 163 (e.g., 1 mm, 2 mm). In a larger bone, by contrast, the metaphyseal region of tibia T is more offset from the diaphyseal region of tibia T. Therefore, keel 130 may require a relatively large offset distance 163 (e.g., 4 mm, 5 mm) to achieve an optimum metaphyseal and diaphyseal fit. FIG. 10 presents exemplary offset distances 163, but for any given size, offset distance 163 may vary by +/−0.5 mm, +/−1.0 mm, +/−1.5 mm, or +/−2.0 mm, for example.

Figure 11:
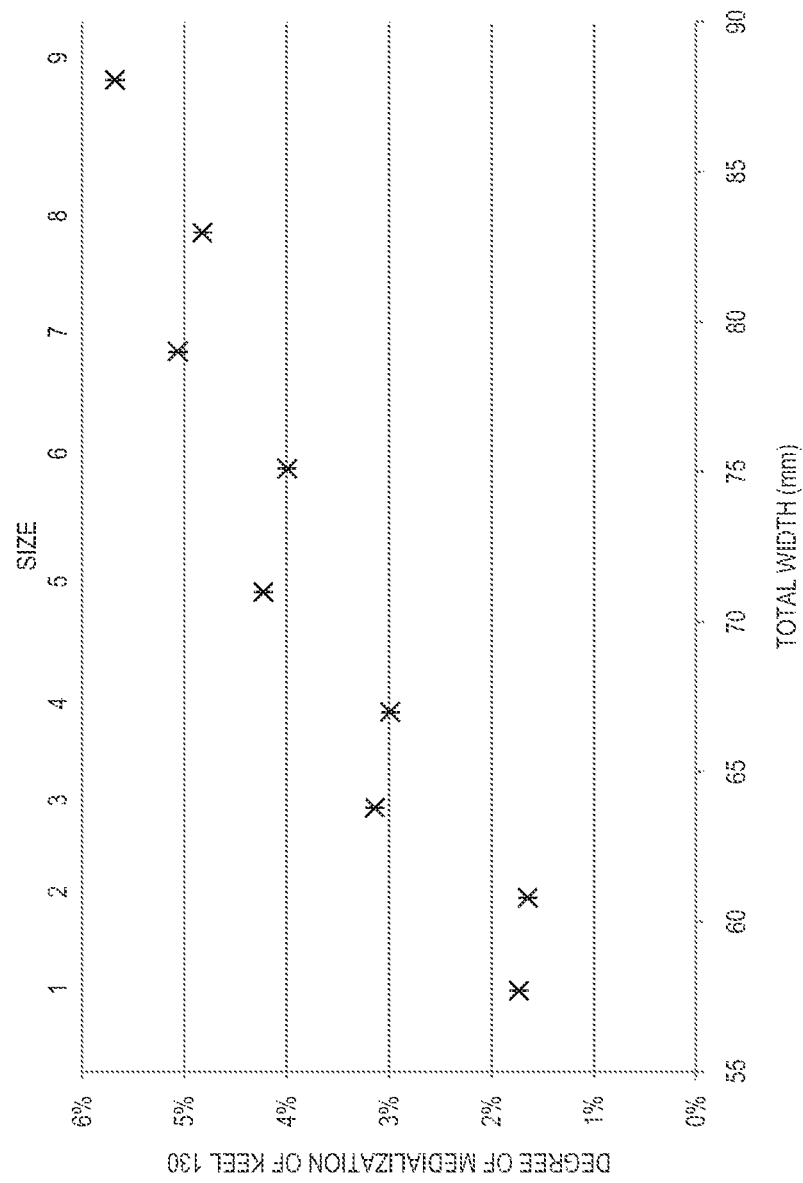
FIG. 11 is another graph illustrating the medialization of the fixation keel of FIGS. 8 and 9 across a range of prosthesis sizes.

As discussed above, the degree of medialization of keel 130 may be expressed as a percentage by dividing the offset distance 163 between keel axis $A_K$ and home axis $A_H$ by the total medial/lateral width. In FIG. 11, the offset distances 163 from FIG. 10 are shown as percentages of the total medial/lateral width. The overall trend in FIG. 11 is that the degree of medialization of keel 130 increases as medial/lateral width increases. With respect to a relatively small nominal size 3 implant, for example, the medial offset of keel 130 from home axis $A_H$ is 3% of the total medial/lateral implant width. With respect to a relatively large nominal size 7 implant, the medial offset of keel 130 from home axis $A_H$ is 5% of the total medial/lateral implant width.

14. Anterior/Posterior Positioning of Fixation Keel for Set of Prostheses

As shown in FIG. 8, the anterior/posterior keel distance 147 may be measured posteriorly from flat portion 118a of anterior face 118 to keel axis $A_K$, for example. The lateral depth 144 of lateral compartment 114 is also shown being measured posteriorly from flat portion 118a of anterior face 118 to posterior/lateral face 120 of baseplate 100 in FIG. 8, and this lateral depth 144 exceeds keel distance 147.

According to an exemplary embodiment of the present disclosure, keel distance 147 is measured along distal surface 134 of baseplate 100. As a result, keel distance 147 is measured posteriorly from the intersection of flat portion 118a of anterior face 118 and distal surface 134 to the intersection of keel axis $A_K$ and distal surface 134 (e.g., near the proximal end of keel 130). In embodiments where keel axis $A_K$ is perpendicular to distal surface 134, keel distance 147 could also be measured away from distal surface 134 (e.g., near the distal end of keel 130) without impacting the measurement. In embodiments where keel axis $A_K$ is canted relative to distal surface 134, however, the measurement could vary if taken away from distal surface 134 (e.g., near the distal end of the canted keel 130). Therefore, for consistency, the measurement is taken along distal surface 134 of baseplate 100.

Figure 12:
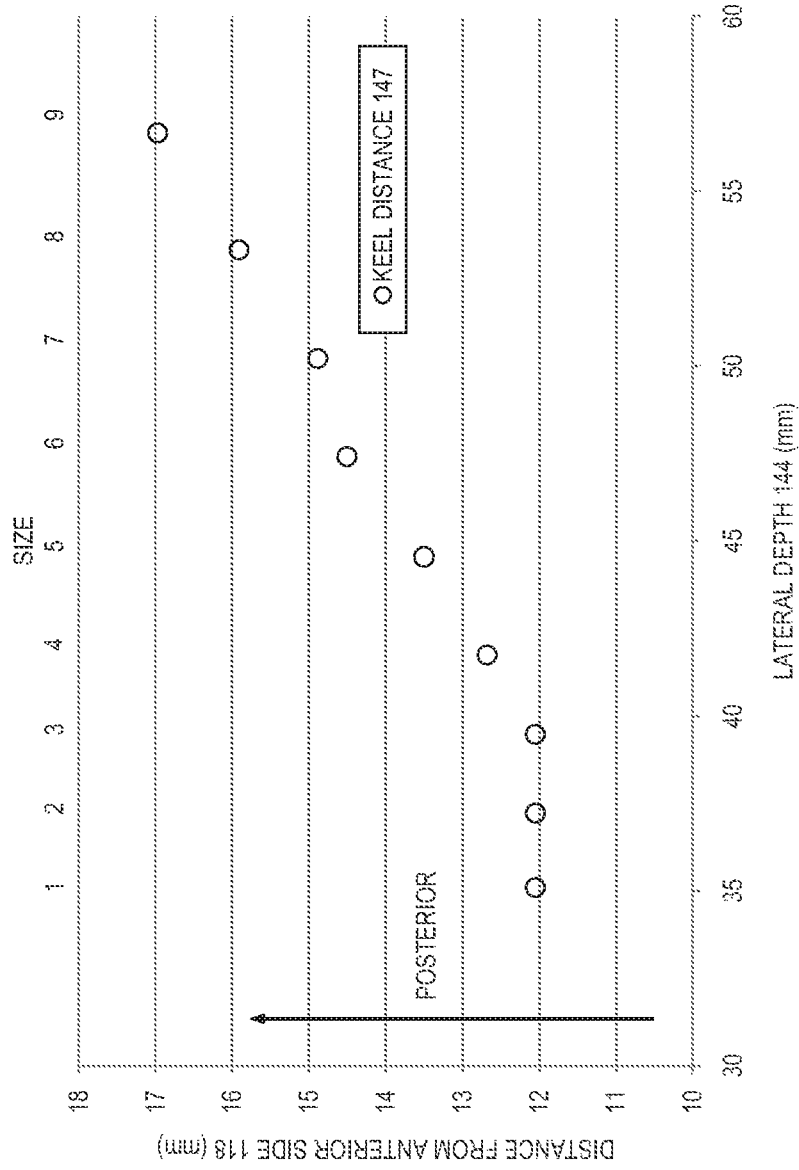
FIG. 12 is a graph illustrating the anterior/posterior positioning of the fixation keel of FIGS. 8 and 9 across a range of prosthesis sizes.

Across a set of different tibial baseplates 100 having varying nominal sizes, the anterior/posterior positioning of keel 130 may vary. In FIG. 12, for example, exemplary anterior/posterior keel distances 147 are shown for a set of prostheses of different sizes. The overall trend in FIG. 12 is that keel distance 147 increases as lateral depth 144 increases. Moving keel 130 further and further from anterior face 118 as baseplate 100 increases in size may avoid anterior cortical bone impingement by keel 130, especially if keel 130 also increases in size (e.g., diameter, length) along with baseplate 100. FIG. 12 depicts exemplary keel distances 147, but for any given size, keel distance 147 may vary by +/−0.5 mm, +/−1.0 mm, +/−1.5 mm, or +/−2.0 mm, for example.

15. Proximal Keel Expansion

As shown in FIG. 9A, the illustrative keel 130 includes a blind proximal bore 180 therein that is sized to receive a fixation structure, such as a set screw (not shown), from proximal surface 111 of baseplate 100. The fixation structure may be used to attach a tibial bearing component onto proximal surface 111 of baseplate 100, for example.

The illustrative bore 180 of FIG. 9A is centered along home axis $A_H$. However, because keel axis $A_K$ is offset from home axis $A_H$, bore 180 becomes offset in keel 130. To ensure that the walls of keel 130 surrounding bore 180 are adequately thick along the axial extent of bore 180 (e.g., 1.5 mm), keel 130 may expand radially outwardly around bore 180 to form bulge 182.

As keel 130 becomes more and more offset from home axis $A_H$ and bore 180, bulge 182 may become larger and larger in size. For example, for medium nominal prosthesis sizes (e.g., sizes 5 and 6) having medium offset distances 163 between keel axis $A_K$ and home axis $A_H$ (e.g., 3 mm), bulge 182 may increase the diameter of keel 130 by 0.5 mm. For large nominal prosthesis sizes (e.g., sizes 7-9) having large offset distances 163 between keel axis $A_K$ and home axis $A_H$ (e.g., 4 mm, 5 mm), bulge 182 may increase the diameter of keel 130 by 1.4 mm. For small nominal prosthesis sizes (e.g., sizes 1-4) having small offset distances 163 between keel axis $A_K$ and home axis $A_H$ (e.g., 1 mm, 2 mm), bulge 182 may be excluded.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tibial baseplate system comprising:
a first tibial baseplate comprising:

a first proximal surface;
a first distal surface opposite the first proximal surface; the first distal surface shaped to be disposed on a proximal resected surface of a tibia;
a first medial face;
a first lateral face opposite the first medial face; and
a first keel extending distally from the first distal surface, the first keel spaced apart from the first medial face by a first medial distance and spaced apart from the first lateral face by a first lateral distance;
wherein the first keel is medially biased toward the first medial face such that first medial distance is less than the first lateral distance; and
a second tibial baseplate comprising:
a second proximal surface;
a second distal surface opposite the second proximal surface, the second distal surface sized and shaped to substantially cover a proximal resected surface of a tibia;
a second medial face;
a second lateral face opposite the second medial face;
a second total width measured between the second medial face and the second lateral face, the second total width differing from the first total width whereby the first and second tibial baseplates comprise unique nominal sizes; and
a second keel extending distally from the second distal surface, the second keel spaced apart from the second medial face by a second medial distance and spaced apart from the second lateral face by a second lateral distance,
a first ratio of the first medial distance to the first total width differing from a second ratio of the second medial distance to the second total width.

2. The tibial baseplate system of claim 1, the first tibial baseplate further comprising:
a first medial compartment defined at least in part by the medial face, a first portion of a first anterior face and a first portion of a posterior face;
a first lateral compartment opposite the first medial compartment, wherein the first lateral compartment is defined at least in part by the first lateral face, a second portion of the first anterior face and a second portion of the posterior face; and
a first, anterior-posterior axis extending centrally between the first medial and lateral compartments throughout its length, the first keel being medially offset from the first axis by a first offset distance.

3. The tibial baseplate system of claim 2, wherein the first offset distance is between 5 mm and 0.5 mm, inclusive.

4. The tibial baseplate system of claim 2, wherein the first axis is positioned to correspond to a home axis of a patient's proximal tibia when the first tibial baseplate is implanted onto the patient's proximal tibia, the home axis defined as a line extending from a posterior point disposed at a geometric center of an attachment area between a posterior cruciate ligament and the patient's proximal tibia, to an anterior point disposed on an anterior tubercle of the patient's proximal tibia and bordering a medial third of the anterior tubercle.

5. The tibial baseplate system of claim 2, wherein the first tibial baseplate is symmetric about the first axis such that the first medial compartment and the first lateral compartment have substantially similar surface areas.

6. The tibial baseplate system of claim 2, wherein the first tibial baseplate is asymmetric about the first axis such that a first surface area of the first medial compartment differs from a second surface area of the first lateral compartment.

7. The tibial baseplate system of claim 2, further comprising a first total width measured from the first medial face to the first lateral face.

8. The tibial baseplate system of claim 7, wherein the first offset distance is less than 6 percent but greater than 1 percent of the first total width.

9. The tibial baseplate system of claim 1, wherein the first total width is greater than the second total width, and the first ratio is less than the second ratio.

10. The tibial baseplate system of claim 1, wherein the first tibial baseplate is larger than the second tibial baseplate, and wherein:
the first tibial baseplate includes the first anterior face joining the first lateral face to the first medial face, the first keel being posteriorly spaced from the first anterior face by a first distance; and
the second tibial baseplate includes a second anterior face joining the second lateral face to the second medial face, the second keel being posteriorly spaced from the second anterior face by a second distance less than the first distance.

11. A tibial baseplate system comprising:
a first tibial baseplate comprising:
a first proximal surface;
a first distal surface opposite the first proximal surface, the first distal surface shaped to be disposed on a proximal resected surface of a tibia;
a first medial compartment defined at least in part by a first medial face, a portion of a first anterior face and a portion of a first posterior face;
a first lateral compartment opposite the first medial compartment, wherein the first lateral compartment is defined at least in part by a first lateral face, a second portion of the first anterior face and a second portion of the first posted or face;
a first keel extending distally from the first distal surface; and
a first anterior-posterior axis extending centrally between the first medial and the first lateral compartments throughout a length thereof, the first keel being medially offset from the first axis by a first offset distance, wherein the first offset distance is between 5 mm and 0.5 mm, inclusive; and
a second tibial baseplate comprising:
a second proximal surface;
a second distal surface opposite the second proximal surface, the second distal surface shaped to be disposed on a proximal resected surface of a tibia;
a second medial compartment defined at least in part by a first medial face, a portion of a second anterior face and a portion of a second posterior face;
a second lateral compartment opposite the second medial compartment, wherein the second lateral compartment is defined at least in part by a second lateral face, a second portion of the second anterior face and a second portion of the second posterior face;
a second keel extending distally from the second distal surface; and
a second anterior-posterior axis extending centrally between the second medial and the second lateral compartments throughout a length thereof, the second keel being medially offset from the second axis by a second offset distance less than the first offset distance.

12. The tibial baseplate system of claim 11, wherein the first offset distance is between 5 mm and 0.5 mm, inclusive.

13. The tibial baseplate system of claim 11, wherein the first axis and the second axis are both configured to be positioned to correspond to a home axis of a patient's proximal tibia when the first tibial baseplate or the second tibial baseplate is implanted onto the patient's proximal tibia, the home axis defined as a line extending from a posterior point disposed at a geometric center of an attachment area between a posterior cruciate ligament and the patient's proximal tibia, to an anterior point disposed on an anterior tubercle of the patient's proximal tibia and bordering a medial third of the anterior tubercle.

14. The tibial baseplate system of claim 11, wherein the first tibial baseplate is asymmetric about the first axis such that a surface area of the first medial compartment differs from a second surface area of the first lateral compartment.

15. The tibial baseplate system of claim 11, further comprising a total width measured from the first medial face to the first lateral face, and wherein the first offset distance is less than 6 percent but greater than 1 percent of the total width.

16. A tibial baseplate system comprising:
a plurality of tibial baseplates each of a different unique nominal size, each of the plurality of baseplates comprising:
a proximal surface;
a distal surface opposite the proximal surface, the distal surface shaped to be disposed on a proximal resected surface of a tibia;
a medial compartment defined at least in part by a medial face, a portion of an anterior face and a portion of a posterior face;
a lateral compartment opposite the medial compartment, wherein the lateral compartment is defined at least in part by a lateral face, a second portion of the anterior face and a second portion of the posterior face;
a keel extending distally from the distal surface; and
an anterior-posterior axis extending centrally between the medial and lateral compartments throughout its length, the keel being medially offset from the axis by a offset distance;
wherein for each of the plurality of tibial baseplates the offset distance differs as a percentage basis of the total width such that a degree of medialization of the keel changes relative to the total width.

17. The tibial baseplate system of claim 16, wherein the offset distance is less than 6 percent but greater than 1 percent of the total width.

* * * * *

UNITED STATES PATENT AND TRADEMARK OFFICE
CERTIFICATE OF CORRECTION

PATENT NO. : 10,265,181 B2
APPLICATION NO. : 15/616561
DATED : April 23, 2019
INVENTOR(S) : Wentorf et al.

Page 1 of 1

It is certified that error appears in the above-identified patent and that said Letters Patent is hereby corrected as shown below:

On the Title Page

On page 7, in Column 1, item (56) under "Other Publications", Line 24, delete "Sep. 28, 2014"," and insert --Jul. 28, 2014",-- therefor On page 13, in Column 2, item (56) under "Other Publications", Line 41, delete "20q16"," and insert --2016-- therefor In the Claims In Column 23, Line 2, in Claim 1, delete "surface;" and insert --surface,-- therefor In Column 24, Line 37, in Claim 11, delete "posted or" and insert --posterior-- therefor Signed and Sealed this
Fourteenth Day of April, 2020

Andrei Iancu
*Director of the United States Patent and Trademark Office*